United States Patent [19]

O'Yang et al.

[11] Patent Number: 4,983,627

[45] Date of Patent: Jan. 8, 1991

[54] NOVEL 6-ALKYL AND 6,8-DIALKYLBICYCLO(4.2.0)OCTANE DERIVATIVES

[75] Inventors: Counde O'Yang, Sunnyvale; Walter Kurz, Mountain View; Keith A. M. Walker, Los Altos Hills; Helen Y. Wu, San Jose, all of Calif.

[73] Assignee: Syntex (U.S.A.) Inc., Palo Alto, Calif.

[21] Appl. No.: 269,811

[22] Filed: Nov. 10, 1988

[51] Int. Cl.$^5$ .................. C07C 62/32; A61K 31/21
[52] U.S. Cl. ..................... 514/510; 514/569; 514/572; 514/700; 514/703; 514/719; 514/729; 514/824; 560/56; 560/116; 560/119; 562/466; 562/498; 562/501; 568/441; 568/445; 568/633; 568/808; 568/819
[58] Field of Search ................... 560/56, 116, 119; 562/466, 498, 501; 568/441, 445, 660, 808, 819; 514/570, 569, 572, 693, 700, 703, 719, 729, 824, 633

[56] References Cited

U.S. PATENT DOCUMENTS

| 4,608,388 | 3/1986 | Kluge et al. | 514/510 |
| 4,628,110 | 12/1986 | Aristoff | 560/119 |
| 4,678,805 | 7/1987 | Kluge et al. | 514/510 |
| 4,735,966 | 4/1988 | Wu et al. | 514/510 |

OTHER PUBLICATIONS

*Journal of Organic Chemistry*, vol. 48, 5341–5348 (1983).

Primary Examiner—Michael L. Shippen
Attorney, Agent, or Firm—Brian Lewis; Tom M. Moran

[57] ABSTRACT

Compounds useful in treating or preventing gastrointestinal ulcers and in treating cardiovascular disorders such as thrombosis, hypertension and atherosclerosis are depicted in formulas (1), (2) and (3):

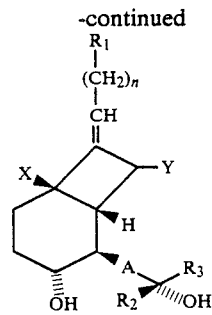

(1)

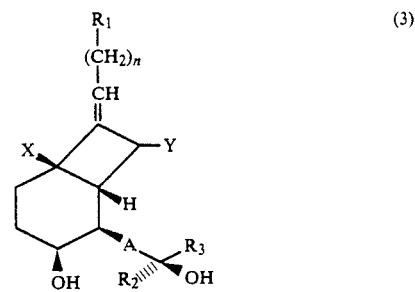

(2)

(3)

wherein:
A is —C≡C—, trans —HC=CH—, trans —CH=CHCH$_2$— or —CH$_2$CH$_2$—;
X is lower alkyl of 1-6 carbon atoms;
Y is hydrogen, exo-(lower alkyl) or endo-(lower alkyl);
n is an integer from 2-4;
R$_1$ is —CH$_2$OH, —CHO, —CO$_2$R or —CO$_2$H, and the olefin formed by the R$_1$(CH$_2$)$_n$CH= moiety is either (E) or (Z);
R$_2$ is hydrogen or methyl, or optionally —CH=CH$_2$ when A is trans —CH=CHCH$_2$—; and
R$_3$ is linear or branched alkyl, alkenyl or alkynyl having 5-10 carbon atoms,

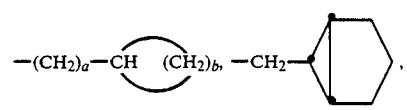

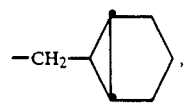

—(CH$_2$)$_m$-phenyl or CH$_2$O-phenyl;
in which each phenyl may be optionally substituted with lower alkyl, lower alkoxy, trifluoromethyl, or halogen.
in which:
a is an integer of 0, 1 or 2;
b is an integer of 3-7;
m is an integer of 0, 1 or 2; and
R is

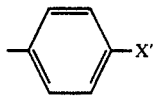
wherein X' is
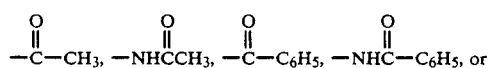
-continued
in which each $R_4$ is independently hydrogen or lower alkyl having 1-6 carbon atoms,
or a pharmaceutically acceptable, non-toxic salt or ester thereof.
46 Claims, No Drawings

NOVEL 6-ALKYL AND 6.8-DIALKYLBICYCLO(4.2.0)OCTANE DERIVATIVES

BACKGROUND OF THE INVENTION

1. Field of the Invention

This invention concerns novel derivatives of certain bicyclo[4.2.0]octanes and pharmaceutically acceptable salts and esters thereof, and in particular their use in treating gastrointestinal and cardiovascular disorders. The invention also relates to pharmaceutical compositions containing these compounds, and methods of preparing such compounds.

2. Related Disclosures

The synthesis of certain bicyclo[4.2.0]octane derivatives, useful for treating cardiovascular disorders, was disclosed in U.S. Pat. Nos. 4,608,388, 4,678,805 and 4,735,966, the relevant portions of which are hereby incorporated by reference.

Several prostaglandin analogues are known which contain bicyclic all-carbon skeletons. Carbacyclin contains a bicyclo[3.3.0]octane skeleton, and is described in several publications (*J. Chem. Soc., Chem. Commun.,* 1067, 1978, *Tetrahedron Lett.,* 3743, 1978; *Tetrahedron Lett.,* 433, 1979; *Tetrahedron Lett.,* 2807, 1979; *J. Org. Chem.* 44:2880, 1979) and patents (for example U.S. Pat No. 4,238,414). Numerous analogues of carbaprostacyclin are described (U.S. Pat. No. 4,306,076; Ger. Offen. Nos. 3,146,278; 3,204,443; *Prostaglandins, Leukotrienes Med.,* 9:307, 1982; *J. Org. Chem.* 48, 5341, 1983; *Tetrahedron Lett.* 3493, 1983; *Biochem. Pharmacol.* 32:2405, 1983; *Prostaglandins, Leukotrienes. Med.* 11:391, 1983). 9-Substituted analogs of carbacyclin are described in U.S. Pat. Nos. 4,487,960 and 4,487,961.

Synthetic prostaglandins (homo $PGE_2$ and homo $PGF_{2\alpha}$) have been prepared with the hydroxyl function and lower side chain trans-opposed in a 6-membered ring (*Tetrahedron Lett.,* 3327, 1971).

SUMMARY OF THE INVENTION

One aspect of the present invention relates to compounds of the formulas (1), (2) and (3)

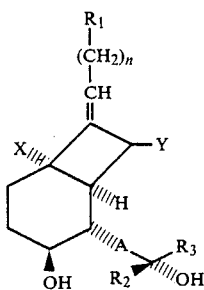 (1)

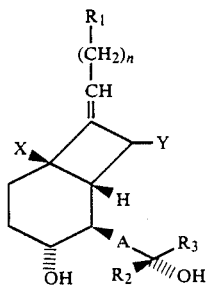 (2)

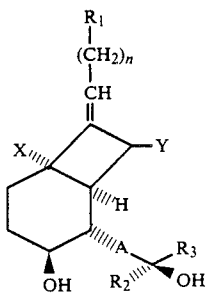 (3)

wherein:

A is $-C\equiv C-$, trans $-HC=CH-$, trans $-CH=CHCH_2-$ or $-CH_2CH_2-$;

X is lower alkyl of 1–6 carbon atoms;

Y is hydrogen, exo-(lower alkyl) or endo-(lower alkyl);

n is an integer from 2–4;

$R_1$ is $-CH_2OH$, $-CHO$, $-CO_2R$ or $-CO_2H$, and the olefin formed by the $R_1(CH_2)_nCH=$ moiety is either (E) or (Z);

$R_2$ is hydrogen or methyl, or optionally $-CH=CH_2$ when A is trans $-CH=CHCH_2-$; and $R_3$ is linear or branched alkyl, alkenyl or alkynyl having 5–10 carbon atoms,

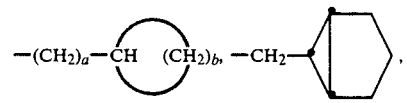

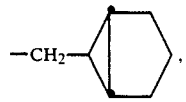

$-(CH_2)_m$-phenyl or $CH_2O$-phenyl;

in which each phenyl may be optionally substituted with lower alkyl, lower alkoxy, trifluoromethyl, or halogen.

in which:

a is an integer of 0, 1 or 2;

b is an integer of 3–7;

m is an integer of 0, 1 or 2; and

R is

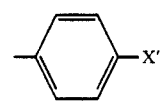

wherein X' is $-\overset{O}{\underset{\|}{C}}-CH_3$, $-NH\overset{O}{\underset{\|}{C}}CH_3$, $-\overset{O}{\underset{\|}{C}}-C_6H_5$, $-NH\overset{O}{\underset{\|}{C}}-C_6H_5$, or $-NH\overset{O}{\underset{\|}{C}}N(R_4)_2$;

in which each $R_4$ is independently hydrogen or lower alkyl having 1–6 carbon atoms, or a pharmaceutically acceptable, non toxic salt or ester thereof.

Another aspect of this invention is a method of treating gastrointestinal and cardiovascular disorders in mammals by administering a therapeutically effective amount of a compound of formula (1), (2), or (3) or a pharmaceutically acceptable salt or ester thereof.

Yet another aspect of the invention is a pharmaceutical composition containing at least one suitable pharmaceutical excipient and a compound of formula (1), (2) or (3), or a pharmaceutically acceptable salt or ester thereof.

Lastly, another aspect of the invention is a process for preparing compounds of formulas (1), (2) or (3), and their corresponding pharmaceutically acceptable, non-toxic salts and esters, as discussed below.

DETAILED DESCRIPTION OF THE INVENTION

Definitions

As used herein, the pharmaceutically acceptable, non-toxic salts of the compounds of formula (1), (2) or (3) are carboxylic acid salts obtained by reaction of the COOH moiety in formula (1), (2) or (3) with a suitable organic or inorganic base. Specific preparations are discussed hereinafter.

The pharmaceutically acceptable carboxylic esters corresponding to the acids of formula (1), (2) or (3) are prepared by conventional methods from the acid, e.g. by reaction with the appropriate diazoalkane, or reaction of an alcohol or phenol with an activated derivative of the acid optionally employing a condensing agent such as dicyclohexyl carbodiimide, by reaction of a salt with an appropriate alkylating agent, or by ester exchange from an existing ester. Specific preparations are described in the procedures and examples below.

The term "alkyl" refers to and includes saturated branched and straight chain monovalent hydrocarbon radicals containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

"Cycloalkyl" as used herein means a monovalent saturated monocyclic hydrocarbon radical containing 3–8 carbon atoms, such as cyclopropyl, cyclobutyl, cyclopentyl, cyclohexyl, cycloheptyl and cyclooctyl.

The term, "lower alkyl" refers to a branched or unbranched saturated monovalent hydrocarbon chain of 1–4 carbons, such as, for example, methyl, ethyl, n-propyl, i-butyl and the like.

The term, "alkenyl" refers to a branched or unbranched saturated monovalent hydrocarbon chain containing a double bond, such as, for example, pent-2-en-1-yl, 2-methylpent-3-en-1-yl, hex-4-en-1-yl, 2,6-dimethylhept-5 en 1-yl, and the like.

The term, "alkynyl" refers to a branched or unbranched saturated monovalent hydrocarbon chain containing a triple bond, such as, for example, pent 2-yn-1-yl, 4-methylpent 2-yn-1-yl, hex-4-yn-1-yl, hex 4-yn-2 yl, hept 4-yn-2 yl, and the like.

The term "alkoxy" refers to the radical —O—alkyl wherein "alkyl" is as defined above. This includes radicals such as methoxy, ethoxy, 2-propoxy, butoxy, 3-pentoxy and the like.

"Lower alkoxy" means the group —O—(lower alkyl) wherein lower alkyl is as defined above.

"Halo" as used herein denotes fluoro, chloro, bromo, or iodo.

"Phenyl" as used herein encompasses all possible isomeric phenyl radicals optionally monosubstituted with a substituent selected from the group consisting of lower alkyl, lower alkoxy, hydroxy, trifluoromethyl and halogen.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Epimers" are diastereoisomers which differ only in the configuration of one asymmetric center.

"Racemic mixture" means a mixture containing equal parts of individual enantiomers. "Non-racemic mixture" is a mixture containing unequal parts of individual enantiomers.

The term "ylide or stabilized anion normally associated with an olefination reaction" refers to compounds of the type $(R')_3P=CR''R''$ (ylides) or $(R')_2P(O)CR''R''$ (stabilized anions), where $R'$ is alkyl or phenyl and each $R''$ is independently hydrogen or alkyl optionally substituted with, for example, $-(CH_2)_nCO_2R''$, $-(CH_2)_nCN$ and the like. Such compounds react with an aldehyde or ketone to give an olefin where the position of the double bond is predictable. Ylides and stabilized anions where phosphorus is replaced by sulfur, silicon or nitrogen are also known and are included in this definition.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The numbering system for the bicyclo [4.2.0]octane system shown in the scheme illustration below is used in naming the intermediates and product compounds of the invention.

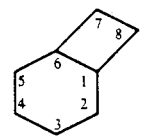

The absolute stereochemistry at carbons 1,2,3 and 6, and 3' of the side chain attached to carbon 2 are specified according to the Cahn-Ingold-Prelog R-S system. When the compound is a pure enantiomer, the stereochemistry at each chiral carbon is specified by either R or S. When a compound is a racemic mixture the stereochemistry at each chiral carbon is specified by either RS or SR by reference to a single enantiomer of the racemate. In this manner relative stereochemistry is conveyed unambiguously. The stereochemistry at carbon 8 is specified as an exo or endo isomer. When the substituent at carbon 8 is cis to the ring junction substituents (at carbons 1 and 6) it is specified as an exo-isomer. When the substituent at carbon 8 is trans to the ring junction substituents it is specified as an endo-isomer. Olefin stereochemistry is specified by the IUPAC E-Z system. Classical nomenclature is used to name a compound having a triple bond as alkynyl; and two bonds emanating from the same atom as -ylidene. Exemplary names are given in the "Preferred Embodiments" section of this application.

For the sake of simplicity, only one stereoisomer will be depicted in the description of the process. However, it is to be understood that the racemic and non racemic mixtures and all possible individual stereoisomers and mixtures thereof are also encompassed thereby. For example, the depiction of the compound of formula (12), where Y is hydrogen or exo-(lower alkyl) or endo-(lower alkyl), is intended to represent not only the structure as drawn, but also the opposite enantiomer (mirror image) and all racemic or non racemic mixtures thereof. In the case where Y is a mixture of exo-and endo-(lower alkyl) (12) represents a mixture of two optically pure enantiomers and their mirror images and all racemic or non-racemic mixtures thereof.

PREFERRED EMBODIMENTS OF THE INVENTION

Among the family of compounds of the present invention, a preferred group includes those compounds of formula (1), (2) and (3) in which the olefin formed by the $R_1(CH_2)_nCH=$ moiety is (Z). Within this group a preferred subgroup includes the compounds represented by the formulas (1) and (2).

One preferred class within this subgroup include (a) compounds in which X is lower alkyl of 1-3 carbon atoms, Y is hydrogen or lower alkyl of 1-3 carbon atoms and n is 2 or 3, especially those in which A is C≡C. More preferred embodiments of this class include those compounds $R_2$ is hydrogen and $R_3$ is

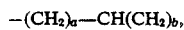

especially where a is zero and b is 5. of these, an especially preferred subclass includes those compounds in which $R_1$ is —$CO_2H$, X is methyl or ethyl and Y is hydrogen. Another especially preferred subclass includes those compounds where X is methyl, Y is exo-methyl or endo-methyl and $R_1$ is —$CO_2H$.

A second preferred class includes (b) compounds in which X is lower alkyl of 1-3 carbon atoms, Y is hydrogen or lower alkyl of 1-3 carbon atoms, n is 2 or 3 and A is trans —CH=CH—. More preferred embodiments include those compounds where $R_2$ is hydrogen, and $R_3$ is

especially where a is 0 and b is 5. Of these, especially preferred are those compounds in which $R_1$ is —$CO_2H$ and Y is hydrogen, exo-methyl or endo-methyl.

A third preferred class includes (c) those compounds in which X is lower alkyl of 1-3 carbon atoms, Y is hydrogen or lower alkyl of 1-3 carbon atoms, n is 2 or 3 and A is —$CH_2CH_2$—. More preferred embodiments of this class include those compounds where $R_2$ is hydrogen and $R_3$ is —$(CH_2)_a$

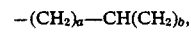

especially where a is zero and b is 5. Of these an especially preferred subclass includes those compounds in which $R_1$ is —$CO_2H$, X is methyl or ethyl and Y is hydrogen, exo-methyl or endo-methyl.

The foregoing statement of the preferred embodiments of the invention includes the pharmaceutically acceptable salts and esters, as well as the free acids of the compounds referred to above or named below. At the present time, the most preferred compounds of this invention are:

(Z)-(3'S,1S,2R,3S,6R)-4-[2 (3'-hydroxy-3'-cyclohexyl-prop-1'-ynyl)-3-hydroxy-6-ethylbicyclo[4.2.0]oct-7-ylidene]butanoic acid;

(Z)-(3'S,1S,2R,3S,6R)-4-[2-(3'-hydroxy-3'-cyclohexyl-prop-1'-ynyl)-3-hydroxy-6-methylbicyclo[4.2.0]oct-7-ylidene]butanoic acid;

(Z)-(3'S,1R,2S,3R,6S)-4-[2-(3'-hydroxy-3'-cyclohexyl-prop-1'-ynyl)-3-hydroxy-6-methyl-8-exo-methylbicyclo-[4.2.0]oct-7-ylidene]butanoic acid;

(Z)-(3'S,1S,2R,3S,6R)-4-[2-(3'-hydroxy-3'-cyclohexyl-prop-1'-ynyl)-3-hydroxy-6-methyl-8-exo-methylbicyclo-[4.2.0]oct-7-ylidene]butanoic acid;

(Z)-(3'S,1S,2R,3S,6R)-4-[2-(3'-hydroxy-3'-cyclohexyl-prop-1'-ynyl)-3-hydroxy-6-methyl-8-endo-methyl-bicyclo-[4.2.0]oct-7-ylidene]butanoic acid;

(Z)-(3'S,1S,2R,3S,6R)-5-[2-(3'-hydroxy-3'-cyclohexyl-prop-1'-ynyl)-3-hydroxy-6-methylbicyclo[4.2.0]oct-7-ylidene]pentanoic acid; and (Z)-(3'R,1S,2S,3S,6R)-4-[2-(3'-hydroxy-3'-cyclohexylprop-1-yl)-3-hydroxy-6-methylbicyclo[4.2.0]oct-7-ylidene]-butanoic acid;

METHODS OF PREPARATION

1. Compounds of Formula (1), (2) or (3) wherein $R_1$ is —$CO_2H$ (a) Where A is —C≡C— and $R_1$ is —$CO_2H$ Compounds of formula (1), (2) and (3) where A is —C≡C— and $R_1$ is —$CO_2H$ are prepared as shown in Reaction Schemes I, II and III infra.

REACTION SCHEME I
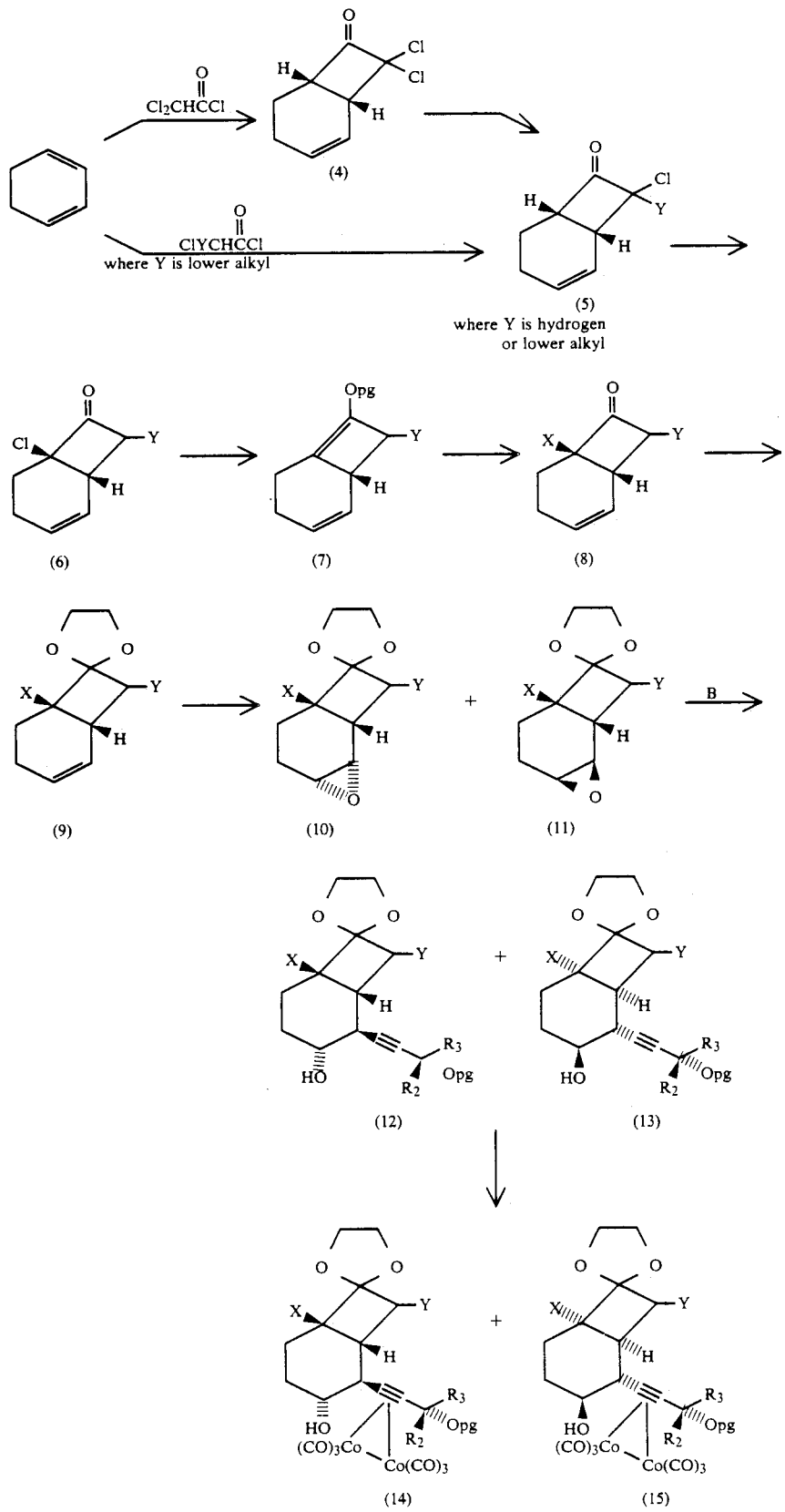

-continued
REACTION SCHEME I

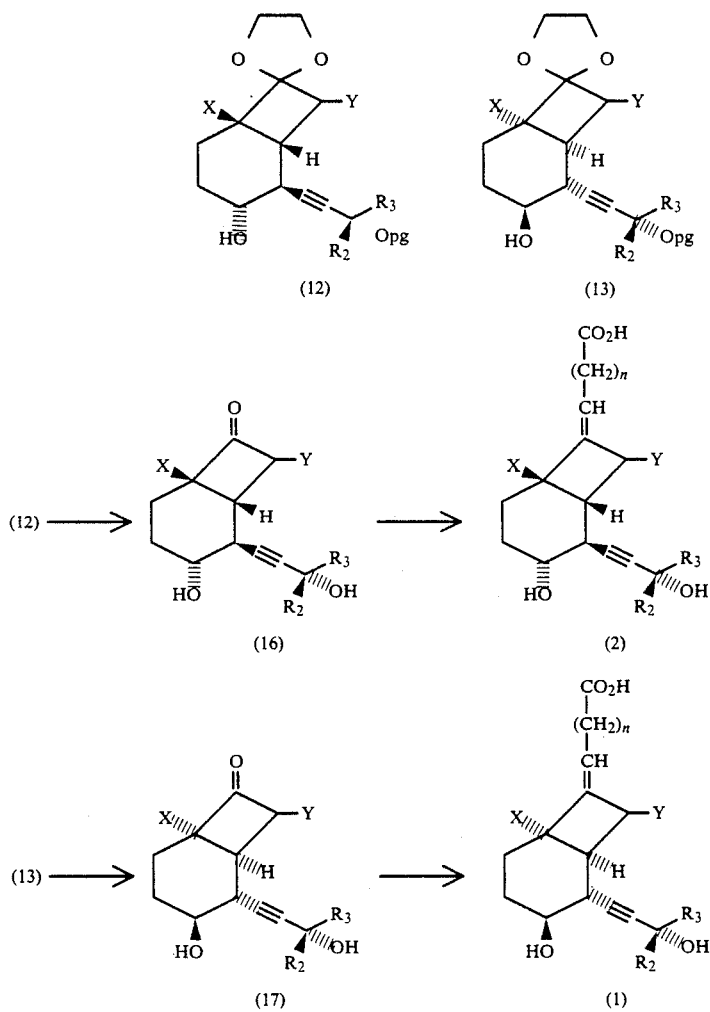

where n, $R_2$, $R_3$, X and Y are as defined above and B is a lithium acetylide of formula $LiC{\equiv}CCR_2R_3(Opg)$, where pg is a protecting group.

The synthesis of the compounds of formula (1), (2) and (3) where $R_1$ is $-CO_2H$ and A is $-C{\equiv}C-$ is illustrated in Reaction Scheme I. The preparation of the compounds where Y is hydrogen begins with the reaction of 1,3-cyclohexadiene and dichloroketene (prepared from dichloroacetyl chloride and a base) to give the compound of formula (4). Typically cyclohexadiene is reacted with about 0.5 to 1.0 molar equivalents, preferably about 0.75 molar equivalents, of dichloroacetyl chloride, the compound of formula (A), in a solvent such as hexane, tetrahydrofuran, dioxane or preferably diethyl ether in the presence of about 0.5 to 1.0 molar equivalents, preferably about 0.75 molar equivalents, of triethylamine. The reaction is carried out at a temperature of about 20° C. up to the reflux temperature of the chosen solvent, preferably about 35° C., for about 1 to 6 hours, preferably about 3 hours, or alternatively the reaction is carried out at a temperature of about 0°–30° C., preferably about 25° C., for about 8 to 48 hours, preferably about 20 hours. When the reaction is substantially complete, the product of formula (4) is isolated by conventional means.

The compound of formula (4) is then reacted with a mild dehalogenating agent, for example zinc in acetic acid or preferably tributyltin hydride. Typically, the compound of formula (4) is dissolved in an inert solvent, such as hexane, benzene, ethyl acetate, dimethoxyethane or preferably cyclohexane and reacted with about 0.75 to 2.0 molar equivalents, preferably about 1.0 molar equivalents, of tri-n-butyltin hydride in the presence of about 0.05 to 0.2 molar equivalents, preferably about 0.1 molar equivalents, of 2,2'-azobisisobutyronitrile. The reaction is carried out at a temperature of about 20° C. up to the reflux temperature of the chosen solvent, preferably about 80° C., for about 4 to 30 hours, preferably about 18 hours. When the reaction is substantially complete, the compound of formula (5) where Y is hydrogen is isolated by conventional means.

To prepare the compound of formula (5) where Y is lower alkyl, cyclohexadiene is reacted with the appropriate 2-chloroalkanonyl chloride of formula ClYCH-C(O)Cl (where Y is lower alkyl) in the same manner as shown above for the preparation of the compound of formula (4). For example, to prepare the compound of formula (5) where Y is methyl, cyclohexadiene is reacted with 2-chloropropionyl chloride.

The compound of formula (5) where Y is hydrogen or lower alkyl is then reacted to give the compound of formula (6). Typically, the compound of formula (5) is dissolved in an inert solvent, preferably toluene, in the presence of about 0.1 to 1.0 molar equivalents, preferably about 0.2 molar equivalents, of a tertiary organic base, preferably triethylamine. The reaction is carried out at a temperature of about 40° C. up to the reflux temperature of the chosen solvent, preferably at reflux, for about 4 to 48 hours, preferably about 24 hours. When the reaction is substantially complete, the product of formula (6) is isolated and purified by conventional means.

The compound of formula (6) is then converted to the compound of formula (8) via the enol silyl ether of formula (7). Typically, to a mixture of about 2 to 10 molar equivalents, preferably about 5 molar equivalents, of zinc/copper couple and about 1 to 10 molar equivalents, preferably about 3 molar equivalents, of N,N,N',N'-tetramethylethylenediamine is added a solution of about 5 to 30 molar equivalents, preferably about 15 molar equivalents, of trimethylsilyl chloride and the compound of formula (6) in an ethereal solvent such as diethyl ether, dioxane, dimethoxyethane or preferably tetrahydrofuran. The reaction is carried out at a temperature of about 0° C. to 50° C., preferably about 25° C., for about 2 to 48 hours, preferably about 18 hours. The intermediate enol silyl ether is then isolated conventionally, dissolved in an ethereal solvent, preferably tetrahydrofuran, and cooled to a temperature of about −50° C. to −100° C., preferably about 78° C. To the cold solution is added about 1 molar equivalent of an alkyllithium, preferably methyllithium, and the mixture allowed to rise to a temperature of about −5° C. to −60° C., preferably about −30° C., maintained at that temperature for about 10 minutes and then recooled to the original temperature. A mixture of about 2 to 10 molar equivalents, preferably about 6 molar equivalents, of an alkyl iodide, for example methyl iodide, and about 1 to 5 molar equivalents, preferably about 2 molar equivalents, of hexamethylphosphoramide is then added and the temperature allowed to warm to about 0° C. to 50° C., preferably about 25° C. When the reaction is substantially complete, the product of formula (8) is isolated and purified by conventional means, preferably chromatography.

The subsequent preparative procedures will be described without specifying the stereochemistry of the 8-(lower alkyl) group, where present. However, it should be understood that the preparations described are applicable equally to the 8-exo-(lower alkyl) or the 8-endo-(lower alkyl) compounds or mixtures thereof, and that both isomers are intended to fall within the scope of these preparations. The compounds of formula (1), (2) and (3) where an 8-(lower alkyl) substituent is present are preferably synthesized by carrying the initial mixture of exo and endo isomers which is obtained in the preparation of the starting material of formula (5) through to the final product, and separating the exo and endo isomers at this stage by, for example, high pressure liquid chromatography. Alternatively, the individual isomers may be separated at an earlier stage and the same procedures followed.

The compound of formula (8) is then reacted with about 1 to 50 molar equivalents, preferably about 25 molar equivalents, of ethylene glycol in a solvent such as toluene, xylene or preferably benzene in the presence of an acid catalyst such as hydrochloric acid, methanesulfonic acid, p-toluenesulfonic acid or preferably β-naphthalenesulfonic acid. The reaction is carried out at the reflux temperature of the solvent used removing water azeotropically, typically for about 4 to 36 hours, preferably about 18 hours. When the reaction is substantially complete, the product of formula (9) is isolated and purified by conventional means, preferably chromatography.

The compound of formula (9) is then reacted with about 1 to 2 molar equivalents, preferably about 1.2 molar equivalents, of a halogenating agent such as N-chlorosuccinimide or preferably N-bromoacetamide in an aqueous solvent mixture such as acetone-water. The reaction is initially carried out at about 0° C. for about 1 hour, then at a temperature of about 5°–40° C., preferably about 25° C., for about 8 to 40 hours, preferably about 20 hours. To this solution is added about 2 to 5 molar equivalents, preferably about 3 molar equivalents, of a base such as sodium hydroxide, sodium bicarbonate or preferably potassium carbonate, and the mixture stirred at a temperature of about 0°–40° C., preferably about 25° C., for about 12 hours to 3 days, preferably about 1 day. When the reaction is substantially complete, the mixture of compounds of formulas (10) and (11) is isolated and purified by conventional means, preferably chromatography.

Alternatively, the compound of formula (9) is reacted with about 1 to 2 molar equivalents, preferably about 1.1 molar equivalents, of an epoxidizing agent such as peracetic acid, perbenzoic acid or preferably m-chloroperbenzoic acid. The reaction is carried out in an inert solvent such as chloroform, cyclohexane or Preferably methylene chloride, at a temperature of about 0°–40° C., preferably about 25° C., for about 1 to 10 hours, preferably about 3 hours. When the reaction is substantially complete, the mixture of compounds of formulas (10) and (11) is isolated and purified by conventional means, preferably chromatography.

The bicyclic epoxyacetals (10) and (11) are then reacted as a mixture with a lithium acetylide of formula (B), i.e. $LiC\equiv CCR_2R_3(Opg)$, preferably chiral, where pg is a protecting group, preferably a trialkylsilyl group, and $R_2$ and $R_3$ are as defined above. The reaction is carried out in the presence of boron trifluoride etherate to give the diastereomeric alcohols of formulas (12) and (13). In the reaction of the lithium acetylenic reagent with the mixture of epoxyacetals (10) and (11), both $\alpha$ and $\beta$ epoxides undergo reaction, and the attack by the lithium acetylide reagent is not regiospecific. Thus, the reaction gives a mixture from which the desired mixture of diastereoisomers (12) and (13) is separated by chromatography. To carry out this process, the epoxides are reacted with about 1 to 2 molar equivalents, preferably about 1.3 molar equivalents, of the lithium acetylide of formula (B) in the presence of about 0.5 to 2.0 molar equivalents, preferably about 1.1 molar equivalents, of boron trifluoride etherate. The reaction is carried out in an ethereal solvent, as defined above, preferably tetrahydrofuran, for about 10 minutes to 1 hour, preferably 30 minutes, at a temperature of about −50° C. to −100° C., preferably about −78° C. When the reaction is substantially complete, the mixture of diastereomeric alcohols (12) and (13) is isolated and purified by conventional means, preferably chromatography. Preparation of the organolithium acetylides (B) is described in Reaction Scheme VIII infra.

The mixture of diastereomeric alcohols (12) and (13) is then separated into the two individual diastereoisomers (12) and (13) via their dicobalthexacarbonyl complexes. The mixture of (12) and (13) is treated with about 1 to 2 molar equivalents, preferably about 1.2 molar equivalents, of dicobalt octacarbonyl in an ethereal solvent as defined above, preferably diethyl ether. The reaction is carried out at a temperature of 0°-40° C., preferably about 25° C., for about 30 minutes to 4 hours, preferably about 1 hour. When the reaction is substantially complete, the mixture of products is isolated conventionally, and the two stereoisomers separated as their cobalt complexes (14) and (15) by chromatography. The cobalt complexes of formula (14) and (15) are then converted separately to the stereoisomers (12) or (13) by reaction with about 1 to 12 molar equivalents, preferably about 5 molar equivalents, of ceric ammonium nitrate in an aqueous solvent, for example acetone-water. The reaction is carried out for about 2 minutes at a temperature of about 25° C. When the reaction is substantially complete, the product of formula (12) or (13) is isolated and purified by conventional means, preferably chromatography.

The individual compound of formula (12) or (13) is then hydrolyzed to the ketone of formula (16) or (17) respectively. The hydrolysis also removes the protection from the 3'-hydroxy group. The compound is dissolved in an inert solvent miscible with water, for example methanol, acetone, or preferably acetonitrile, and stirred with about 1 to 10 molar equivalents, preferably about 5 molar equivalents, of an acid catalyst, such as hydrochloric acid, p-toluenesulfonic acid or preferably sulfuric acid, in water. The reaction is carried out at a temperature of about 0°-50° C., preferably about 25° C., for 30 minutes to 12 hours, preferably about 3 hours. When the reaction is substantially complete, the product of formula (16) or (17) is isolated and purified by conventional means, preferably chromatography.

The compound of formula (16) or (17) is then reacted with a phosphorus ylide or stabilized anion normally associated with an olefination reaction, preferably a phosphorus ylide of formula $(R')_3P=CH(CH_2)_nCO_2Na$, where R' is aryl, prepared from the corresponding phosphonium salt. Preferably, a triaryl phosphine, preferably triphenylphosphine, is reacted with the appropriate ω-halocarboxylic acid as described in J. Org. Chem., 27, 3404 (1962). The resulting phosphonium salt is slurried in an aprotic solvent such as diethyl ether, tetrahydrofuran or preferably dimethyl sulfoxide, at a temperature of about 0°-40° C., preferably about 25° C., and about 2.2 molar equivalents of a strong base added, such as butyl lithium, sodium amide, potassium hydride, sodium alkoxide or preferably dimsyl sodium in dimethyl sulfoxide. After about 20 minutes, 1 molar equivalent of the compound of formula (16) or (17) is added and the mixture stirred at a temperature of about 20° C.-70° C., preferably about 50° C., for about 1-10 hours, preferably about 4 hours. When the reaction is substantially complete, the products are isolated conventionally. The reaction yields a mixture of (E) and (Z) isomers of a compound of formula (1) or (2), which isomers are separated by chromatography. In this manner, the (E) and (Z) isomers of compounds of formula (1) and (2) where A is —C≡C— and $R_1$ is —CO$_2$H are obtained.

Similarly, by replacing the chiral organolithium acetylide (B) with one of opposite chirality (prepared from the acetylenic alcohol of formula (36) by protecting the hydroxy group and reacting with butyllithium as shown in Reaction Scheme (VIII), the (E) and (Z) isomers of the compound of formula (3) are prepared.

If the product compounds of our invention are prepared from optically inactive starting materials and without employment of chiral reagents, the products will be obtained as racemic mixtures of a single diastereoisomer. When chiral acetylides of formula B are used, the products obtained are optically pure. The synthesis as shown gives the compounds of formula (1), (2) or (3), each as pure enantiomer or a racemic mixture of two enantiomers.

It should also be noted that if the product compounds of our invention are prepared from optically active starting materials (i.e. one enantiomer of the bicycloketone of formula (4) or (5) and a chiral acetylide), optically pure products of formula (1), (2) and (3) are obtained without the necessity of the cobalt separation, as diastereoisomers are no longer produced. Preparation of the single enantiomers of bicycloketones of the formula (4) and (5) is disclosed in U.S. Pat. No. 4,735,966. the relevant portions of which are hereby incorporated by reference.

An alternative procedure for preparing the compound of formula (8) from the compound of formula (6) is shown in Reaction Scheme II

REACTION SCHEME II

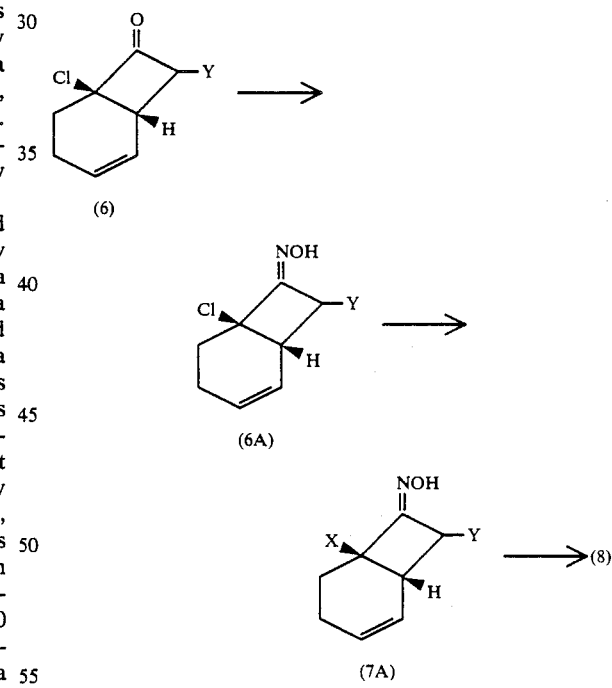

where X is as defined supra.

In this alternative preparation, the 7-keto group is first converted to an oxime. Typically, the compound of formula (6) and about 1 to 2 molar equivalents, preferably about 1.2 molar equivalents of hydroxylamine hydrochloride are dissolved in a tertiary organic base, such as triethylamine, N-methylpiperidine and the like, preferably pyridine, at about 0° C. The mixture is warmed to about 0°-40° C., preferably about 25° C., for a period of about 4-48 hours, preferably about 18 hours. When the reaction is substantially complete, the product of formula (6A) is isolated conventionally.

The compound of formula (6A) is then converted to the compound of formula (7A). Typically, to a mixture of about 2 to 10 molar equivalents, preferably about 4 molar equivalents, of cuprous iodide in an ethereal solvent such as tetrahydrofuran, dioxane, dimethoxyethane or preferably diethyl ether is added a solution of about 8 molar equivalents, of a loweralkyllithium of formula XLi where X is as defined above, for example methyllithium. The reaction is carried out at a temperature of about −20° C. to 20° C., preferably about 0° C., for about 20 minutes to 2 hours, preferably about 40 minutes. The mixture is then cooled to a temperature of about −100° C. to −50° C., preferably about −78° C., and the compound of formula (6A) in an ethereal solvent, preferably diethyl ether, added. The reaction is carried out at a temperature of about −40° C. to −80° C., preferably about −60° C., for about 20 minutes to 2 hours, preferably about 30 minutes. When the reaction is substantially complete, the product of formula (7A) is isolated and purified by conventional means, preferably chromatography.

The compound of formula (7A) is then hydrolyzed by standard methods well known in the art, for example 1N hydrochloric acid in the presence of levulinic acid, to give the compound of formula (8), which is isolated and purified by conventional means, preferably chromatography.

An alternative synthesis of the compounds of formula (1), (2) and (3) where $R_1$ is $-CO_2H$, A is $-C\equiv C-$ and Y is hydrogen or lower alkyl is shown in Reaction Scheme III. This is the preferred route by which the substituents X and Y are introduced.

For the sake of simplicity, only one stereoisomer will be depicted in the Scheme. However, it is to be understood that the racemic and non-racemic mixtures and all possible individual stereoisomers and mixtures thereof are also encompassed thereby. For example, the depiction of the compound of formula (18) is intended to represent any of the following individual structures, and the racemic and non racemic mixtures thereof.

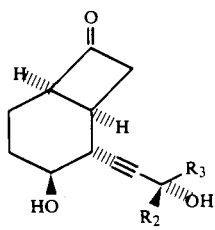

(18A)

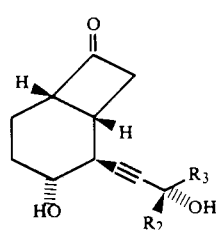

(18B)

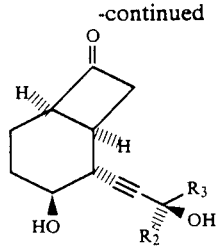

(18C)

The preparation of the isomers of the compound of formula (18) represented as (18A) and (18B), used as a starting material in Reaction Scheme III, are fully described in U.S. Pat. No. 4,608,388, which is hereby incorporated by reference. Similarly, by replacing the chiral organolithium acetylide (B) with one of opposite chirality (prepared as indicated in the section dealing with the preparation of starting materials infra), the compound of formula (18C) is prepared. If the compounds of our invention are prepared from optically inactive starting materials and without employment of chiral reagents, the products will be obtained as (optically inactive) racemic mixtures.

REACTION SCHEME III

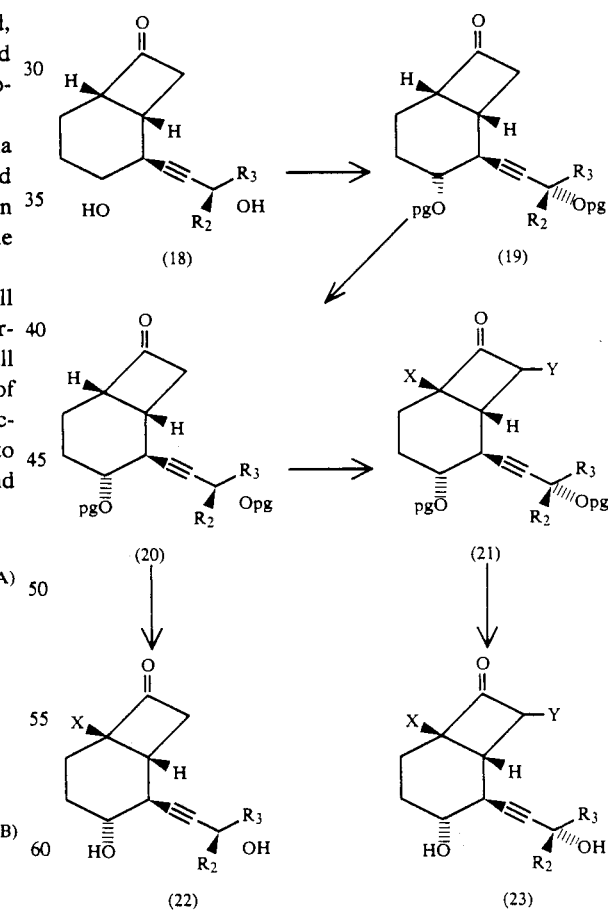

where $R_2$, $R_3$, X, Y and pg are as defined supra.

In the first step, the two hydroxy groups of the compound of formula (18) are protected by forming an ether, for example tetrahydrofuranyl ether, a substituted methyl ether or preferably a silyl ether, for example trimethylsilyl ether or most preferably t-butyldimethylsilyl ether. When a silylating agent is employed, standard conditions normally used for such a reagent are used. For example, the reaction is generally carried out in a polar aprotic solvent, preferably N,N-dimethylformamide, with an excess of the silylating reagent, 2.2 to 4 equivalents, and a greater excess relative to the silylating reagent of a mild base such as imidazole.

Preferably, the imidazole and about 3 equivalents of t-butyldimethylsilyl chloride will be added to a dry dimethylformamide solution of the hydroxy compound and stirred overnight at about room temperature, completion of the reaction being confirmed by thin layer chromatography. When the reaction is substantially complete, the product of formula (19) is isolated and purified by conventional means, preferably chromatography.

The compound of formula (19) is then converted to the compound of formula (20) by treatment with a hindered strong base, for example lithium diisopropylamide or preferably lithium bis(trimethylsilyl)amide, followed by a lower alkyl halide. For example, a solution of lithium bis(trimethylsilyl)amide is prepared by the addition of about 1 molar equivalent of an alkyllithium, preferably n-butyllithium, to 1,1,1,3,3,3-hexamethyldisilazane in an ethereal solvent as defined above, preferably tetrahydrofuran, at about $-78°$ C. and reacting for about 30 minutes. The mixture is then adjusted to a temperature of about $-100°$ C. to $-50°$ C., preferably about $-78°$ C., and the compound of formula (19) in an ethereal solvent, preferably tetrahydrofuran, is added. The reaction is carried out for about 10 minutes to 2 hours, preferably about 30 minutes at this temperature, preferably about $-78°$ C., then about 1 to 50 molar equivalents, preferably about 20 molar equivalents, of a lower alkyl halide, preferably an iodide, is added in hexamethylphosphoramide. The reaction is continued at the same temperature for about 20 minutes to 2 hours, preferably about 1 hour, then the temperature allowed to rise slowly to about $0°-40°$ C., preferably about $25°$ C., and the reaction continued at this temperature for about 1 to 6 hours, preferably about 2 hours. When the reaction is substantially complete, the product of formula (20) is isolated and purified by conventional means, preferably chromatography.

The protecting groups are then removed from the compound of formula (20) in the same manner as shown in Reaction Scheme I supra (for hydrolyzing the compound of formula (12) or (13) to the ketone of formula (16) or (17) respectively). When the reaction is substantially complete, the product of formula (22) is isolated and purified by conventional means, preferably chromatography.

The compound of formula (22) is then converted, as shown in Reaction Scheme I supra, to the compound of formula (1), (2) or (3) where Y is hydrogen, or mixtures thereof, depending upon which isomer or mixture of isomers of formula (18) is used as a starting material.

To prepare the compounds of formula (1), (2) or (3) where X and Y are both lower alkyl, the compound of formula (20) is further reacted with a hindered strong base, for example lithium diisopropylamide or preferably lithium bis(trimethylsilyl)amide, followed by a lower alkyl halide, in a similar manner as shown above for the conversion of the compound of formula (19) to the compound of formula (20). This gives the 6,8-dialkyl compound of formula (21), which is hydrolyzed with an acid, as described in Reaction Scheme I above, to the compound of formula (23), which is converted, also as shown in Reaction Scheme I supra, to the compound of formula (1), (2) or (3) where X and Y are both lower alkyl, or mixtures thereof, depending upon which isomer or mixture of isomers of formula (18) is used as a starting material.

Alternatively, the compounds of formula (1), (2) or (3) where X and Y are both the same and are both lower alkyl may be prepared by treating the compound of formula (19) with 2 molar equivalents of a hindered strong base, for example lithium diisopropylamide or preferably lithium bis(trimethylsilyl)amide, followed by an excess of a lower alkyl halide, in a similar manner as shown above for the conversion of the compound of formula (19) to the compound of formula (20). This gives the 6,8-dialkyl compound of formula (21) where X and Y are the same, which is hydrolyzed with an acid, as described in Reaction Scheme I above, to the compound of formula (23) where X and Y are the same.

Reaction Scheme III supra illustrates the introduction of the 6-alkyl or 6,8-dialkyl groups into a bicyclo[4.2.0]octane derivative of formula (19). An alternative method for preparing a compound of formula (21) is by alkylating a similar compound represented by the formula (19A), with the 8-alkyl group already present, employing the same synthetic procedures as shown in Reaction Scheme III, also giving a 6,8-dialkyl compound of formula (21).

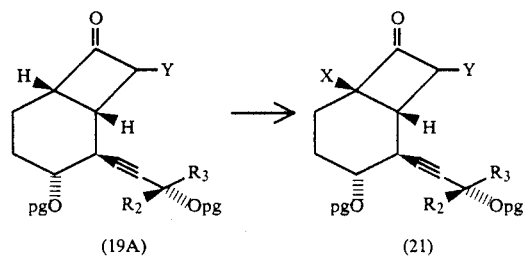

where $R_2$, $R_3$, pg, X and Y are as defined supra.

The preparation of compounds of formula (19A) is set forth in U.S. Pat. No. 4,678,805, the relevant portions of which is hereby incorporated by reference.

The compounds of the present invention where n is 2 may also be prepared according to Reaction Scheme IV, (illustrated by the case where A is $-C\equiv C-$).

REACTION SCHEME IV

(20) or (21) $\longrightarrow$ 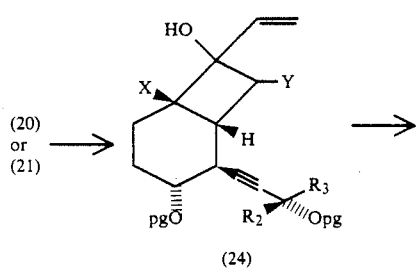 $\longrightarrow$

-continued
REACTION SCHEME IV

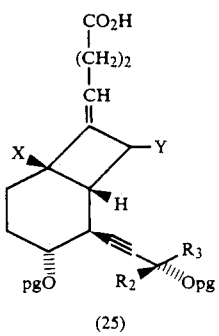

(25)

The structures as drawn are intended to represent all possible isomers and mixtures thereof, as set forth in detail supra.

Compound (20) or (21), prepared as shown in Reaction Scheme III, is reacted with a vinyl Grignard reagent to give a vinyl carbinol of the formula (24). Claisen rearrangement of the vinyl carbinol is carried out with ethyl orthoacetate in the presence of acid catalyst according to the methods described in J. Amer. Chem. Soc., 92, 741 (1970) to give compound (25) as an E/Z mixture. Separation of the E and Z isomers may be accomplished by chromatography. Saponification of the separated esters with lithium hydroxide in aqueous methanol gives the corresponding acids. Subsequently, the protecting groups at the 3- and 3' -positions may be removed by treatment with dilute aqueous acid, preferably mineral acid such as sulfuric acid in acetonitrile or with hydrogen fluoride or tetrabutylammonium fluoride in tetrahydrofuran at 0°–40° C. as described in J. Amer. Chem. Soc., 94, 6190 (1972) to form the compounds of formula (1), (2) or (3), where $R_1$ is $-CO_2H$ and A is $-C\equiv C-$. The introduction of a $=CH(CH_2)CO_2H$ group into a molecule via rearrangement of vinyl carbinols is discussed in more detail in U.S. patent application Ser. No. 900,025, the relevant portions of which are hereby incorporated by reference.

Reaction Schemes I in part describes a method of synthesizing and separating the chiral intermediates of formula (12) and (13), obtained from the reaction of the mixture of epoxides (10) and (11) with a chiral lithium acetylide of formula B. An alternative method of preparing these chiral intermediate of Reaction Scheme I, starting with a racemic compound of formula (d,1 13) is illustrated in Reaction Scheme IA below.

REACTION SCHEME IA

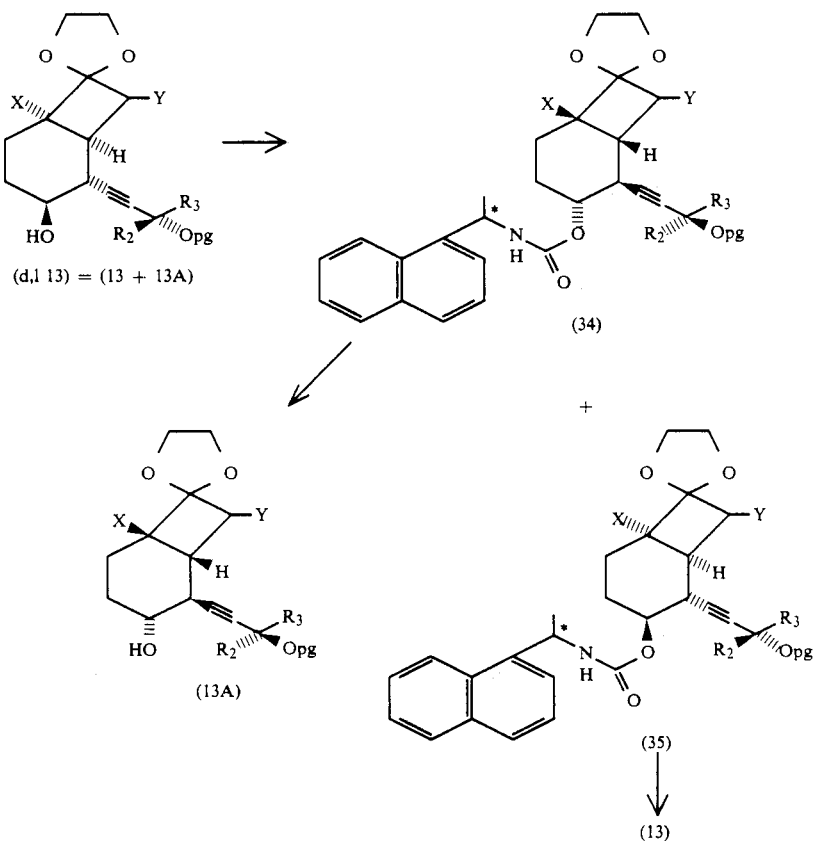

The starting point of Reaction Scheme IA is a racemic mixture indicated as (d,1 13), which represents a mixture of the isomers shown as formulas (13) and (13A). The mixture (d,1 13) is obtained by reacting the mixture of epoxides (10) and (11) with a racemic lithium acetylide of formula (B). The reaction also gives the corresponding racemic mixture (d,1 12), consisting of the compound of formula (12) and its enantiomer. The two diastereoisomers (d,1 12) and (d,1 13) are separated by the cobalt procedure, as shown in Reaction Scheme I above. Condensation of (d,1 13) with (R)-(−)-α-(1- naphthyl)ethylisocyanate gives a mixture of diastereoisomers (34) and (35). These are separated by chromatography to give the individual diastereoisomers (34) and (35). which are then reacted individually with lithium aluminum hydride to give enantiomers (13A) and (13) respectively.

Similarly, following the above procedure the compound of formula (12) is separated from its enantiomer.

This scheme is discussed in more detail in U.S. patent application Ser. No. 900,025, the relevant portions of which are hereby incorporated by reference.

(b) Where A is trans —CH=CH— and $R_1$ is —$CO_2H$

The synthesis of the compounds of formulas (1), (2) and (3), where A is trans —CH=CH— and $R_1$ is —$CO_2H$, is illustrated in Reaction Scheme V.

REACTION SCHEME V

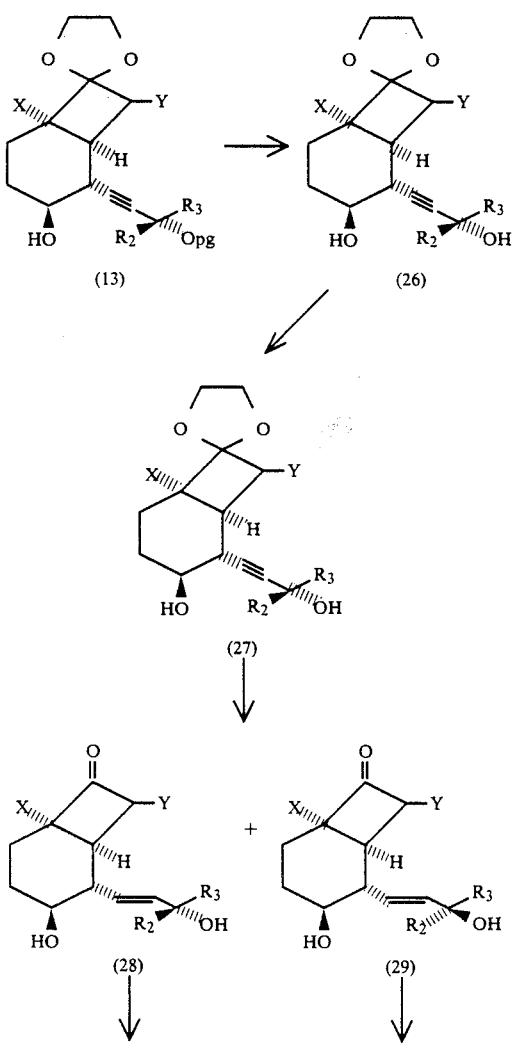

-continued
REACTION SCHEME V

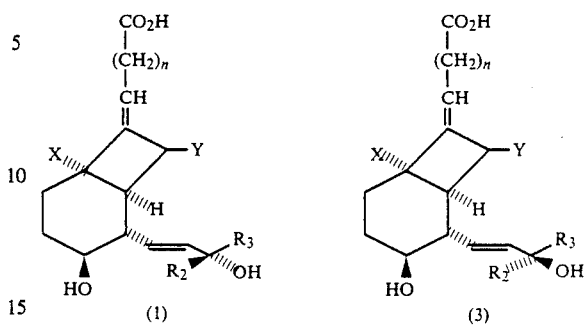

The synthesis begins with the removal of the preferred silyl protecting group from the compound of formula (12), prepared as shown in Reaction Scheme I above. For example, to remove the preferred silyl protecting group the compound of formula (12) is first dissolved in an etheral solvent as defined above, preferably tetrahydrofuran, and about 1 to 10 molar equivalents, preferably about 2.5 molar equivalents, of tetrabutylammonium fluoride in tetrahydrofuran is added. The mixture is stirred for about 1 to 20 hours, preferably about 5 hours, at about 0°–50° C., preferably about 23° C. When the reaction is substantially complete, the compound of formula (26) is isolated and purified by conventional means.

The compound of formula (26) is then reduced with lithium aluminum hydride to a trans olefin of formula (27). The compound of formula (26) is dissolved in an ethereal solvent as defined above, preferably tetrahydrofuran, and added to a solution of about 5 to 20 molar equivalents. preferably about 9 molar equivalents, of lithium aluminum hydride in tetrahydrofuran under nitrogen. The reaction is conducted at about reflux temperature for about 1 to 10 hours, preferably about 3 hours. When the reaction is substantially complete, the trans olefin of formula (27) is isolated and purified by conventional means.

The compound of formula (27) is then treated with an inorganic acid, preferably sulfuric acid, to hydrolyze the ketal group. The reaction is carried out in a mixture of a water miscible solvent as defined above, preferably acetonitrile, and dilute sulfuric acid, preferably about 1.2M, in an approximately 2:1 ratio. The mixture is stirred at about 30°–100° C., preferably about 65° C., for about 1 to 5 hours, preferably about 2 hours. This treatment simultaneously hydrolyzes the ketal group and partially epimerizes the 3'-hydroxy group on the vinylic side chain to give two diastereomeric ketones of formula (28) and (29). When the reaction is substantially complete, the products are isolated and separated by conventional means, preferably chromatography.

The individual ketones of formula (28) and (29) are then converted into the corresponding alkylidenes of formula (1) and (3) where $R_1$ is $CO_2H$ and A is trans HC=CH by reaction with a Wittig reagent or other phosphorus ylides as described in detail in Reaction Scheme I above, and similarly separated. Alternatively, the ketones of formula (28) and (29) are protected and converted to vinyl alcohols and a Claisen rearrangement carried out as described in Reaction Scheme V above.

Similarly, starting with the compound of formula (13) and following the procedures detailed above, the compound of formula (2) where $R_1$ is $-CO_2H$ and A is trans $HC=CH$ is made.

(c) Where A is $-CH=CHCH_2-$, $R_2$ is optionally $-CH=CH_2$ and $R_1$ is $-CO_2H$.

The compounds of formulas (1), (2) and (3) where A is $-CH=CHCH_2-$, $R_2$ is optionally $-CH=CH_2$ and $R_1$ is $-CO_2H$ are prepared in the same manner as shown in Reaction Schemes V above. The starting acetylenic alcohols necessary to carry out this synthesis are prepared as shown in Reaction Scheme VI.

REACTION SCHEME VI

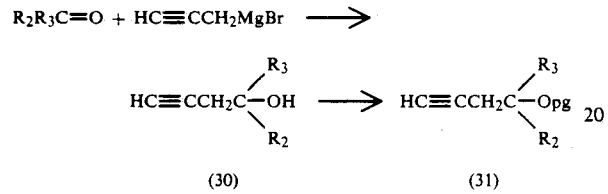

(30)  (31)

For example, when $R_2$ is hydrogen and $R_3$ is cyclohexyl, cyclohexanecarboxaldehyde is reacted with propargylmagnesium bromide to give an acetylenic alcohol of formula (30), which is protected as shown above to give a compound of formula (31), where pg is preferably t-butyldimethylsilyl. In the case where $R_2$ is $-CH=CH_2$, the protection of the alcohol group is carried out by reacting with t-butyldimethylsilyl triflate. The reactions are discussed in more detail in *J. Med. Chem.*, Vol. 25, pp. 492–494 (1982), which is incorporated herein by reference.

The compound of formula (31) is then converted to the compounds of formula (1), (2) and (3), where A is $-CH=CHCH_2-$ and $R_1$ is $-CO_2H$, as shown in Reaction Schemes I, III and IV.

(d) When A is $-CH_2CH_2-$ and $R_1$ is $-CO_2H$

The Compounds of formulas (1), (2) and (3) where A is $-CH_2CH_2-$ and $R_1$ is $-CO_2H$ are made as illustrated in Reaction Scheme VII.

REACTION SCHEME VII

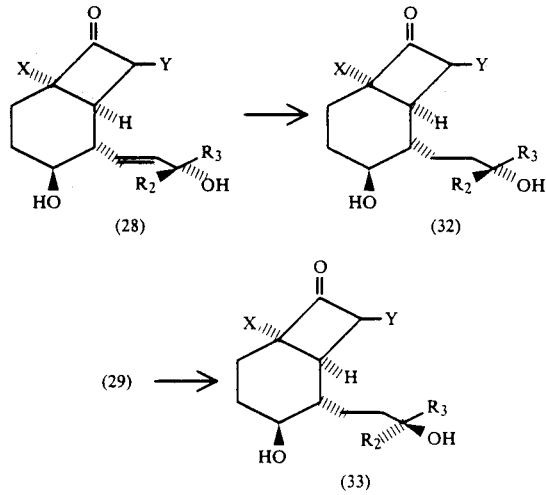

The preparation of the compounds of formulas (28) and (29) is shown in section (b) above. To prepare the compound of formula (32) or (33) the compound of Formula (28) or (29) is dissolved in an inert solvent as defined above, or methanol or preferably ethanol and reacted with hydrogen at a pressure of about 1–5 atmospheres, preferably about 1 atmosphere, in the presence of a homogeneous catalyst such as chlorotris(triphenylphosphine)rhodium (Wilkinson catalyst) or a heterogeneous catalyst such as copper chromite, platinum on carbon or preferably palladium on carbon. The reaction is conducted at a temperature of about 0°–50° C., preferably about 25° C., until about 1 molar equivalent of hydrogen is absorbed, typically in about 2 hours. When the reaction is substantially complete, the product of formula (32) or (33) is isolated by conventional means.

The ketone of formula (32) or (33) is then converted into the corresponding alkylidenes of formula (1) or (3) where $R_1$ is $-CO_2H$ and A is $CH_2CH_2$ by reaction with a Wittig reagent or other phosphorus ylides, as described in detail above in section (a). Alternatively, the ketones of formula (32) and (33) are converted to vinyl alcohols and a Claisen rearrangement carried out as described in section (a) above and illustrated in Reaction Scheme 1 A. The alkylidenes are separated into their (E) and (Z) isomers also as shown in section (a) above.

Similarly, starting with the compounds of opposite chirality to (28) and (29), (obtained from the compound of formula (13) by reaction with lithium aluminum hydride followed by hydrolyzing the product as shown in section (b) above), and following the above procedure the compound of formula (2) where $R_1$ is $-CO_2H$ and A is $CH_2CH_2$ is obtained. It is similarly separated into its (E) and (Z) isomers.

An alternative method of arriving at the ketones of formula (32) or (33) or their enantiomers is to reduce the corresponding acetylenic compounds, prepared as shown in section (a) above, by catalytic reduction as shown above, carrying out the reaction until 2 molar equivalents of hydrogen are absorbed. For example, the compounds of formula (12) or (16) could be used to arrive at the ketone of formula (32). The same subsequent procedures are then followed as shown in section (a) above to arrive at the compounds of formulas (1), (2) and (3) where A is $-CH_2CH_2-$ and $R_1$ is $-CO_2H$.

Alternatively, a method of arriving at the compounds of formula (1), (2) and (3) where A is $-CH_2CH_2-$ is to react the mixture of epoxides, the compounds of formula (10) and (11), with the corresponding saturated side chain as an organometallic reagent

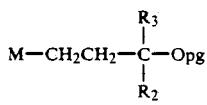

where M is a metal, preferably an alkali metal or magnesium, amd $R_2$, $R_3$ and pg are as defined above. The reagent can be prepared by standard methods from the appropriate halide by reaction with a metal, for example Mg or Li, or by exchange with a more reactive organometallic reagent, for example an aryl lithium derivative.

The pharmaceutically acceptable nontoxic salt derivatives of the compounds of formula (1), (2) and (3) are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide manganic hydroxide, isopropylamine, trimethylamine, diethylamine, triethylamine, tripropylamine, ethanolamine, 2-dimethylaminoethanol, 2-diethylaminoethanol, lysine, arginine, histidine, procaine, choline, betaine, ethylenediamine, glucosamine, methylglucamine, theobromine, purines, piperazine, piperidine, N-ethylpiperidine, polyamine resins and the like. For preparing, for example, monovalent cation salts, the free acid starting material of formula (1), (2) and (3) is treated with one molar equivalent of pharmaceutically acceptable base in an appropriate solvent such as water, methanol, ethanol, isopropanol, butanol, acetone, dioxane or tetrahydrofuran. The molar ratio of compound of formula (1), (2) or (3) to base used is chosen to provide the ratio desired by any particular salt. For preparing, example, divalent cation salts such as the calcium or magnesium salts the free acid starting material of formula (1), (2) or (3) is treated with at least one-half molar equivalent of pharmaceutically acceptable base to yield a neutral salt. Similarly, for the trivalent cation aluminum salts, at least one-third molar equivalent of the aluminum base is employed if a neutral salt product is desired.

The novel free carboxylic acids (1), (2) and (3) of out invention can be reliberated from their respective salts by treating said salts with at least stoichiometric quantities of a strong acid, preferably an inorganic acid, e.g., hydrochloric acid, sulfuric acid, and the like, at temperatures ranging from about 0° C. to about 50° C., preferably at room temperature.

The pharmaceutically acceptable nontoxic esters of the novel acids (1), (2) and (3) of our invention can be prepared, e.g. by esterifying the corresponding free acids with a solution of the appropriate diazoalkane in a suitable inert solvent such as diethyl ether. An alternative and general method for producing the esterified acids of our invention comprises reaction of a benzene solution of the carboxylic acid with an alkyl halide in the presence of the organic base diazabicycloundecane (DBU) at temperatures from about 20° C.–80° C., and for about 1–12 hours. These conditions are particularly useful for esterifying acids containing labile functionality in the molecule, such as the prostaglandins and their synthetic analogues, since they avoid the use of acid catalysts and in fact involve no harsh reagents. (N. Ono et al. *Bull. Chem. Soc. Japan*, 51, 2401–2404 (1978)).

The esters can also be prepared under mild conditions by reacting the novel acids (1), (2) or (3) with an alcohol or phenol in the presence of a dehydrating agent, for example, dicyclohexyl carbodiimide. The procedure involves reacting equivalent amounts of the acid and alcohol or phenol in a suitable solvent, for example, methylene chloride and dimethylformamide mixture in the presence of a catalytic amount of 4-dimethylaminopyridine and an equimolar amount of dicyclohexylcarbodiimide. The reaction is carried out at a temperature of about −10° C. to 25° C., preferably about 0° C., for 8 to 48 hours, preferably about 16 hours.

Typical esters are those esters derived from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, catalyzed by the corresponding alkoxide according to methods known in the art. It is preferred in preparing the esters via transesterification to go from a lower ester to a higher ester, e.g., from the methyl ester to the isoamyl ester. However, by using a substantial excess of a lower alcohol, a higher ester can be transesterified to a lower ester; thus, for example, by using a substantial excess of ethanol, the hexyl ester is converted by transesterification to the ethyl ester.

Salts of the compounds of formula (1), (2) and (3) may be interchanged by taking advantage of differential solubilities of the salts volatilities or activities of the acids, or by treating with the appropriately loaded ion exchange resin. For example, the interchange is effected by the reaction of a salt of the compounds of Formula 1), (2) or (3) with a slight stoichiometric excess of a base of a higher pKa than the base component of the starting salt. This conversion is carried out at a temperature between about 0° C. and the boiling point of the solvent being used as the medium for the procedure.

Compounds Wherein $R_1$ is —$CH_2OH$ or —CHO

Compounds of formulas (1), (2) or (3) wherein $R_1$ is —$CH_2OH$ or —CHO are prepared from the corresponding compounds (1), (2) or (3) wherein $R_1$ is —$CO_2H$. The carboxy group is first converted to an ester with, for example, diazomethane, then the hydroxy groups protected, for example as t-butyldimethylsilyloxy ethers. The ester is then reduced to an alcohol with, for example, lithium aluminum hydride, giving a compound where $R_1$ is —$CH_2OH$. This compound may be deprotected to give the compound of formula (I) where $R_1$ is —$CH_2OH$, or the —$CH_2OH$ group may be first oxidized to —CHO with, for example, pyridinium chlorochromate, which is then deprotected to give the compound of formula (I) where $R_1$ is —CHO. The reaction is discussed in more detail in U.S. patent application Ser. No. 900,025, the relevant portions of which are hereby incorporated by reference.

Compounds Wherein $R_1$ is $CO_2R$

Compounds (1), (2), and (3) wherein $R_1$ is —$CO_2R$ are prepared by reacting a compound of formula (1), (2) or (3) wherein $R_1$ is —$CO_2H$ with isobutyl chlorocarbonate to give an anhydride, which anhydride is then reacted with a substituted phenol to give compounds of formula (1), (2) and (3) wherein $R_1$ is —$CO_2R$. The phenols used in this scheme are known in the prior art and their application to the preparation of phenyl esters is described in *J. Pharm. Sci.* 68,833 (1979). The reaction is discussed in more detail in U.S. patent application Ser. No. 900,025, the relevant portions of which are hereby incorporated by reference.

Starting Materials

The optically active propargylic alcohols necessary for the preparation of the lithium acetylides of formula (B) (used as starting materials in the above Reaction Schemes) are obtained, for example, by starting from a racemic propargylic alcohol, which is prepared by methods well known to those skilled in the art. One method of obtaining the optically active isomer is to oxidize the racemic propargylic alcohol (where $R_2$ is hydrogen) to a ketone, followed by chiral reduction of the ketone to the desired optically active propargylic alcohol as shown in Reaction Scheme VIII.

REACTION SCHEME VIII

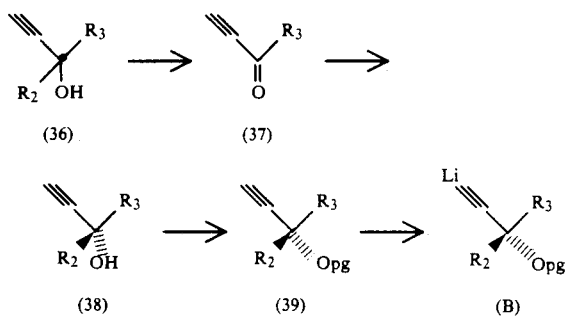

where $R_2$ where R is hydrogen and $R_3$ and pg are as defined above.

Although the hydroxy group of the chiral acetylenic alcohol of formula (38) is illustrated above as being in the α configuration, it is clear that acetylenic alcohols of opposite chirality (β configuration) may be prepared in the same manner, utilizing the appropriate chiral reducing agent.

Alternatively, the two enantiomers of a racemic propargylic alcohol may be separated as diastereomeric salts, formed by, for example, reaction of a hemiphthalate of the racemic propargylic alcohol with a chiral amine.

The preparation of such optically active propargylic alcohols, and the preparation of propargylic alcohols (and their unsaturated derivatives) in general, is discussed in more detail in U.S. Pat. No. 4,735,966, the relevant portions of which are hereby incorporated by reference.

UTILITY AND ADMINISTRATION

The compounds of the present invention are useful for the treatment and the prevention of gastrointestinal ulcers, and treatment of cardiovascular disorders; in particular they are vasodilators, and inhibit accumulation of cholesterol in the vascular wall and in plasma. They are also potent inhibitors of the aggregation of platelets and the release from them of pro-coagulant and pro-atherosclerotic factors. Accordingly, these compounds are useful in treating and preventing cardiovascular disorders involving atherosclerosis, thrombotic and vasospastic conditions. They also are useful antihypertensive and cholesterol lowering agents.

The compounds of this invention are also useful in inhibiting gastric acid secretion, and are thus useful in treating and preventing gastrointestinal ulcers.

The compounds of this invention display the spectrum of activities associated with prostacyclin. However, in contrast to prostacyclin, whose therapeutic potential is severely compromised by its extreme chemical instability, the compounds of our invention retain high biological activity while displaying much greater chemical stability, a combination of attributes identifying them as promising agents for prophylactic and/or therapeutic use particularly in the treatment of cardiovascular dysfunction and disease. Many of these compounds are potent antihypertensives. Alternatively, many of these compounds are selective in their antithrombotic effect, and they achieve this therapeutic effect without substantially affecting blood pressure.

Administration of the active compounds in the pharmaceutical composition described hereinafter can be via any of the accepted modes of administration for agents which affect the cardiovascular system. These methods include oral, parenteral, topical and otherwise systemic administration. Depending on the intended mode, the composition may be in the form of solid, semi solid or liquid dosage forms, such as, for example, tablets, suppositories, pills, capsules, powders, liquids, suspension, or the like, preferably in unit dosage forms suitable for single administration of precise dosages. The composition will include a conventional pharmaceutical carrier or excipient and an active compound of formula (1), (2) or (3) and/or the pharmaceutically acceptable salts thereof and, in addition, may include other medicinal agents, pharmaceutical agents, carriers, adjuvants, etc.

The present invention further relates to a method for treating cardiovascular disorders in mammals, which method comprises administering to a subject in need thereof an effective amount of a compound selected from those represented by formulas (1), (2) or (3) or their pharmaceutically acceptable nontoxic salts or esters, or a pharmaceutical composition incorporating such compound(s) as an active ingredient.

The present invention still further relates to pharmaceutical compositions useful for treating cardiovascular disorders. These compositions comprise an effective amount of a compound selected from those represented by formulas (1), (2) or (3) or their pharmaceutically acceptable nontoxic salts or esters in acceptable, nontoxic carrier.

The amount of active compound administered will of course, be dependent on the subject being treated, the severity of the affliction, the manner of administration and the judgment of the prescribing physician. However, an effective dosage will be in the range of 0.001–15 mg/kg/day, preferably 0.01–3 mg/kg/day. For an average 70 kg human, this would amount to 0.07–1000 mg per day, or preferably 0.7–210 mg/day.

The novel compounds of this invention may be formulated with suitable pharmaceutical vehicles known in the art to form particularly effective cardiovascular compositions. Generally, an effective amount of active ingredient is about 0.001% w to about 10% w of the total formulated composition. The rest of the formulated composition will be about 90% w to about 99.999% w of a suitable excipient.

For solid compositions, conventional nontoxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company Easton Pa. 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectibles can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.1%–10%; preferably 1–2%.

The following Preparations and Examples serve to illustrate the invention and make the invention enabling. They should not be construed as narrowing it or limiting its scope in any way. For the sake of convenience and clarity the compounds that exemplify the Preparations and Examples are for the most part named as pure enantiomers. It should be understood that the compounds may be equally prepared as racemic mixtures or as other enantiomers by the same procedures.

PREPARATION 1

Preparation of 3-Hydroxy-1-Alkynes

A. A rapid stream of acetylene was passed through a solution of 2M methyl magnesium bromide (100 ml) in THF until no more methane evolution was observed. 10 g of hexanal was added at 0° C., stirred for ½ h and a saturated solution of NH$_4$Cl was added. The organic product was isolated by extraction with ether. The ether solution was washed with water, brine, dried over MgSO$_4$ and evaporated to give a liquid, which was purified by distillation, to give oct-1 yn-3 ol, b.p. 85° C./0.1 mm Hg.

B. Similarly, following the procedure of paragraph A above, the following representative 3-hydroxy-1-alkynes are prepared:
3-cyclohexylprop-1-yn-3-ol;
dec 1-yn-3-ol;
(R) 5-methylnon-1-yn-3-ol;
non-1 yn-3-ol;
4-phenylbut 1-yn-3-ol;
5-phenylpent-1-yn-3-ol;
3 methyl-4-phenylbut-1-yn-3-ol;
4-m trifluoromethylphenylbut-1-yn-3-ol;
4 endo-bicyclo[3.1.0]hex-6-ylbut-1-yn-3-ol;
4-exo-bicyclo[3.1.0]hex-6 ylbut-1-yn-3-ol;
3-methyl-3-cyclobutylprop-1-yn-3-ol;
3-methyl-3-cyclopentylprop-1-yn-3-ol;
3-cyclopentylprop-1-yn-3-ol;
4-cyclopentylbut-1-yn-3-ol,
4-cyclohexylbut-1-yn-3-ol.
4-phenoxybut-1-yn-3-ol, and
5,9-dimethyldec-1-yn-8-en-3-ol.

PREPARATION 2

Preparation of 3-Cyclohexylprop-1-yn-3-one and Related Compands

A. A solution of chromic acid was prepared by dissolving 106.88 g chromium trioxide in 400 ml water and then adding 92 ml concentrated sulfuric acid. This solution was added in dropwise fashion over a 3 hr. period to an ice cooled, stirred solution of 120 g 3 cyclohexyl-1-propyn-3-ol, prepared as shown in Preparation 1, in 175 ml acetone. The resulting mixture was diluted with 500 ml water and the product was extracted into 1 liter of diethyl ether. The ether extract was washed with 250 ml saturated sodium bisulfite solution and was dried over sodium sulfate. The diethyl ether was removed by distillation under nitrogen atmosphere and the resulting residue was purified by Kugelrohr distillation (65° C., 0.1 mm Hg) to give 84.9 g of 3-cyclohexylprop-1-yn-3-one as an oil: MS m/z = 136 (M+) Calcd. for $C_9H_{12}O$: C, 79.37; H, 8.88. Found: C, 79.24; H, 8 60.

B. In like manner, but replacing the 3-cyclohexylprop-1-yn-3-ol with oct-1-yn-3-ol, oct-1-yn-3-one was prepared. C. Similarly, but starting with other appropriate 3-hydroxy-1-alkynes, prepared as shown above, the following 3-oxo-1-alkynes are prepared:
dec-1-yn-3-one;
(R)-5-methylnon-1-yn-3-one;
non-1-yn-3-one;
4-phenylbut-1-yn-3-one;
5-phenylpent-1-yn-3-one;
4-phenoxybut-1-yn-3-one;
4-m-trifluoromethylphenylbut-1-yn-3-one;
4-endo-bicyclo[3.1.0]hex-6-ylbut-1-yn-3-one;
4-exo-bicyclo[3.1.0]hex-6-yl-1-butyn-3-one;
3-cyclopentylprop-1-yn-3-one;
4-cyclopentylbut-1-yn-3-one; and
4-cyclohexylbut-1-yn-3-one.

PREPARATION 3

Preparation of (S)-3-cyclohexylprop-1-yn-3-ol and Related Compounds

A mixture of 1.6 liters 0.5 M 9-borabicyclo[3.3.1]-nonane in tetrahydrofuran and 122.6 g (−)-α-pinene, 99%+pure, was heated at reflux under nitrogen for 4 hr., at which time the excess (−)-α-pinene and tetrahydrofuran were removed under vacuum to leave a thick oil. The contents of the flask were cooled to 0° C. and 80 g of 3-cyclohexylprop-1-yn-3-one, prepared as shown in Preparation 2, was added with stirring. The resulting mixture was allowed to warm to 23° C. and was stirred at that temperature for 16 hr. Excess reagent was destroyed by adding 44 ml propionaldehyde and stirring at 23° C. for 1 hr. The liberated (−)-α-pinene was removed by vacuum distillation. The resulting mixture was diluted with 400 ml tetrahydrofuran followed by 300 ml 3N sodium hydroxide. To this stirred mixture was added in dropwise fashion 300 ml 30% hydrogen peroxide over 1 hr. The mixture was heated at 40° C. for 3 hr. After cooling, the mixture was extracted with diethyl ether and this extract was dried over magnesium sulfate. Evaporation of the solvent and purification of the residue by silica gel flash chromatography using 5% ethyl acetate hexane gave 56 g of (S)-3- cyclohexyl prop-1-yn-3-ol, which by nmr analysis was shown to be 90% e.e. Recrystallization from hexane gave 45 g of the pure S isomer, mp 56°-58°, $[\alpha]_D^{25} = -11.1°$ (C=0.53, Et$_2$O)

B. In like manner, but replacing the 3-cyclohexyl-prop-1-yn-3-one with oct-1-yn-3-one, prepared as described in Preparation 2, we prepared (S)-1-octyn-3-ol; $[\alpha]_D^{25} = -39.7°$ (C=1, CHCl$_3$).

C. Similarly, but utilizing instead other suitable 3-oxo-1-alkynes, prepared as shown above, the following chiral 3-hydroxy-1-alkynes are prepared:
(S)-dec-1-yn-3-ol;
(S)-tridec-1-yn-3-ol;
(3S,5R)-5-methylnon-1-yn-3-ol;
(S)-non-1-yn-3-ol;
(S)-4-phenylbut-1-yn-3-ol;
(S)-5-phenylpent-1-yn-3-ol;
(S)-4-phenoxybut-1-yn-3-ol;
(S)-4-m-trifluoromethylphenylbut-1-yn-3-ol;
(S)-4-endo-bicyclo[3.1.0]hex-6-ylbut-1-yn-3-ol;
(S)-4-exo-bicyclo[3.1.0]hex-6-ylbut-1-yn-3-ol;
(S)-3-cyclopentylprop-1-yn-3-ol;
(S)-3-cyclooctylprop-1-yn-3-ol;
(S)-4-cyclopentylbut-1-yn-3-ol; and
(S)-4-cyclohexylbut-1-yn 3 ol.

PREPARATION 4

Alternative Preparation of (S)-3-cyclohexylprop-1-yn-3-ol and Related Compounds

A. A mixture of 50 g racemic 3-cyclohexyl-1-propyn-3-ol, prepared as shown in Preparation 1, 53.3 g phthalic anhydride and 100 ml pyridine was heated at 90° C. for 4 hours. After cooling to 0° C. this mixture was added with stirring to a mixture of 350 ml concentrated hydrochloric acid and 900 ml ice. The oily solid that separated was dissolved in 600 ml diethyl ether. This solution was washed with saturated NaCl solution and dried over sodium sulfate. Evaporation and recrystallization from acetone/hexane gave the hemiphthalate, mp 136°-138° C. This hemiphthalate (38.5 g) was suspended in 80 ml dichloromethane and a solution of 16.2 g (−)-α-phenylethylamine in 250 ml dichloromethane added with stirring over 15 minutes. The mixture was filtered after 1 hour and the filtrate evaporated to give a mixture of diastereoisomeric salts. This mixture was recrystallized five times from acetonitrile to give 7 g of a pure diastereoisomeric salt mp 142°-143° C., $[\alpha]_D = -36.7$ (C=1, CHCl$_3$). This salt (2 g) was added to a stirred mixture of 25 ml 5% sodium carbonate and 25 ml diethyl ether. The ether layer was discarded and the aqueous layer extracted with 3 additional 25-ml portions of diethyl ether. The aqueous layer was acidified with 4 N HCl and extracted thoroughly with diethyl ether. The ether extract was dried over sodium sulfate and evaporated to dryness to give 1.37 g of the hemiphthalate of (S)-3-cyclohexylprop-1-yn-3-ol, mp 70°-74° C., $[\alpha]_D = -35.8°$ (C=1, CHCl$_3$). The hemiphthalate was then stirred with excess aqueous 2N potassium hydroxide for 2 hours at 60° C., the mixture cooled to room temperature and extracted with diethyl ether. The organic layer was separated, dried over sodium sulfate and the solvent removed under reduced pressure to give (S)-3-cyclohexylprop-1-yn-3-ol, m.p. 56°-58° C., $[\alpha]_D^{25°} = -11.2°$ (c=0.5, Et$_2$O).

B. Similarly, following the procedures of paragraph A above, but starting with other 3-hydroxy-1-alkynes, the following exemplary chiral 3-hydroxy-1-alkynes are prepared:
(S)-oct-1-yn-3-ol;
(S)-dec-1-yn-3-ol;
(S)-tridec-1-yn 3-ol;
(3S,5R)-5-methylnon-1-yn-3-ol;
(S)-non-1-yn-3-ol;
(S)-4-phenylbut-1-yn-3-ol;
(S)-5-phenylpent-1-yn-3-ol;
(S)-4-phenoxybut-1-yn-3ol;
(S)-4-m-trifluoromethylphenylbut-1-yn-3-ol;
(S)-4-endo-bicyclo[3.1.0]hex-6-ylbut-1-yn-3-ol;
(S)-4-exo-bicyclo[3.1.0]hex-6-ylbut-1-yn-3-ol;
(S)-3-cyclopentyl-3-methylprop-1-yn-3-ol;
(S)-3-cyclobutyl-3-methylprop-1-yn-3-ol;
(S)-3-cyclooctylprop-1-yn-3-ol;
(S)-4-cyclopentylbut-1-yn-3-ol;
(S)-3-cyclopentylprop-1-yn-3-ol; and
(S)-4-cyclohexylbut-1-yn-3-ol.

PREPARATION 5

Preparation of (S)-3-Tert-butyldimethylsilyloxyoct-1-yne and Related Silyl Ethers A. To a solution of (S)-3-cyclohexylprop-1-yn-3-ol, prepared as shown in Preparation 3 or 4, (2.76 g, 0.02 mol), in 10 ml N,N dimethylformamide (DMF), cooled to 0° C., was added imidazole (2.1 g), followed by tert-butyldimethylchlorosilane (3.1 g, 0.02 mol). The mixture was stirred for 3 h. Water (80 ml) and hexane (80 ml) were added; the organic layer was separated and combined with 2×80 ml of hexane extractions of the aqueous layer. The solvent was removed (in vacuo), after drying over sodium sulfate, to give a crude residue (4.3 g) which was chromatographed on silica gel (80 g), eluting with ethyl acetate-hexane (2:1, v/v) to afford (S)-3-tert-butyldimethylsilyloxy-3-cyclohexylprop-1-yne.

B. In like manner, but replacing the (S)-3-cyclohexylprop-1-yn-3-ol with (S)-oct-1-yn-3-ol, there was prepared (S)-3 t-butyldimethylsilyloxyoct-1-yne.

C. Similarly, following the procedures of paragraph A above, but starting instead with other suitable 3-hydroxy-1-alkynes, the following representative 3-t-butyldimethylsilyloxy-1-alkynes are prepared:
(S)-3-tert-butyldimethylsilyloxy-3-cyclohexyl-3-methyl prop-1-yne
(S)-3-t-butyldimethylsilyloxydec-1-yne;
(S)-3-t-butyldimethylsilyloxytridec-1-yne;
(3S,5R)-3-t-butyldimethylsilyloxy-5-methylnon-1-yne,
(S)-3-t-butyldimethylsilyloxynon-1-yne;
(S)-3-t-butyldimethylsilyloxy-4-phenylbut-1-yne;
(S)-3-t-butyldimethylsilyloxy-5-phenylpent-1-yne;
(S)-3-t-butyldimethylsilyloxy-4-phenoxybut-1-yne;
(S)-3-t-butyldimethylsilyloxy-4-m-trifluoromethylphenylbut-1-yne;
(S)-3-t-butyldimethylsilyloxy-4-endo-bicyclo[3.1.0]-hex-6-ylbut-1-yne;
(S)-3-t-butyldimethylsilyloxy-4-exo-bicyclo[3.1.0]-hex-6-ylbut-1-yne;
(S)-3-t-butyldimethylsilyloxy-3-cyclopentylprop-1-yne;
(S)-3-t-butyldimethylsilyloxy-3-cyclooctylprop-1-yne;
(S)-3-t-butyldimethylsilyloxy-4-cyclopentylbut-1-yne;
(S)-3-t-butyldimethylsilyloxy-4-cyclohexylbut-1-yne, and
3-t-butyldimethylsilyloxy-4-phenoxybut-1-yne.

3-t-butyldimethylsilyloxy-3-methyl-3-cyclobutyl prop-1-yne; and 3-t-butyldimethylsilyloxy-3-methyl-3-cyclopentyl prop-1-yne.

PREPARATION 6

Preparation of 8-chlorobicyclo[4.2.0]oct-2-en-7-one and related compounds of formula (5)

A. A mixture of 238 g of cyclohexadiene and 245 g of dichloroacetyl chloride in 2 litres of diethyl ether under nitrogen was refluxed while adding 220 g of triethylamine dropwise over a period of 3 hours. The mixture was then stirred at room temperature for 20 hours and filtered. The filtrate was washed with brine, 1 N hydrochloric acid, saturated sodium bicarbonate and then dried over anhydrous sodium sulfate. The solvent was removed under reduced pressure and the residue distilled to give 224 g of 8,8-dichlorobicyclo[4.2.0]oct-2-en-7-one, the compound of formula (4).

B. A solution of 191 g of 8,8-dichlorobicyclo[4.2.0]oct-2-en-7-one in cyclohexane was stirred at room temperature and 291 g of tributyltin hydride added, followed by 16 g of 2,2'-azobisisobutyronitrile. The mixture was heated to a gentle reflux for four hours, then stirred overnight at 60° C. The mixture was filtered, the solvent removed from the filtrate under reduced pressure and 2 litres of diethylether added. The solution was washed with an aqueous solution of potassium fluoride, and the white solid thus produced was filtered off and washed with ether. The combined filtrates were concentrated under reduced pressure, giving 280 g of an oil, which was further purified by distillation under vacuum, b.p. 110°–130° C. at 0.1 mm.

C. Similarly, starting with 2-chloropropionyl chloride in place of dichloroacetyl chloride and following the procedure of paragraph A above, the following mixture of compounds of formula (5) where Y is methyl was obtained:

8-endo-chloro-8-exo-methylbicyclo[4.2.0]oct-2-en-7-one; and

8exo-chloro-8-endo-methylbicyclo[4.2.0]oct-2-en-7-one, which were separated by chromatography on silica gel, eluting with a mixture of methylene chloride and hexane (1:1).

D. Similarly, starting with the appropriate 2-chloroalkanoyl chloride in place of 2-chloropropionyl chloride in preparation 1A above, the following mixtures of compounds of formula (5) where Y is lower alkyl are prepared:

8-exo-chloro-8-endo-ethylbicyclo[4.2.0]oct-2-en-7-one, and 8-endo-chloro-8-exo-ethylbicyclo[4.2.0]oct-2-en-7-one;

8-exo-chloro-8-endo-n-butylbicyclo[4.2.0]oct-2-en-7-one; and

8endo-chloro-8-exo-n-butylbicyclo[4.2.0]oct-2-en-7-one.

PREPARATION 7

Preparation of 6-chlorobicyclo[4.2.0]oct-2-en-7-one and related compounds of formula (6)

A solution of 30 g of 8-chlorobicyclo[4.2.0]oct-2-en-7-one, prepared as shown in Preparation 6, in 400 ml of toluene containing 5 ml of triethylamine was refluxed for 24 hours. The mixture was then filtered and the solvent removed from the filtrate under reduced pressure. The residue was chromatographed on silica gel, eluting with 7% ethyl acetate in hexane, to give 6-chlorobicyclo[4.2.0]oct-2-en-7-one, the compound of formula (6) where Y is hydrogen, 18 g.

B. Similarly, starting with the appropriate compound of formula (5) in place of 8-chlorobicyclo[4.2.0]oct-2-en-7-one in paragraph A above, the following compounds of formula (6) where Y is lower alkyl are prepared:

6-chloro-8-exo-methylbicyclo[4.2.0]oct-2-en-7-one;

6-chloro 8-endo-methylbicyclo[4.2.0]oct-2-en-7-one;

6-chloro-8-endo-ethylbicyclo[4.2.0]oct 2-en-7-one, 6-chloro-8-exo-ethylbicyclo[4.2.0]oct-2-en-7-one;

6-chloro-8-endo-isobutylbicyclo[4.2.0]oct-2-en-7-one; and 6-chloro-8-exo-isobutylbicyclo[4.2.0]oct-2-en-7-one.

6-chloro-8-endo-n-hexylbicyclo[4.2.0]oct-2-en-7-one; and 6-chloro-8-exo-n-hexylbicyclo[4.2.0]oct-2-en-7-one.

PREPARATION 8

Preparation of 6-methylbicyclo[4,2,0]oct-2-en-7-one and Related Compounds of Formula (8)

A mixture of 2.7 ml of tetramethylethylenediamine and 2.0 g of zinc-copper couple in 30 ml of tetrahydrofuran was stirred at room temperature, and a solution of 11.3 ml of chlorotrimethylsilane and 950 mg of 6-chlorobicyclo[4.2.0]oct-2-en-7 one, prepared as shown in Preparation 7, in 30 ml of tetrahydrofuran added dropwise. The mixture was stirred overnight at room temperature, then the precipitate filtered off, washed with ether and the combined filtrates evaporated under reduced pressure. The residue was treated with a mixture of diethylether and hexane, the precipitate filtered off and solvent removed from the filtrate under reduced pressure. The residue was dissolved in 10 ml of tetrahydrofuran, cooled to −78° C., 4 ml of 1.5M methyllithium added, stirred at −78° C. for 10 minutes, then at −30° C. for 10 minutes, recooled to −78° C. and a mixture of 5.1 g of methyl iodide and 2.1 ml of hexamethylphosphoramide added. The temperature was allowed to rise to room temperature while stirring. The mixture was poured into water, extracted with ether and the solvent removed from the extract carefully under moderately reduced pressure. The residue was chromatographed on silica gel, eluting with 10% ether in pentane, giving 400 mg of 6-methylbicyclo[4.2.0]oct-2-en-7-one, the compound of formula (8) where Y is hydrogen.

B. Similarly, starting with the appropriate compound of formula (6) in place of 6-chlorobicyclo[4.2.0]oct-2-en-7-one in paragraph A above, the following compounds of formula (8) where Y is hydrogen, or Y is lower alkyl (exo or endo) are prepared:

6-ethylbicyclo[4.2.0]oct-2-en-7-one;

6-isopropylbicyclo[4.2.0]oct-2-en-7-one;

6-n-hexylbicyclo[4.2.0]oct-2-en-7-one;

6-methyl-8-methylbicyclo[4.2.0]oct-2-en-7-one;

6-methyl-8-ethylbicyclo[4.2.0]oct-2-en-7-one;

6-methyl-8-isobutylbicyclo[4.2.0]oct-2-en-7-one;

6-methyl-8-n-hexylbicyclo[4.2.0]oct-2-en-7-one;

6-ethyl-8-methylbicyclo[4.2.0]oct-2-en-7-one;

6-ethyl-8-ethylbicyclo[4.2.0]oct-2-en-7-one;

6-ethyl-8-isobutylbicyclo[4.2.0]oct-2-en-7-one;

6-isopropyl-8-methylbicyclo[4.2.0]oct-2-en-7-one;

6-isopropyl-8-ethylbicyclo[4.2.0]oct-2-en-7-one;

6-isopropyl-8-isobutylbicyclo[4.2.0]oct-2-en-7-one;

6-n-hexyl-8-methylbicyclo[4.2.0]oct-2-en-7-one; and 6-n-hexyl-8-n-hexylbicyclo[4.2.0]oct-2-en-7-one.

PREPARATION 9

Preparation of spiro[6-methylbicyclo-[4.2.0]oct-2-ene-7,2'-(1',3'-dioxolane)] and Related Compounds of Formula (9)

A. A mixture of 6.0 g of 6-methylbicyclo[4.2.0]oct-2-en-7-one, prepared as shown in Preparation 8, 50 ml of ethylene glycol, 250 ml of benzene, and 200 mg of β-naphthalenesulfonic acid was heated at reflux for 4 hrs using a Dean-Stark trap to effect continuous removal of water. The cooled reaction mixture was poured on to 100 ml saturated sodium bicarbonate solution and the resulting mixture extracted with three 75 ml portions of diethyl ether. The combined organic extract was washed with 100 ml saturated sodium chloride solution and then dried over sodium sulfate. The solvent was removed under vacuum and the residue chromatographed on silica gel, eluting with 20% hexane in isopropyl chloride followed by methylene chloride, giving 6.2 g of spiro[6-methylbicyclo-[4.2.0]oct-2-ene-7,2'-(1',3'-dioxolane)], the compound of formula (9).

B. Similarly, starting with the appropriate compound of formula (8) in plate of 6-methylbicyclo[4.2.0]oct-2-en-7-one in paragraph A above, the following compounds of formula (9) where Y is hydrogen, or Y is lower alkyl (exo or endo) are prepared:

spiro[6-ethylbicyclo[4.2.0]oct-2-ene-7,2'-(1',3'-dioxolane)];
spiro[6-isopropylbicyclo[4.2.0]oct-2-ene-7,2'-(1',3'-dioxolane)];
spiro[6-n-hexylbicyclo[4.2.0]oct-2-ene-7,2'-(1',3'-dioxolane)];
spiro[6,8-dimethylbicyclo[4.2.0]oct-2-ene-7,2'-(1',3'-dioxolane)];
spiro[6-methyl-8-ethylbicyclo[4.2.0]oct-2-ene-7,2'-(1',3'-dioxolane)];
spiro[6-methyl-8-isobutylbicyclo[4.2.0]oct-2-ene-7,2'-(1',3'-dioxolane)];
spiro[6-methyl-8-n-hexylbicyclo[4.2.0]oct-2-ene-7,2'-(1',3'-dioxolane)];
spiro[6-ethyl-8-methylbicyclo[4.2.0]oct-2-ene-7,2'-(1',3'-dioxolane)];
spiro[6-ethyl-8-ethylbicyclo[4.2.0]oct-2-ene-7,2'-(1',3'-dioxolane)];
spiro[6-ethyl-8-isobutylbicyclo[4.2.0]oct-2-ene-7,2'-(1',3'-dioxolane)];
spiro[6-isopropyl-8-methylbicyclo[4.2.0]oct-2-ene-7,2'-(1',3'-dioxolane)];
spiro[6-isopropyl-8-ethylbicyclo[4.2.0]oct-2-ene-2'-(1',3'-dioxolane)];
spiro[6-isopropyl-8-isobutylbicyclo[4.2.0]oct-2-ene-7,2'-(1',3'-dioxolane)];
spiro[6-n-hexyl-8-methylbicyclo[4.2.0]oct-2ene-7,2'-(1',3'-dioxolane)]; and
spiro[6-n-hexyl-8-n-hexylbicyclo[4.2.0]oct-2-ene-7,2'-(1',3'-dioxolane)].

PREPARATION 10

Preparation of (1RS,2SR,3RS,6RS)-Spiro[2,3-epoxy-6-methylbicyclo[4.2.0]octane-7,2'-(1',3'-dioxolane)] and (1RS,2RS,3SR,6RS)-Spiro[2,3-epoxy-6-methylbicyclo[4.2.0]octane-7,2'-(1',3'-dioxolane)] and Related Compounds of Formulas (10) and (11)

A. To a stirred solution of 4 g of spiro [6-methylbicyclo[4.2.0]oct-2-ene-7,2'-(1',3'-dioxolane)], prepared as shown in Preparation 9, in 50 ml acetone and 25 ml water at 0° C. was added 3.4 g of N-bromoacetamide over 1 hour. This mixture was stirred at room temperature for 20 hours. To this solution was added 8.4 g potassium carbonate and the resulting mixture was stirred at room temperature for 1 day. The mixture was saturated with sodium chloride and the resulting mixture extracted with four 150 ml portions of diethyl ether. The combined organic extract was washed with 100 ml of saturated sodium chloride solution and dried over sodium sulfate. Removal of solvent in vacuum and chromatographic purification of the residue on silica gel eluting with 17% ethyl acetate-hexane gave 3.41 g of a ca. 4:1 mixture of (1RS,2SR,3RS,6RS) spiro[2,3-epoxy-6-methylbicyclo-[4.2.0]octane - 7,2' - (1',3' - dioxolane)] and (1RS,2RS,3SR,6RS) spiro[2,3-epoxy-6-methylbicyclo[4.2.0]octane-7,2'-(1',3'-dioxolane)], the compounds of formula (10) and (11) respectively.

B. Similarly, starting with the appropriate compound of formula (9) in place of spiro [6-methylbicyclo[4.2.0]oct-2-ene-7,2'-(1',3'-dioxolane)] in paragraph A above, the following mixtures of compounds of formula (10) and (11) where Y is hydrogen, or Y is lower alkyl (exo or endo) are prepared:

(1RS,2SR,3RS,6RS)- and (1RS,2RS,3SR,6RS)-spiro[2,3-epoxy-6-ethylbicyclo[4.2.0]octane-7,2'-(1',3'-dioxolane)];
(1RS,2SR,3RS,6RS)- and (1RS,2RS,3SR,6RS)-spiro[2,3-epoxy-6-isopropylbicyclo[4.2.0]octane-7,2'-(1',3'-dioxolane)];
(1RS,2SR,3RS,6RS)- and (1RS,2RS,3SR,6RS)-spiro[2,3-epoxy-6-n-hexylbicyclo[4.2.0]octane-7,2'-(1',3'-dioxolane)];
(1RS,2SR,3RS,6RS)- and (1RS,2RS,3SR,6RS)-spiro[2,3-epoxy-6,8-dimethylbicyclo[4.2.0]octane-7,2'-(1',3'-dioxolane)];
(1RS,2SR,3RS,6RS)- and (1RS,2RS,3SR,6RS)-spiro[2,3epoxy-6-methyl-8-ethylbicyclo[4.2.0]octane-7,2'-(1',3'-dioxolane)];
(1RS,2SR,3RS,6RS)- and (1RS,2RS,3SR,6RS) spiro[2,3-epoxy-6-methyl-8-isobutylbicyclo[4.2.0]octane-7,2'-(1',3'-dioxolane)];
(1RS,2SR,3RS,6RS)- and (1RS,2RS,3SR,6RS)-spiro[2,3-epoxy-6-methyl-8-n-hexylbicyclo[4.2.0]octane-7,2'-(1',3'-dioxolane)];
(1RS,2SR,3RS,6RS)- and (1RS,2RS,3SR,6RS)-spiro[2,3-spiro[2,3-epoxy-6-ethyl-8-ethylbicyclo[4.2.0]octane-7,2'-(1',3'-dioxolane)];
(1RS,2SR,3RS,6RS)- and (1RS,2RS,3SR,6RS)-spiro[2,3-epoxy-6-ethyl-8-isobutylbicyclo[4.2.0]octane-7,2'-(1',3'-dioxolane)];
(1RS,2SR,3RS,6SR)- and (1RS,2RS,3SR,6SR)-spiro[2,3-epoxy-6-isopropyl-8-methylbicyclo[4.2.0]octane-7,2'-(1',3'-dioxolane)];
(1RS,2SR,3RS,6SR)- and (1RS,2RS,3SR,6SR)-spiro[2,3-epoxy-6-isopropyl-8-ethylbicyclo[4.2.0]octane-7,2'-(1',3'-dioxolane)];
1RS,2SR,3RS,6SR)- and (1RS,2RS,3SR,6SR)-spiro[2,3-epoxy-6-isopropyl-8-isobutylbicyclo[4.2.0]octane-7,2'-(1',3'-dioxolane)];
(1RS,2SR,3RS,6RS)- and (1RS,2RS,3SR,6RS)-spiro[2,3-epoxy-6-n-hexyl-8-methylbicyclo[4.2.0]octane-7,2'-(1',3'-dioxolane]; and
(1RS,2SR,3RS,6RS)- and (1RS,2RS,3SR,6RS)-spiro[2,3-epoxy-6-n-hexyl-8-n-hexylbicyclo[4.2.0]octane-7,2'-(1',3'-dioxolane)].

PREPARATION 11

Preparation of a mixture of (3'S,
1R,2S,3R,6S)-Spiro[2-(3'-t-butyldimethylsilyloxy-3'-
cyclohexylprop-1'-ynyl)-3-hydroxy-6-methylbicy-
clo[4.2.0]-octane-7,2"-(1",3"-dioxolane)] and
(3'S,1S,2R,3S,6R)-Spiro-[2-(3'-t-butyldimethylsilyloxy-
3'-cyclohexylprop-1'-ynyl)-3-hydroxy-6-methylbicy-
clo[4.2.0]-octane-7.2"-(1",3"-dioxolane)] and Related
Compounds of Formula (12) and (13).

A. To a mixture of 3.8 g of (S)-3-t-butyldimethyl-
silyloxy-3-cyclohexylprop-1-yne, for example prepared
according to Preparation 3, in 30 ml tetrahydrofuran at
0° C. under an argon atmosphere was added over 10
min 10.4 ml of 1.25M n-butyllithium in hexane to give
the lithium salt of formula B. The resulting solution was
cooled to −78° C. and a solution of 2.0 g of a mixture of
(1RS,2SR,3RS,6RS)-spiro-[2,3-epoxy-6-methylbicy-
clo[4.2.0]octane-7,2'-(1',3'-dioxolane)] and
(1RS,2RS,3SR,6RS)-spiro-[2,3-epoxy-6-methylbicy-
clo[4.2.0]octane-7,2'-(1',3'-dioxolane)], prepared as
shown in Preparation 10, in 25 ml tetrahydrofuran was
added. To this stirred mixture at −78° C. was added
1.35 ml of boron trifluoride etherate dropwise over a 15
minute period, stirred for 30 minutes, then 25 ml of
saturated sodium sulfate solution was added. The result-
ing mixture was warmed to room temperature and ex-
tracted thoroughly with ethyl acetate. This extract was
dried over sodium sulfate and concentrated in vacuo to
give 6 g of an oil. The oil was chromatographed on
silica gel eluting with 30% ether in hexane to give 3.5 g
of a mixture of (3'S,1R,2S,3R,6S)-spiro[2-(3'-t-butyl-
dimethylsilyloxy-3'-cyclohexylprop-1'-ynyl)-3-
hydroxy-6-methylbicyclo[4.2.0]octane-7,2"-(1",3"-
dioxolane)] and (3'S,1S,2R,3S,6R)-spiro[-2-(3'-t-butyl-
dimethylsilyloxy-3'-cyclohexylprop-1'-ynyl)-3-
hydroxy-6-methylbicyclo[4.2.0]octane-7,2"-(1",3"-
dioxolane)], the compounds of formula (12) and (13).

B. Similarly, starting with the appropriate mixture of
compounds of formula (10) and (11) in place of the
mixture of (1RS,2SR,3RS,6RS)-spiro[-2,3-epoxy-6-
methylbicyclo[4.2.0]octane-7,2'-(1',3'-dioxolane)] and
(1RS,2RS,3SR,6RS)-spiro-[-2,3-epoxy-6-methylbicy-
clo[4.2.0]octane-7,2'-(1',3'-dioxolane)] in paragraph A
above, and optionally replacing lithium (S)-3-t-butyl-
dimethylsilyloxy 3-cyclohexylprop-1-yne with the ap-
propriate compound of formula B, the following mix-
tures of compounds of formula (12) and (13) where Y is
hydrogen, or Y is lower alkyl (exo or endo, or a mixture
of both) are prepared:

(3'R,1R,2S,3R,6S)-spiro[2-(3'-t-butyldimethylsilyloxy-
3'-cyclohexylprop-1'-ynyl)-3-hydroxy-6 methylbicy-
clo[-4.2.0]octane 7,2"-(1",3"-dioxolane)]; and (3'R,1S,2R,3S,6R)-spiro[2-(3'-t-butyldimethylsilyloxy-
3'-cyclohexylprop-1'-ynyl)-3-hydroxy-6-methylbicy-
clo-[4.2.0]octane-7,2"-(1",3"-dioxolane)];

(3'S,1R,2S,3R,6S)-spiro[2-(3'-t-butyldimethylsilyloxy-
3'-cyclohexyl-3'-methylprop-1'-ynyl)-3-hydroxy- 6-
methylbicyclo[4.2.0]octane-7.2"-(1",3"-dioxolane)];
and (3'S,1S,2R,3S,6R)-spiro[2-(3'-t-butyldimethylsilyloxy-
3'-cyclohexyl-3'-methylprop-1'-ynyl)-3-hydroxy-6-
methylbicyclo[4.2.0]octane-7,2"-(1",3"-dioxolane)];

(3'S,1R,2S,3R,6S)-spiro[2-(3'-t-butyldimethylsilyloxy-
3'-cyclohexylprop-1-ynyl)-3-hydroxy-6-ethylbicy-
clo[4.2.0]octane-7,2"-(1",3"-dioxolane)]; and (3'S,1S,2R,3S,6R)-spiro[2-(3'-t-butyldimethylsilyloxy-
3'-cyclohexylprop-1'-ynyl)-3-hydroxy-6-ethylbicy-
clo[4.2.0]octane-7,2"-(1",3"-dioxolane)];

(3'R,1R,2S,3R,6S)-spiro[2-(3'-t-butyldimethylsilyloxy-
3'-cyclohexylprop-1'-ynyl)-3-hydroxy-6-ethylbicy-
clo[4.2.0]octane-7,2"-(1",3"-dioxolane)]; and (3'R,1S,2R,3S,6R)-spiro[2-(3'-t-butyldimethylsilyloxy-
3'-cyclohexylprop-1'-ynyl)-3-hydroxy-6-ethylbicy-
clo[4.2.0]octane-7,2"-(1",3"-dioxolane)];

(3'S,1R,2S,3R,6R)-spiro[2-(3'-t-butyldimethylsilyloxy-
3'-cyclohexylprop-1'-ynyl)-3-hydroxy-6-isopropyl-
bicyclo[4.2.0]octane-7,2"-(1",3"-dioxolane)]; and (3'S,1S,2R,3S,6S)-spiro[2-(3'-t-butyldimethylsilyloxy-
3'-cyclohexylprop-1'-ynyl)-3-hydroxy-6-isopropyl-
bicyclo[4.2.0]octane-7,2"-(1",3"-dioxolane)];

(3'S,1R,2S,3R,6S) spiro[2-(3'-t-butyldimethylsilyloxy-
3'-cyclohexylprop-1'-ynyl)-3-hydroxy-6-n-hexylbicy-
clo[4.2.0]octane-7,2"-(1",3"-dioxolane)]; and (3'S,1S,2R,3S,6R)-spiro[2-(3'-t-butyldimethylsilyloxy-
3'-cyclohexylprop-1'-ynyl)-3-hydroxy-6-n-hexylbicy-
clo[4.2.0]octane-7,2"-(1",3"-dioxolane)];

(3'S,1R,2S,3R,6S)-spiro[2-(3'-t-butyldimethylsilyloxy-
4'-cyclohexylbut-1'-ynyl)-3-hydroxy-6-methylbicy-
clo[4.2.0]octane-7,2"-(1",3"-dioxolane)]; and (3'S,1S,2R,3S,6R)-spiro[2-(3'-t-butyldimethylsilyloxy-
4'-cyclohexylbut-1'-ynyl)-3-hydroxy-6-methylbicy-
clo[4.2.0]octane-7,2"-(1",3"-dioxolane)];

(3'S,1R,2S,3R,6S)-spiro[2-(3'-t-butyldimethylsilyloxy-
4'-cyclopentylbut- 1'-ynyl)-3-hydroxy-6-methylbicy-
clo[4.2.0]octane-7,2"-(1",3"-dioxolane)]; and (3'S,1S,2R,3S,6R) spiro[2-(3'-t-butyldimethylsilyloxy-
4'-cyclopentylbut-1'-ynyl)-3-hydroxy-6-methylbicy-
clo[4.2.0]octane-7,2"-(1",3"-dioxolane)];

(3'S,1R,2S,3R,6S)-spiro[2-(3'-t-butyldimethylsilyloxy-
dec-1'-ynyl)-3-hydroxy-6-methylbicyclo[4.2.0]oct-
2-ene-7,2"-(1",3"-dioxolane)]; and (3'S,1S,2R,3S,6R)-spiro[2-(3'-t-butyldimethylsilyloxy-
dec-1'-ynyl)-3-hydroxy-6-methylbicyclo[4.2.0]oct-
2-ene-7,2"-(1",3"-dioxolane)];

(3'S,1R,2S,3R,6S)-spiro[2-(3'-t-butyldimethylsilyloxy-
4'-phenoxybut-1'-ynyl)-3-hydroxy-6-methylbicy-
clo[4.2.0]octane-7,2"-(1",3"-dioxolane)]; and (3'S,1S,2R,3S,6R)-spiro[2-(3'-t-butyldimethylsilyloxy-
4'-phenoxybut-1'-ynyl)-3-hydroxy-6-methylbicy-
clo[4.2.0]octane-7,2"-(1",3"-dioxolane)];

(3'S,1R,2S,3R,6S)-spiro[2-(3'-t-butyldimethylsilyloxy-
4'-(endo-bicyclo3.1.0]hex-6-yl)but-1'-ynyl)-3-
hydroxy-6-methylbicyclo[4.2.0]octane-7,2"(1",3"-
dioxolane)]; and (3'S,1S,2R,3S,6R)-spiro[2-(3'-t-butyldimethylsilyloxy-
4'-(endobicyclo[3.1.0]hex-6-yl)but-1'-ynyl)-3-
hydroxy-6-methylbicyclo[4.2.0]octane-7,2"-(1",3"-
dioxolane)];

(3'S,1S,2S,3R,6S)-spiro[2-(3'-t-butyldimethylsilyloxy-
3'-cyclohexylprop-1'-ynyl)-3-hydroxy-6,8-dimethyl-
bicyclo[4.2.0]octane-7,2"-(1",3"-dioxolane)]; and (3'S,1R,2R,3S,6R)-spiro[2-(3'-t-butyldimethylsilyloxy-
3'-cyclohexylprop-1'-ynyl)-3-hydroxy-6,8-dimethyl-
bicyclo[4.2.0]octane-7,2"-(1",3"-dioxolane)];

(3'R,1S,2S,3R,6S)-spiro[2-(3'-t-butyldimethylsilyloxy-
3'-cyclohexylprop-1'-ynyl)-3-hydroxy-6,8-dimethyl-
bicyclo[4.2.0]octane-7,2"-(1",3"-dioxolane)]; and (3'R,1R,2R,3S,6R)-spiro[2-(3'-t-butyldimethylsilyloxy-
3'-cyclohexylprop- 1'-ynyl)-3-hydroxy-6,8-diemthyl-
bicyclo[4.2.0]octane-7,2"-(1",3"-dioxolane)];

(3'S,1S,2S,3R,6S)-spiro[2-(3'-t-butyldimethylsilyloxy-
4'-cyclohexylbut-1'-ynyl)-3-hydroxy-6,8-dimethyl-
bicyclo[4.2.0]octane-7,2"-(1",3"-dioxolane)]; and (3'S,1R,2R,3S,6R)-spiro[2-(3'-t-butyldimethylsilyloxy-4'-cyclohexylbut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-4'-cyclopentylbut-1'-ynyl)-3-hydroxy-6,8-dimethylbicyclo[4.2.0]octane-7,2''-(1'',3''-dioxolane)]; and (3'S,1R,2R,3S,6R)-spiro[2-(3'-t-butyldimethylsilyloxy-4'-cyclopentylbut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-dec-1'-ynyl)-3-hydroxy-6,8-dimethylbicyclo[4.2.0]octane-7,2''-(1'',3''-dioxolane)]; and (3'S,1R,2R,3S,6R)-spiro[2-(3'-t-butyldimethylsilyloxy-dec-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-4'-phenoxybut-1'-ynyl)-3-hydroxy-6,8-dimethylbicyclo[4.2.0]octane-7,2''-(1'',3''-dioxolane)]; and (3'S,1R,2R,3S,6R)-spiro[2-(3'-t-butyldimethylsilyloxy-4'-phenoxybut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl) 3-hydroxy-6-methyl-8ethylbicyclo[4.2.0]octane-7,2''-(1'',3''-dioxolane)]; and (3'S,1R,2R,3S,6R)-spiro[2-(3'-t-butyldimethylsilyloxy-3'-cyclohexylprop-1'-ynyl)-3-hydroxy-6-methyl-8ethylbicyclo[4.2.0]octane-7,2''-(1'',3''-dioxolane)];

(3'S,1S,2S,3R,6S)-spiro[2-(3'-t-butyldimethylsilyloxy-4'-cyclohexylbut-1'-ynyl)-3-hydroxy-6-methyl-8-ethylbicyclo[4.2.0]octane-7,2''-(1'',3''-dioxolane)]; and (3'S,1R,2R,3S,6R)-spiro[2-(3'-t-butyldimethylsilyloxy-4'-cyclohexylbut-1'-ynyl)-3-hydroxy-6-methyl-8-ethylbicyclo[4.2.0]octane-7,2''-(1'',3''-dioxolane)];

(3'S,1S,2S,3R,6S) spiro[2-(3'-t-butyldimethylsilyloxy-dec-1'-ynyl)-3-hydroxy-6-methyl-8-ethylbicyclo[4.2.0]octane-7,2''-(1'',3''-dioxolane)]; and (3'S,1R,2R,3S,6R)-spiro[2-(3'-t-butyldimethylsilyloxy-dec-1'-ynyl)-3-hydroxy-6-methyl-8-ethylbicyclo[4.2.0]octane-7,2''-(1'',3''-dioxolane)];

(3'S,1S,2S,3R,6S) spiro[2-(3'-t-butyldimethylsilyloxy-4'-phenoxybut-1'-ynyl)-3-hydroxy-6-methyl-8ethylbicyclo[4.2.0]octane-7,2''-(1'',3''-dioxolane)]; and (3'S,1R,2R,3S,6R)-spiro[2-(3'-t-butyldimethylsilyloxy-4'-phenoxybut-1'-ynyl)-3-hydroxy-6-methyl-8-ethylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6-methyl-8isobutylbicyclo[4.2.0]octane-7,2''-(1'',3''-dioxolane)]and;

(3'S,1R,2R,3S,6R)-spiro[2-(3'-t-butyldimethylsilyloxy-3'-cyclohexylprop-1'-ynyl)-3-hydroxy-6-methyl-8-isobutylbicyclo[4.2.0]octane-7,2''-(1'',3''-dioxolane)];

(3'S,1S,2S,3R,6S) spiro[2-(3'-t-butyldimethylsilyloxy-3'-cyclohexylprop-1'-ynyl)-3-hydroxy-6-methyl-8-n-hexylbicyclo[4.2.0]octane-7,2''-(1'',3''-dioxolane)]: and (3'S,1R,2R,3S,6R)-spiro[2-(3'-t-butyldimethylsilyloxy-3'-cyclohexylprop-1'-ynyl)-3-hydroxy-6-methyl-8-n-hexylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6-ethyl-8-methylbicyclo[4.2.0]octane-7,2''-(1'',3''-dioxolane)]; and (3'S,1R,2R,3S,6R)-spiro[2-(3'-t-butyldimethylsilyloxy-3'-cyclohexylprop-1'-ynyl)-3-hydroxy-6-ethyl-8methylbicyclo[4.2 0]octane-7,2''-(1'',3''-dicxolane)];

(3'S,1S,2S,3R,6S)-spiro[2-(3'-t-butyldimethylsilyloxy-3'-cyclohexylprop-1'-ynyl)-3-hydroxy-6,8-diethylbicyclo[4.2.0]octane-7,2''-(1'',3''-dioxolane)]; and (3'S,1R,2R,3S,6R)-spiro[2-(3'-t-butyldimethylsilyloxy-3'-cyclohexylprop-1'-ynyl)-3-hydroxy-6,8-diethylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6-ethyl-8-isobutylbicyclo[4.2.0]octane-7,2''-(1'',3''-dioxolane)]; and (3'S,1R,2R,3S,6R)-spiro[2-(3'-t-butyldimethylsilyloxy-3'-cyclohexylprop-1'-ynyl)-3-hydroxy-6-ethyl-8isobutylbicyclo[4.2.0]octane-7,2''-(1'',3''-dioxolane)];

(3'S,1S,2S,3R,6R)-spiro[2-(3'-t-butyldimethylsilyloxy-3'-cyclohexylprop-1'-ynyl)-3-hydroxy-6-isopropyl-8-methylbicyclo[4.2.0]octane-7,2''-(1'',3''-dioxolane)]; and (3'S,1R,2R,3S,6S)-spiro[2-(3'-t-butyldimethylsilyloxy-3'-cyclohexylprop-1'-ynyl)-3-hydroxy-6-isopropyl-8-methylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6-isopropyl-8-ethylbicyclo[4.2.0]octane-7,2''-(1'',3''-dioxolane)]; and (3'S,1R,2R,3S,6S)-spiro[2-(3'-t-butyldimethylsilyloxy-3'-cyclohexylprop-1'-ynyl)-3-hydroxy-6-isopropyl-8-ethylbicyclo[4.2.0]octane-7,2''-(1'',3''-dioxolane)];

(3'S,1S,2S,3R,6R)-spiro[2-(3'-t-butyldimethylsilyloxy-3'-cyclohexylprop-1'-ynyl)-3-hydroxy-6-isopropyl-8-isobutylbicyclo[4.2.0]octane-7,2''-(1'',3''-dioxolane)]; and (3'S,1R,2R,3S,6S)-spiro[2-(3'-t-butyldimethylsilyloxy-3'-cyclohexylprop-1'-ynyl)-3-hydroxy-6-isopropyl-8-isobutylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6-n-hexyl-8methylbicyclo[4.2.0]octane-7,2''-(1'',3''-dioxolane)]; and (3'S,1R,2R,3S,6R)-spiro[2-(3'-t-butyldimethylsilyloxy-3'-cyclohexylprop-1'-ynyl)-3-hydroxy-6-n-hexyl-8-methylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6-n-hexyl-8-n-hexylbicyclo[4.2.0]octane-7,2''-(1'',3''-dioxolane)]; and (3'S,1R,2R,3S,6R)-spiro[2-(3'-t-butyldimethylsilyloxy-3'-cyclohexylprop-1'-ynyl)-3-hydroxy 6-n-hexyl-8-n-hexylbicyclo[4.2.0]octane 7,2''-(1'',3''-dioxolane)].

PREPARATION 12

Separation of a mixture of (3'S, 1R,2S,3R,6S) Spiro[2-(3'-t-butyldimethylsilyloxy-3'-cyclohexylprop-1'-ynyl)-3-hydroxy-6-methylbicyclo[4.2.0]-octane-7,2''-(1'',3''-dioxolane)] and (3'S,1S,2R,3S,6R)-Spiro[2-(3'-t-butyldimethylsilyloxy-3'-cyclohexylprop-1'-ynyl)-3-hydroxy-6-methylbicyclo[4.2.0]octane-7.2''-(1'',3''-dioxolane)] and Related Mixtures of the Compounds of the Formula (12) and (13).

A. To a mixture of 5.4 g of the diastereomeric mixture of the above title compounds (a mixture of the compounds of formula (12) and (13)), prepared as shown in Preparation 11, in 200 ml diethyl ether was added 5.0 g of dicobalt octacarbonyl. The resulting solution was stirred at 23° C. for 1 hour. The mixture was diluted with 200 ml of diethyl ether and the resulting solution was filtered through 100 g of silica gel. The filtrate was concentrated to an oil which was purified by flash chromatography using 10% ethyl acetate - hexane to give two components: A (high R$_f$) and B (low R$_f$). Component A (3.6 g) was dissolved in 200 ml acetone - water (9:1), to which was added 13 g cerium ammonium nitrate. After 2 min. this mixture was diluted with 300 ml water. The product was isolated by extraction with ethyl acetate. After drying and evaporation there was obtained an oil, which was chromtographed on silica gel, eluting with 25% ethyl acetate in hexane, to give 1.8 g of (3'S,1R,2S,3R,6S)-spiro[2-(3'-t-butyldimethylsilyloxy-3'-cyclohexylprop-1'-ynyl)-3-hydroxy-6-methylbicyclo[4.2.0]octane-7,2''-(1'',3''-dioxolane)]. Similarly component B (4.2 g) was converted to 2.2 g of (3'S,1S,2R,3S,6R)-Spiro[2-(3'-t-butyldimethylsilyloxy-3'-cyclohexylprop-1'-ynyl)-3-hydroxy-6-methylbicyclo[4.2.0]octane-7,2''-(1'',3''-dioxolane)] as an oil.

B. Similarly, starting with the appropriate mixture of compounds of formula (12) and (13) in place of the mixture in paragraph A above, the following mixtures of compounds of formula (12) and (13) where Y is hydrogen, or Y is lower alkyl (exo or endo, or a mixture of both) are separated into the individual compounds of formula (12) and (13):

(3'R,1R,2S,3R,6S)-spiro[2-(3'-t-butyldimethylsilyloxy-3'-cyclohexylprop-1'-ynyl)-3-hydroxy-6-methylbicyclo[4.2.0]octane-7,2''-(1'',3''-dioxolane)];

(3'R,1S,2R,3S,6R)-spiro[2-(3'-t-butyldimethylsilyloxy-3'-cyclohexylprop-1'-ynyl)-3-hydroxy-6-methylbicyclo-[4.2.0]octane-7,2''-(1'',3''-dioxolane)];

(3'S,1R,2S,3R,6S)-spiro[2-(3'-t-butyldimethylsilyloxy-3'-cyclohexyl-3'-methylprop-1'-ynyl)-3-hydroxy-6-methylbicyclo[4.2.0]octane-7,2''-(1'',3''-dioxolane)];

(3'S,1S,2R,3S,6R)-spiro[2-(3'-t-butyldimethylsilyloxy-3'-cyclohexyl-3'-methylprop-1'-ynyl)-3-hydroxy-6-methylbicyclo[4.2.0]octane-7,2''-(1'',3''-dioxolane)];

(3'S,1R,2S,3R,6S)-spiro[2-(3'-t-butyldimethylsilyloxy-3'-cyclohexylprop-1'-ynyl)-3-hydroxy-6-ethylbicyclo[4.2.0]octane-7,2''-(1'',3''-dioxolane)];

(3'S,1S,2R,3S,6R)-spiro[2-(3'-t-butyldimethylsilyloxy-3'-cyclohexylprop-1'-ynyl)-3-hydroxy-6-ethylbicyclo[4.2.0]octane-7,2''-(1'',3''-dioxolane)];

(3'S,1R,2S,3R,6R)-spiro[2-(3'-t-butyldimethylsilyloxy-3'-cyclohexylprop-1'-ynyl)-3-hydroxy-6-isopropylbicyclo[4.2.0]octane-7,2''-(1'',3''-dioxolane)];

(3'S,1S,2R,3S,6S)-spiro[2-(3'-t-butyldimethylsilyloxy-3'-cyclohexylprop-1'-ynyl)-3-hydroxy-6-isopropylbicyclo[4.2.0]octane-7,2''-(1'',3''-dioxolane)];

(3'S,1R,2S,3R,6S)-spiro[2-(3'-t-butyldimethylsilyloxy-3'-cyclohexylprop-1'-ynyl)-3-hydroxy-6-n-hexylbicyclo[4.2.0]octane-7,2''-(1'',3''-dioxolane)];

(3'S,1S,2R,3S,6R)-spiro[2-(3'-t-butyldimethylsilyloxy-3'-cyclohexylprop-1'-ynyl)-3-hydroxy-6-n-hexylbicyclo[4.2.0]octane-7,2''-(1'',3''-dioxolane)];

(3'S,1R,2S,3R,6S)-spiro[2-(3'-t-butyldimethylsilyloxy-4'-cyclohexylbut-1'-ynyl)-3-hydroxy-6-methylbicyclo[4.2.0]octane-7,2''-(1'',3''-dioxolane)];

(3'S,1S,2R,3S,6R)-spiro[2-(3'-t-butyldimethylsilyloxy-4'-cyclohexylbut-1'-ynyl)-3-hydroxy-6-methylbicyclo[4.2.0]octane-7,2''-(1'',3''-dioxolane)];

(3'S,1R,2S,3R,6S)-spiro[2-(3'-t-butyldimethylsilyloxy-4'-cyclopentylbut-1'-ynyl)-3-hydroxy-6-methylbicyclo[4.2.0]octane-7,2''-(1'',3''-dioxolane)];

(3'S,1S,2R,3S,6R)-spiro[2-(3'-t-butyldimethylsilyloxy-4'-cyclopentylbut-1'-ynyl)-3-hydroxy-6-methylbicyclo[4.2.0]octane-7,2''-(1'',3''-dioxolane)];

(3'S,1R,2S,3R,6S)-spiro[2-(3'-t-butyldimethylsilyloxy-dec-1'-ynyl)-3-hydroxy-6-methylbicyclo[4.2.0]oct-2-ene-7,2''-(1'',3''-dioxolane)];

(3'S,1S,2R,3S,6R)-spiro[2-(3'-t-butyldimethylsilyloxy-dec-1'-ynyl)-3-hydroxy6-methylbicyclo[4.2.0]oct-2-ene-7,2''-(1'',3''-dioxolane)];

(3'S,1R,2S,3R,6S)-spiro[2-(3'-t-butyldimethylsilyloxy-4'-phenoxybut-1'-ynyl)-3-hydroxy-6-methylbicyclo[4.2.0]octane-7,2''-(1'',3''-dioxolane)];

(3'S,1S,2R,3S,6R)-spiro[2-(3'-t-butyldimethylsilyloxy-4'-phenoxybut-1'-ynyl)-3-hydroxy-6-methylbicyclo[4.2.0]octane-7,2''-(1'',3''-dioxolane)];

(3'S,1R,2S,3R,6S)-spiro[2-(3'-t-butyldimethylsilyloxy-4'-(endo-bicyclo[3.1.0]hex-6-yl)but-1'-ynyl)-3-hydroxy-6-methylbicyclo[4.2.0]octane-7,2''-(1'',3''-dioxolane)];

(3'S,1S,2R,3S,6R)-spiro[2-(3'-t-butyldimethylsilyloxy-4'-(endo-bicyclo[3.1.0]hex-6-yl)but-1'-ynyl)-3-hydroxy-6-methylbicyclo[4.2.0]octane-7,2''-(1'',3''-dioxolane)];

(3'S,1S,2S,3R,6S)-spiro[2-(3'-t-butyldimethylsilyloxy-3'-cyclohexylprop-1'-ynyl)-3-hydroxy-6,8-dimethylbicyclo[4.2.0]octane-7,2''-(1'',3''-dioxolane)];

(3'S,1R,2R,3S,6R)-spiro[2-(3'-t-butyldimethylsilyloxy-3'-cyclohexylprop-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-4'-cyclohexylbut-1'-ynyl)-3-hydroxy-6,8-dimethylbicyclo[4.2.0]octane-7,2''-(1'',3''-dioxolane)];

(3'S,1R,2R,3S,6R)-spiro[2-(3'-t-butyldimethylsilyloxy-4'-cyclohexylbut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-4'-cyclopentylbut-1'-ynyl)-3-hydroxy-6,8-dimethylbicyclo[4.2.0]octane-7,2''-(1'',3''-dioxolane)];

(3'S,1R,2R,3S,6R)-spiro[2-(3'-t-butyldimethylsilyloxy-4'-cyclopentylbut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-dec-1'-ynyl)-3-hydroxy-6,8-dimethylbicyclo[4.2.0]octane-7,2''-(1'',3''-dioxolane)];

(3'S,1R,2R,3S,6R)-spiro[2-(3'-t-butyldimethylsilyloxy-dec-1'-ynyl)-3-hydroxy-6,8-dimethylbicyclo[4.2.0]octane-7,2''-(1'',3''-dioxolane)];

(3'S,1S,2S,3R,6S)-spiro[2-(3'-t-butyldimethylsilyloxy-4'-phenoxybut-1'-ynyl)-3-hydroxy-6,8-dimethylbicyclo[4.2.0]octane-7,2''-(1'',3''-dioxolane)];

(3'S,1R,2R,3S,6R)-spiro[2-(3'-t-butyldimethyl-silyloxy-4'-phenoxybut-1'-ynyl)-3-hydroxy-6,8-dimethylbicyclo[4.2.0]octane-7,2''-(1'',3''-dioxolane)];

(3'S,1S,2S,3R,6S)-spiro[2-(3't-butyldimethyl-silyloxy-3'-cyclohexylprop-1'-ynyl) 3-hydroxy 6-methyl-8-ethylbicyclo[4.2.0]octane-7,2''(1'',3''-dioxolane)];

(3'S,1R,2R,3S,6R) spiro[2-(3'-t-butyldimethylsilyloxy-3'-cyclohexylprop-1'-ynyl)-3-hydroxy-6-methyl-8ethylbicyclo[4.2.0]octane 7,2''-(1'',3''-dioxolane)];

(3'S,1S,2S,3R,6S)-spiro[2-(3'-t-butyldimethylsilyloxy-4'-cyclohexylbut-1'-ynyl)-3-hydroxy-6-methyl-8ethylbicyclo-[4.2.0]octane-7,2''-(1'',3''-dioxolane)];

(3'S,1R,2R,3S,6R)-spiro[2-(3'-t-butyldimethylsilyloxy-4'-cyclohexylbut-1'-ynyl)-3-hydroxy-6-methyl-8-ethylbicyclo[4.2.0]octane-7,2''-(1'',3''-dioxolane)];

(3'S,1S,2S,3R,6S)-spiro[2-(3'-t-butyldimethylsilyloxy-dec-1'-ynyl) 3-hydroxy-6-methyl-8-ethylbicyclo-[4.2.0]octane-7,2''-(1'',3''-dioxolane)];

(3'S,1R,2R,3S,6R)-spiro[2-(3'-t-butyldimethylsilyloxy-dec-1'-ynyl) 3-hydroxy-6-methyl-8-ethylbicyclo-[4.2.0]octane-7,2''-(1'',3''-dioxolane)];

(3'S,1S,2S,3R,6S)-spiro[2-(3'-t-butyldimethylphenox-
 ybut-1'-ynyl)-3-hydroxy-6-methyl-8-ethylbicy-
 clo[4.2.0]octane-7,2''-(1'',3''-dioxolane)];
(3'S,1R,2R,3S,6R)-spiro[2-(3'-t-butyldimethylsilyloxy-
 4'-phenoxybut-1'-ynyl)-3-hydroxy 6-methyl-8-ethyl-
 bicyclo[4.2.0]octane-7,2''-(1'',3''-dioxolane)];
(3'S,1S,2S,3R,6S) spiro[2-(3'-t-butyldimethylsiloxy-3'-
 cyclohexylprop-1'-ynyl)-3-hydroxy-6-methyl-8-
 isobutylbicyclo[4.2.0]octane-7,2''-1'',3''-dioxolane)];
(3'S,1R,2R,3S,6R)-spiro[2-(3,-t-butyldimethyl-silyloxy-
 cyclohexylprop-1'-ynyl)-3-hydroxy-6-methyl-8-n-
 hexylbicyclo[4.2.0]octane-7,2''-(1'',3''-dioxolane)];
(3'S,1R,2R,3S,6R)-spiro[2-(3'-t-butyldimethylsilyloxy-
 3'-cyclohexylprop-1'-ynyl)-3-hydroxy-6-methyl-8-n-
 hexylbicyclo[4.2.0]octane-7,2''-(1'',3''-dioxolane)];
(3'S,1S,2S,3R,6S)-spiro[2-(3'-t-butyldimethylsilyloxy-
 3'-cyclohexylprop-1'-ynyl)-3-hydroxy-6ethyl-8-
 methylbicyclo[4.2.0]octane-7,2''-(1'',3''-dioxolane)];
(3'S,1R,2R,3S,6R)-spiro[2-(3'-t-butyldimethyl-silyloxy-
 3'-cyclohexylprop-1'-ynyl)-3-hydroxy-6-ethyl-8-
 methylbicyclo[4.2.0]octane-7,2''-(1'',3''-dioxolane)];
(3'S,1S,2S,3R,6S)-spiro[2-(3'-t-butyldimethylsilyloxy-
 3'-cyclohexylprop-1'-ynyl)-3-hydroxy-6,8-diethyl-
 bicyclo[4.2.0]octane-7,2''-(1'',3''-dioxolane)];
(3'S,1R,2R,3S,6R)-spiro[2-(3'-t-butyldimethylsilyloxy-
 3'-cyclohexylprop-1'-ynyl)-3-hydroxy-6,8-diethyl-
 bicyclo[4.2.0]octane-7,2''-(1'',3''-dioxolane)];
(3'S,1S,2S,3R,6S)-spiro[2-(3'-t-butyldimethylsilyloxy-
 3'-cyclohexylprop-1'-ynyl)-3-hydroxy-6-ethyl-8-
 isobutylbicyclo[4.2.0]octane-7,2''-(1'',3''-dioxolane];
(3'S,1R,2R,3S,6R)-spiro[2-(3'-t-butyldimethylsilyloxy-
 3'-cyclohexylprop-1'-ynyl)-3-hydroxy-6-ethyl-8-
 isobutylbicyclo[4.2.0]octane-7,2''-(1'',3''-dioxolane)];
(3'S,1S,2S,3R,6R)-spiro[2-(3'-t-butyldimethylsilyloxy-
 3'-cyclohexylprop-1'-ynyl)-3-hydroxy-6-isopropyl-8-
 methylbicyclo[4.2.0]octane-7,2''-(1'',3''-dioxolane)];
(3'S,1R,2R,3S,6S)-spiro[2-(3'-t-butyldimethylsilyloxy-
 3'-cyclohexylprop-1'-ynyl)-3-hydroxy-6-isopropyl-8-
 methylbicyclo[4.2.0]octane-7,2''-(1'',3''-dioxolane)];
(3'S,1S,2S,3R,6R)-spiro[2-(3'-t-butyldimethylsilyloxy-
 3'-cyclohexylprop-1'-ynyl)-3-hydroxy-6-isopropyl-8-
 ethylbicyclo[4.2.0]octane-7,2''-(1'',3''-dioxolane)];
(3'S,1R,2R,3S,6S)-spiro[2-(3'-t-butyldimethylsilyloxy-
 3'-cyclohexylprop-1'-ynyl)-3-hydroxy-6-isopropyl-8-
 ethylbicyclo[4.2.0]octane-7,2''-(1'',3''-dioxolane)];
(3'S,1S,2S,3R,6R)-spiro[2-(3'-t-butyldimethylsilyloxy-
 3'-cyclohexylprop-1'-ynyl)-3-hydroxy-6-isopropyl-8-
 isobutylbicyclo[4.2.0]octane-7,2''-(1'',3''-dioxolane)];
(3'S,1R,2R,3S,6S)-spiro[2-(3'-t-butyldimethylsilyloxy-
 3'-cyclohexylprop-1'-ynyl)-3-hydroxy-6-isopropyl-8-
 isobutylbicyclo[4.2.0]octane-7,2''-(1'',3''-dioxolane)];
(3'S,1S,2S,3R,6S)-spiro[2-(3'-t-butyldimethylsilyloxy-
 3'-cyclohexylprop-1'-ynyl)-3-hydroxy-6-n-hexyl-8-
 methylbicyclo[4.2.0]octane-7,2''-(1'',3''-dioxolane)];
(3''S,1R,2R,3S,6R)-spiro[2-(3'-t-butyldimethylsilyloxy-
 3'-cyclohexylprop-1'-ynyl)-3-hydroxy-6-n-hexyl-8-
 methylbicyclo[4.2.0]octane-7,2''-(1'',3''-dioxolane)];
(3'S,1S,2S,3R,6S)-spiro[2-(3'-t-butyldimethylsilyloxy-
 3'-cyclohexylprop-1'-ynyl)-3-hydroxy-6-n-hexyl-8-n-
 hexylbicyclo[4.2.0]octane-7,2''-(1'',3''-dioxolane)];
 and
(3'S,1R,2R,3S,6R)-spiro[2-(3'-t-butyldimethylsilyloxy-
 3'-cyclohexylprop-1'-ynyl)-3-hydroxy-6-n-hexyl-8-n-
 hexylbicyclo[4.2.0]octane-7,2''-(1'',3''-dioxolane)].

C. If in Preparation 11 the chiral lithium salt of (S)-3-t-butyldimethylsilyloxy-3-cyclohexylprop-1-yne is replaced with a racemic compound of formula B, i.e. prepared from a racemic acetylenic alcohol, the subsequent cobalt separation set forth in Preparation 12 will yield racemic compounds rather than optically pure compounds. For example:

(3'SR,1RS,2SR,3RS,6SR)-spiro[2-(3'-t-butyldimethyl-
 silyloxy-3'-cyclohexylprop-1'-ynyl)-3-hydroxy-6-
 methylbicyclo[4.2.0]octane-7,2''-(1'',3''-dioxolane)];
(3'SR,1SR,2RS,3SR,6RS) Spiro[2-(3'-t-butyldimethyl-
 silyloxy-3'-cyclohexylprop-1'-ynyl)-3-hydroxy-6-
 methylbicyclo[4.2.0]octane-7,2''-(1'',3''-dioxolane)];
(3'SR,1RS,2SR,3RS,6SR)-spiro[2-(3'-,t-butyldimethyl-
 silyloxy-3'-cyclohexylprop-1'-ynyl)-3-hydroxy-6-
 ethylbicyclo[4.2.0]octane-7,2''(1'',3''-dioxolane)];
(3'SR,1SR,2RS,3SR,6RS)-spiro[2-(3'-t-butyldimethyl-
 silyloxy-3'-cyclohexylprop-1'-ynyl)-3-hydroxy-6-
 ethyl- bicyclo[4.2.0]octane-7,2''-(1'',3''-dioxolane)];
(3'SR,1SR,2SR,3RS,6SR)-spiro[2-(3'-t-butyldimethyl-
 silyloxy-3'-cyclohexylprop-1'-ynyl)-3-hydroxy-6-
 methyl-8-exo-methyl-bicyclo[4.2.0]octane-7,2''-
 (1'',3''-dioxolane)];
(3'SR,1RS,2RS,3SR,6RS)-spiro[2-(3'-t-butyldimethyl-
 silyloxy-3'-cyclohexylprop-1'-ynyl)-3-hydroxy-6-
 methyl-8-exo-methyl-bicyclo[4.2.0]octane-7,2''-
 (1'',3''-dioxolane)];
(3'SR,1SR,2SR,3RS,6SR)-spiro[2-(3'-t-butyldimethyl-
 silyloxy-3'-cyclohexylprop-1'-ynyl)-3-hydroxy-6-
 methyl-8-endo-methyl-bicyclo[4.2.0]octane-7,2''-
 (1'',3''-dioxolane)] and;
(3'SR,1RS,2RS,3SR,6RS)-spiro[2-(3'-t-butyldimethyl-
 silyloxy-3'-cyclohexylprop-1'-ynyl)-3-hydroxy-6-
 methyl-8-endo-methyl-bicyclo[4.2.0]octane-7,2''-
 (1'',3''-dioxolane)].

PREPARATION 13

Preparation of
(3'S,1S,2R,3S,6R)-2-(3'-hydroxy-3'-cyclohexylprop-1'-
ynyl)-3-hydroxy-6-methylbicyclo[4.2.0]octan-7-one and
Related Compounds of Formula (16) and (17).

A. A solution of 2.1 g of (3'S,1S,2R,3S,6R)-spiro[2-(3'-t-butyldimethylsilyloxy-3'-cyclohexylprop-1'-ynyl)-3-hydroxy-6-methylbicyclo[4.2.0]octane-7,2''-(1'',3''-dioxolane)], prepared as shown in Preparation 12, in 24 ml of acetonitrile and 12 ml of 1M sulfuric acid was stirred at 25° C. for 3 hours. The reaction was quenched by neutralization with aqueous sodium bicarbonate and the mixture was extracted with ethyl acetate. The extracts were dried with magnesium sulfate, evaporated to dryness and the residue was purified by short column silica gel chromatography. Elution with ethyl acetate hexane (1:1), gave 800 mg of (3'S,1S,2R,3S,6R)-2-(3'-hydroxy-3'-cyclohexylprop-1'-ynyl)-3-hydroxy-6-methylbicyclo[4.2.0]octan-7-one.

B. Similarly, starting with the appropriate individual compounds of formula (12) or (13) in place of (3'-S,1S,2R,3S,6R)-spiro[2-(3'-t-butyldimethylsilyloxy-3'-cyclohexylprop-1'-ynyl)-3-hydroxy-6-methylbicyclo[4.2.0]octane-7,2''-(1'',3''-dioxolane)] in paragraph A above, the following individual compounds of formula (16) or (17) where Y is hydrogen, or Y is lower alkyl (exo or endo, or a mixture of both) are obtained:

(3'R,1S,2R,3S,6R)-2-(3'-hydroxy-3'-cyclohexylprop-1'-
 ynyl)-3-hydroxy-6-methylbicyclo[4.2.0]oct-7-one;
(3'S,1S,2R,3S,6R)-2-(3'-hydroxy-3'-cyclohexyl-3'-
 methylprop-1'-ynyl)-3-hydroxy-6-methylbicy-
 clo[4.2.0]octan-7-one;
(3'S,1R,2S,3R,6S)-2-(3'-hydroxy-3'-cyclohexyl-3'-
 methylprop-1'-ynyl)-3-hydroxy-6-methylbicy-
 clo[4.2.0]octan-7-one;

(3'S,1R,2S,3R,6S)-2-(3'-hydroxy-3'-cyclohexylprop-1'-ynyl)-3-hydroxy-6-ethylbicyclo[4.2.0]octan-7-one;
(3'S,1S,2R,3S,6R)-2-(3'-hydroxy-3'-cyclohexylprop-1'-ynyl)-3-hydroxy-6-ethylbicyclo[4.2.0]octan-7-one;
(3'R,1S,2R,3S,6R)-2-(3'-hydroxy-3'-cyclohexylprop-1'-ynyl)-3-hydroxy-6-ethylbicyclo[4.2.0]octan-7-one;
(3'S,1R,2S,3R,6S)-2-(3'-hydroxy-3'-cyclohexylprop-1'-ynyl)-3-hydroxy-6-isopropylbicyclo[4.2.0]octan-7-one;
(3'S,1S,2R,3S,6R)-2-(3'-hydroxy-3'-cyclohexylprop-1'-ynyl)-3-hydroxy-6-isopropylbicyclo[4.2.0]octan-7-one;
(3'S,1R,2S,3R,6S)-2-(3'-hydroxy-3'-cyclohexylprop-1'-ynyl)-3-hydroxy-6-n-hexylbicyclo[4.2.0]octan-7-one;
(3'S,1S,2R,3S,6R)-2-(3'-hydroxy-3'-cyclohexylprop-1'-ynyl)-3-hydroxy-6-n-hexylbicyclo[4.2.0]octan-7-one;
(3'S,1R,2S,3R,6S)-2-(3'-hydroxy-4'-cyclohexylbut-1'-ynyl)-3-hydroxy-6-methylbicyclo[4.2.0]octan-7-one;
(3'S,1S,2R,3S,6R)-2-(3'-hydroxy-4'-cyclohexylbut-1'-ynyl)-3-hydroxy-6-methylbicyclo[4.2.0]octan-7-one;
(3'S,1R,2S,3R,6S)-2-(3'-hydroxy-4'-cyclopentylbut-1'-ynyl)-3-hydroxy-6-methylbicyclo[4.2.0]octan-7-one;
(3'S,1S,2R,3S,6R)-2-(3'-hydroxy-4'-cyclopentylbut-1'-ynyl)-3-hydroxy-6-methylbicyclo[4.2.0]octan-7-one;
(3'S,1R,2S,3R,6S)-2-(3'-hydroxydec 1'-ynyl)-3-hydroxy-6-methylbicyclo[4.2.0]octan-7-one;
(3'S,1S,2R,3S,6R)-2-(3'-hydroxydec-1'-ynyl)-3-hydroxy-6-methylbicyclo[4.2.0]octan-7-one;
(3'S,1R,2S,3R,6S) 2-(3'-hydroxy-4'-phenoxybut-1'-ynyl)-3-hydroxy-6-methylbicyclo[4.2.0]octan-7-one;
(3'S,1S,2R,3S,6R)-2-(3'-hydroxy-4'-phenoxybut-1'-ynyl)-3-hydroxy-6-methylbicyclo[4.2.0]octan-7-one;
(3'S,1R,2S,3R,6S)-2-(3'-hydroxy-4'-(endo-bicyclo[3.1.0]hex-6-yl)but-1'-ynyl)-3-hydroxy-6-methylbicyclo[4.2.0]octan-7-one;
(3'S,1S,2R,3S,6R)-2-(3'-hydroxy-4'-(endo-bicyclo[3.1.0]hex-6-yl)but-1'-ynyl)-3-hydroxy-6-methylbicyclo[4.2.0]octan-7-one;
(3'S,1S,2S,3R,6S)-2-(3'-hydroxy-3'-cyclohexylprop-1'-ynyl)-3-hydroxy-6,8-dimethyl-bicyclo[4.2.0]octan-7-one;
(3'S,1R,2S,3S,6R)-2-(3'-hydroxy-3'-cyclohexylprop-1'-ynyl)-3-hydroxy-6,8-dimethyl-bicyclo[4.2.0]octan-7-one;
(3'R,1R,2R,3S,6R)-2-(3'-hydroxy-3'-cyclohexylprop-1'-ynyl)-3-hydroxy-6,8-dimethyl-bicyclo[4.2.0]octan-7-one;
(3'S,1S,2S,3R,6S)-2-(3'-hydroxy-4'-cyclohexylbut-1'-ynyl)-3-hydroxy-6,8-dimethylbicyclo[4.2.0]octan-7-one;
(3'S,1R,2R,3S,6R)-2-(3'-hydroxy-4'-cyclohexylbut-1'-ynyl)-3-hydroxy-6,8-dimethylbicyclo[4.2.0]octan-7-one;
(3'S,1S,2S,3R,6S)-2-(3'-hydroxy-4'-cyclopentylbut-1'-ynyl)-3-hydroxy-6,8-dimethylbicyclo[4.2.0]octan-7-one;
(3'S,1R,2R,3S,6R)-2-(3'-hydroxy-4'-cyclopentylbut-1'-ynyl)-3-hydroxy-6,8-dimethylbicyclo[4.2.0]octan-7-one;
(3'S,1S,2S,3R,6S)-2-(3'-hydroxydec-1'-ynyl)-3-hydroxy-6,8-dimethylbicyclo[4.2.0]octan-7-one;
(3'S,1R,2R,3S,6R)-2-(3'-hydroxydec-1'-ynyl)-3-hydroxy-6,8-dimethylbicyclo[4.2.0]octan-7-one;
(3'S,1S,2S,3R,6S)-2-(3'-hydroxy-4'-phenoxybut-1'-ynyl)-3-hydroxy-6,8-dimethylbicyclo[4.2.0]octan-7-one;
(3'S,1R,2R,3S,6R)-2-(3'-hydroxy-4'-phenoxybut-1'-ynyl)-3-hydroxy-6,8-dimethylbicyclo[4.2.0]octan-7-one;
(3'S,1S,2S,3R,6S)-2-(3'-hydroxy-3'-cyclohexylprop-1'-ynyl)-3-hydroxy-6-methyl-8-ethylbicyclo[4.2.0]octan-7-one;
(3'S,1R,2R,3S,6R)-2-(3'-hydroxy-3'-cyclohexylprop-1'-ynyl)-3-hydroxy-6-methyl-8-ethylbicyclo[4.2.0]octan-7-one;
(3'S,1S,2S,3R,6S)-2-(3'-hydroxy-4'-cyclohexylbut-1'-ynyl)-3-hydroxy-6-methyl-8-ethylbicyclo[4.2.0]octan-7-one;
(3'S,1R,2R,3S,6R)-2-(3'-hydroxy-4'-cyclohexylbut-1'-ynyl)-3-hydroxy-6-methyl-8-ethylbicyclo[4.2.0]octan-7-one;
(3'S,1S,2S,3R,6S)-2-(3'-hydroxydec-1'-ynyl)-3-hydroxy-6-methyl-8-ethylbicyclo[4.2.0]octan-7-one;
(3'S,1R,2R,3S,6R)-2-(3'-hydroxydec-1'-ynyl)-3-hydroxy-6-methyl-8-ethylbicyclo[4.2.0]octan-7-one;
(3'S,1S,2S,3R,6S)-2-(3'-hydroxy-4'-phenoxybut-1'-ynyl)-3-hydroxy-6-methyl-8-ethylbicyclo[4.2.0]octan-7-one;
(3'S,1R,2R,3S,6R)-2-(3'-hydroxy-4'-phenoxybut-1'-ynyl)-3-hydroxy-6-methyl-8-ethylbicyclo[4.2.0]octan-7-one;
(3'S,1S,2S,3R,6S)-2-(3'-hydroxy-3'-cyclohexylprop-1'-ynyl)-3-hydroxy-6-methyl-8-isobutylbicyclo[4.2.0]octan-7-one;
(3'S,1R,2R,3S,6R)-2-(3'-hydroxy-3'-cyclohexylprop-1'-ynyl)-3-hydroxy-6-methyl-8-isobutylbicyclo[4.2.0]octan-7-one;
(3'S,1S,2S,3R,6S)-2-(3'-hydroxy-3'-cyclohexylprop-1'-ynyl)-3-hydroxy-6-methyl-8-n-hexylbicyclo[4.2.0]octan-7-one;
(3'S,1R,2R,3S,6R)-2-(3'-hydroxy-3'-cyclohexylprop-1'-ynyl)-3-hydroxy-6-methyl-8-n-hexylbicyclo[4.2.0]octan-7-one;
(3'S,1S,2S,3R,6S)-2-(3'-hydroxy-3'-cyclohexylprop-1'ynyl)-3-hydroxy-6-ethyl-8-methylbicyclo[4.2.0]octan-7-one;
(3'S,1R,2R,3S,6R)-2-(3'-hydroxy-3'-cyclohexylprop-1'-ynyl)-3-hydroxy-6-ethyl-8-methylbicyclo[4.2.0]octan-7-one;
(3'S,1S,2S,3R,6S)-2-(3'-hydroxy-3'-cyclohexylprop-1'-ynyl)-3-hydroxy-6,8-diethylbicyclo[4.2.0]octan-7-one;
(3'S,1R,2R,3S,6R)-2-(3'-hydroxy-3'-cyclohexylprop-1'-ynyl)-3-hydroxy-6,8-diethylbicyclo[4.2.0]octan-7-one;
(3'S,1S,2S,3R,6S)-2-(3'-hydroxy-3'-cyclohexylprop-1'-ynyl)-3-hydroxy-6-ethyl-8-isobutylbicyclo[4.2.0]octan-7-one;
(3'S,1R,2R,3S,6R)-2-(3'-hydroxy-3'-cyclohexylprop-1'-ynyl)-3-hydroxy-6-ethyl-8-isobutylbicyclo[4.2.0]octan-7-one;
(3'S,1S,2S,3R,6R)-2-(3'-hydroxy-3'-cyclohexylprop-1'-ynyl)-3-hydroxy-6-isopropyl-8-methylbicyclo[4.2.0]octan-7-one;
(3'S,1R,2R,3S,6S)-2-(3'-hydroxy-3'-cyclohexylprop-1'-ynyl)-3-hydroxy-6-isopropyl-8-methylbicyclo[4.2.0]octan-7-one;
(3'S,1S,2S,3R,6R)-2-(3'-hydroxy-3'-cyclohexylprop-1'-ynyl)-3-hydroxy-6-isopropyl-8-ethylbicyclo[4.2.0]octan-7-one;
(3'S,1R,2R,3S,6S)-2-(3'-hydroxy-3'-cyclohexylprop-1'-ynyl)-3-hydroxy-6-isopropyl-8-ethylbicyclo[4.2.0]octan-7-one;

(3'S,1S,2S,3R,6R)-2-(3'-hydroxy-3'-cyclohexylprop-1'-ynyl)-3-hydroxy-6-isopropyl-8-isobutylbicyclo[4.2.0]octan-7-one;

(3'S,1R,2R,3S,6S)-2-(3'-hydroxy-3'-cyclohexylprop-1'-ynyl)-3-hydroxy-6-isopropyl-8-isobutylbicyclo[4.2.0]octan-7-one;

(3'S,1S,2S,3R,6S)-2-(3'-hydroxy-3'-cyclohexylprop-1'-ynyl)-3-hydroxy-6-n-hexyl-8-methylbicyclo[4.2.0]octan-7-one;

(3'S,1R,2R,3S,6R)-2-(3'-hydroxy-3'-cyclohexylprop-1'-ynyl)-3-hydroxy-6-n hexyl-8-methylbicyclo[4.2.0]octan-7-one;

(3'S,1S,2S,3R,6S)-2-(3'-hydroxy-3'-cyclohexylprop-1'-ynyl)-3-hydroxy-6-n-hexyl-8-n-hexylbicyclo[4.2.0]octan-7-one; and (3'S,1R,2R,3S,6R)-2-(3'-hydroxy-3'-cyclohexylprop-1'-ynyl)-3-hydroxy-6-n-hexyl 8-n-hexylbicyclo[4.2.0]octan-7-one.

C. Similarly, starting with the appropriate racemic compounds of formula (dl 12) or (dl 13) in place of (3'S,1S,2R,3S,6R)-spiro[2-(3'-t-butyldimethylsilyloxy-3'-cyclohexylprop-1'-ynyl)-3-hydroxy-6-methylbicyclo[4.2.0]octane-7,2''-(1'',3''-dioxolane)] in paragraph A above, the preparation set forth in Preparation 13 will yield racemic compounds rather than optically pure compounds. For example:

(3'SR,1RS,2SR,3RS,6SR)-2-(3'-t-butyldimethylsilyloxy-3'-cyclohexylprop-1'-ynyl)-3-hydroxy-6-methylbicyclo[4.2.0]octan-7-one;

(3'SR,1SR,2RS,3SR,6RS)-Spiro[2-(3'-t-butyldimethylsilyloxy-3'-cyclohexylprop-1'-ynyl)-3-hydroxy-6-methylbicyclo[4.2.0]octan-7-one;

(3'SR,1RS,2SR,3RS,6SR)-2-(3'-t-butyldimethylsilyloxy-3'-cyclohexylprop-1'-ynyl)-3-hydroxy-6-ethylbicyclo[4.2.0]octan-7-one;

(3'SR,1SR,2RS,3SR,6RS)-2-(3'-t-butyldimethylsilyloxy-3'-cyclohexylprop-1'-ynyl)-3-hydroxy-6-ethylbicyclo[4.2.0]octan-7-one;

(3'SR,1SR,2SR,3RS,6SR)-2-(3'-t-butyldimethylsilyloxy-3'-cyclohexylprop-1'-ynyl)-3-hydroxy-6,8-dimethylbicyclo[4.2.0]octan-7-one; and (3'SR,1RS,2RS,3SR,6RS)-2-(3'-t-butyldimethylsilyloxy-3'-cyclohexylprop-1'-ynyl)-3-hydroxy-6,8-dimethylbicyclo[4.2.0]octan-7-one.

PREPARATION 14

A. Preparation of (3'S,1S,2R,3S,6R)-spiro-[2-(3'-hydroxy-3'-cyclohexylprop-1'-ynyl)-3-hydroxy-6-methylbicyclo[4.2.0]octane-7,2''-(1'',3''-dioxolane)] and Related Compounds of Formula (26)

To a solution of 4.7 g of (3'S,1S,2R,3S,6R)-spiro[2-(3'-t-butyldimethylsilyloxy-3'-cyclohexylprop-1'-ynyl)-3-hydroxy-6-methylbicyclo[4.2.0]octane-7,2''-(1'',3''-dixolane)], prepared as shown in Preparation 11, in 60 ml of tetrahydrofuran at 23° C. is added 25 ml of 1M tetrabutylammonium fluoride in tetrahydrofuran. The solution is stirred at room temperature for 5 hours, then 200 ml of water and 50 ml of saturated aqueous sodium bicarbonate is added. The mixture is extracted with ethyl acetate, the organic layer dried over sodium sulfate and the solvent removed under reduced pressure. The residue is chromatographed on silica gel, eluting with hexane ethyl acetate mixture (3:2), giving 3.25 g of (3'S,1S,2R,3S,6R)-spiro[2-(3'-hydroxy-3'-cyclohexylprop-1'-ynyl)-3-hydroxy-6-methylbicyclo[4.2.0]octane-7,2''-(1'',3''-dioxolane)].

B. Similarly, starting with the appropriate compound of formula (12) or (13) in place of (3'S,1S,2R,3S,6R)-spiro[2-(3'-t-butyldimethylsilyloxy-3'-cyclohexylprop-1'-ynyl)-3-hydroxy-6-methylbicyclo[4.2.0]octane-7,2''-(1'',3''-dixolane)] in paragraph A above, the following compound of formula (26) or (26A) where Y is hydrogen, or Y is lower alkyl (exo or endo, or a mixture of both) are prepared:

(3'S,1R,2S,3R,6S)-spiro[2-(3'-hydroxy-3'-cyclohexylprop-1'-ynyl)-3-hydroxy-6-ethylbicyclo[4.2.0]octane-7,2''-(1'',3''-dioxolane)];

(3'S,1S,2R,3S,6R)-spiro[2-(3'-hydroxy-3'-cyclohexylprop-1'-ynyl)-3-hydroxy-6-ethylbicyclo[4.2.0]octane-7,2''-(1'',3''-dioxolane)];

(3'S,1R,2S,3R,6R)-spiro[2-(3'-hydroxy-3'-cyclohexylprop-1'-ynyl)-3-hydroxy-6-isopropylbicyclo[4.2.0]octane-7,2''-(1'',3''-dioxolane)];

(3'S,1S,2R,3S,6S)-spiro[2-(3'-hydroxy-3'-cyclohexylprop-1'-ynyl)-3-hydroxy-6-isopropylbicyclo[4.2.0]octane-7,2''-(1'',3''-dioxolane)];

(3'S,1R,2S,3R,6S) spiro[2-(3'-hydroxy-3'-cyclohexylprop-1'-ynyl)-3-hydroxy-6-n-hexylbicyclo[4.2.0]octane-7,2''-(1'',3''-dioxolane)];

(3'S,1S,2R,3S,6R)-spiro[2-(3'-hydroxy-3'-cyclohexylprop-1'-ynyl)-3-hydroxy-6-n-hexylbicyclo[4.2.0]octane-7,2''-(1'',3''-dioxolane)];

(3'S,1R,2S,3R,6S) spiro[2-(3'-hydroxy-4'-cyclohexylbut-1'-ynyl)-3-hydroxy-6-methylbicyclo[4.2.0]octane-7,2''-(1'',3''-dioxolane)];

(3'S,1S,2R,3S,6R)-spiro[2-(3'-hydroxy-4'-cyclohexylbut-1'-ynyl)-3-hydroxy-6-methylbicyclo[4.2.0]octane-7,2''-(1'',3''-dioxolane)];

(3'S,1R,2S,3R,6S)-spiro[2-(3'-hydroxy-4'-cyclopentylbut-1'-ynyl)-3-hydroxy-6-methylbicyclo[4.2.0]octane-7,2''-(1'',3''-dioxolane)];

(3'S,1S,2R,3S,6R)-spiro[2-(3'-hydroxy-4'-cyclopentylbut-1'-ynyl)-3-hydroxy-6-methylbicyclo[4.2.0]octane-7,2''-(1'',3''-dioxolane)];

(3'S,1R,2S,3R,6S)-spiro[2-(3'-hydroxydec-1'-ynyl)-3-hydroxy-6-methylbicyclo[4.2.0]octane-7,2''-(1'',3''-dioxolane)];

(3'S,1S,2R,3S,6R)-spiro[2-(3'-hydroxydec-1'-ynyl)-3-hydroxy-6-methylbicyclo[4.2.0]octane-7,2''-(1'',3''-dioxolane)];

(3'S,1R,2S,3R,6S)-spiro[2-(3'-hydroxy-4'-phenoxybut-1'-ynyl)-3-hydroxy-6-methylbicyclo[4.2.0]octane-7,2''-(1'',3''-dioxolane)];

(3'S,1S,2R,3S,6R)-spiro[2-(3'-hydroxy-4'-phenoxybut-1'-ynyl)-3-hydroxy-6-methylbicyclo[4.2.0]octane-7,2''-(1'',3''-dioxolane)];

(3'S,1R,2S,3R,6S)-spiro[2-(3'-hydroxy-4'-(endobicyclo[3.1.0]hex-6-yl)but-1'-ynyl)-3-hydroxy-6-methylbicyclo[4.2.0]octane-7,2''-(1'',3''-dioxolane)];

(3'S,1S,2R,3S,6R)-spiro[2-(3'-hydroxy-4'-(endobicyclo[3.1.0]hex-6-yl)but-1'-ynyl)-3-hydroxy-6-methylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6,8-dimethylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6,8-dimethylbicyclo[4.2.0]octane-7,2''-(1'',3''-dioxolane)];

(3'S,1S,2S,3R,6S)-spiro[2-(3'-hydroxy-4'-cyclohexylbut-1'-ynyl)-3-hydroxy-6,8-dimethylbicyclo[4.2.0]octane-7,2''-(1'',3''-dioxolane)];

(3'S,1R,2R,3S,6R)-spiro[2-(3'-hydroxy-4'-cyclohexylbut-1'-ynyl)-3-hydroxy-6,8-dimethylbicyclo[4.2.0]octane-7,2''-(1'',3''-dioxolane)];

(3'S,1S,2S,3R,6S) spiro[2-(3'-hydroxy-4'-cyclopentylbut-1'-ynyl)-3-hydroxy-6,8-dimethylbicyclo[4.2.0]octane-7,2''-(1'',3''-dioxolane)];

(3'S,1R,2R,3S,6R)-spiro[2-(3'-hydroxy-4'-cyclopentylbut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-hydroxydec 1'-ynyl)-3-hydroxy-6,8-dimethylbicyclo[4.2.0]octane-7,2''-(1'',3''-dioxolane)];

(3'S,1R,2R,3S,6R)-spiro[2-(3'-hydroxydec 1'-ynyl)-3-hydroxy-6,8-dimethylbicyclo[4.2.0]octane-7,2''-(1'',3''-dioxolane)];

(3'S,1S,2S,3R,6S)-spiro[2-(3'-hydroxy-4'-phenoxybut-1'-ynyl)-3-hydroxy-6,8-dimethylbicyclo[4.2 0]octane-7,2''-(1'',3''-dioxolane)];

(3'S,1R,2R,3S,6R)-spiro[2-(3'-hydroxy-4'-phenoxybut-1'-ynyl)-3-hydroxy-6,8-dimethylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6-methyl-8-ethylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6-methyl-8-ethylbicyclo[4.2.0]octane-7,2''-(1'',3''-dioxolane)];

(3'S,1S,2S,3R,6S)-spiro[2-(3'-hydroxy-4'-cyclohexylbut-1'-ynyl)-3-hydroxy-6-methyl-8-ethylbicyclo[4.2.0]octane-7,2''-(1'',3''-dioxolane)];

(3'S,1R,2R,3S,6R)-spiro[2-(3'-hydroxy-4'-cyclohexylbut-1'-ynyl)-3-hydroxy-6-methyl-8-ethylbicyclo[4.2.0]octane-7,2''-(1'',3''-dioxolane)];

(3'S,1S,2S,3R,6S)-spiro[2-(3'-hydroxydec-1'-ynyl)-3-hydroxy-6-methyl-8-ethylbicyclo[4.2.0]octane-7,2''-(1'',3''-dioxolane)];

(3'S,1R,2R,3S,6R)-spiro[2-(3'-hydroxydec-1'-ynyl)-3-hydroxy-6-methyl-8-ethylbicyclo[4.2.0]octane-7,2''-(1'',3''-dioxolane)];

(3'S,1S,2S,3R,6S)-spiro[2-(3'-hydroxy-4'-phenoxybut-1'-ynyl)-3-hydroxy-6-methyl-8-ethylbicyclo[4.2.0]octane-7,2''-(1'',3''-dioxolane)];

(3'S,1R,2R,3S,6R)-spiro[2-(3'-hydroxy-4'-phenoxybut-1'-ynyl)-3-hydroxy-6-methyl-8-ethylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6-methyl-8-isobutylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6-methyl-8-isobutylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6-methyl-8-n-hexylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6-methyl-8-n-hexylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6-ethyl-8-methylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6-ethyl-8-methylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6,8-diethylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6,8-diethylbicyclo[4.2.0]octane-7,2''-(1'',3''-dioxolane)];

(3'S,1S,2S,3R,6S)-spiro[2-(3'-hydroxy-3'-cyclohexyprop-1'-ynyl)-3-hydroxy-6-ethyl-8-isobutylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6-ethyl-8-isobutylbicyclo[4.2.0]octane-7,2''-(1'',3''-dioxolane)];

(3'S,1S,2S,3R,6R)-spiro[2-(3'-hydroxy-3'-cyclohexylprop-1'-ynyl)-3-hydroxy-6-isopropyl-8-methylbicyclo[4.2.0]octane-7,2''-(1'',3''-dioxolane)];

(3'S,1R,2R,3S,6S)-spiro[2-(3'-hydroxy-3'-cyclohexylprop-1'-ynyl)-3-hydroxy-6-isopropyl-8-methylbicyclo[4.2.0]octane-7,2''-(1'',3''-dioxolane)];

(3'S,1S,2S,3R,6R)-spiro[2-(3'-hydroxy-3'-cyclohexylprop-1'-ynyl)-3-hydroxy-6-isopropyl-8-ethylbicyclo[4.2.0]octane-7,2''-(1'',3''-dioxolane)];

(3'S,1R,2R,3S,6S) spiro[2-(3'-hydroxy-3'-cyclohexylprop-1'-ynyl)-3-hydroxy-6-isopropyl-8-ethylbicyclo[4.2.0]octane-7,2''-(1'',3''-dioxolane)];

(3'S,1S,2S,3R,6R)-spiro[2-(3'-hydroxy-3'-cyclohexylprop-1'-ynyl)-3-hydroxy-6-isopropyl-8-isobutylbicyclo[4.2.0]octane-7,2''-(1'',3''-dioxolane)];

(3'S,1R,2R,3S,6S) spiro[2-(3'-hydroxy-3'-cyclohexylprop-1'-ynyl)-3-hydroxy-6-isopropyl-8-isobutylbicyclo[4.2.0]octane-7,2''-(1'',3''-dioxolane)];

(3'S,1S,2S,3R,6S)-spiro[2-(3'-hydroxy-3'-cyclohexylprop-1'-ynyl)-3-hydroxy-6-n-hexyl-8-methylbicyclo[4.2.0]octane-7,2''-(1'',3''-dioxolane)];

(3'S,1R,2R,3S,6R)-spiro[2-(3'-hydroxy-3'-cyclohexylprop-1'-ynyl)-3-hydroxy-6-n-hexyl-8-methylbicyclo[4.2.0]octane-7,2''-(1'',3''-dioxolane)];

(3'S,1S,2S,3R,6S) spiro[2-(3'-hydroxy-3'-cyclohexylprop-1'-ynyl)-3-hydroxy-6-n-hexyl 8-n-hexylbicyclo[4.2.0]octane-7,2''-(1'',3''-dioxolane)]; and (3'S,1R,2R,3S,6R)-spiro[2-(3'-hydroxy-3'-cyclohexylprop-1'-ynyl)-3-hydroxy-6-n-hexyl-8-n-hexylbicyclo[4.2.0]octane-7,2''-(1'',3''-dioxolane)].

PREPARATION 15

Preparation of
(1'E)-(3'S,1S,2S,3S,6R)-spiro[2-(3'-hydroxy-3'-cyclohexylprop-1'-enyl)-3-hydroxy-6methylbicyclo[4.2.0]octane-7,2''-(1'',3''-dioxolane)] and Related Compounds of Formula (27)

A. To 2.4 g of lithium aluminum hydride in 80 ml of tetrahydrofuran at room temperature under nitrogen is added 2.4 g of (3'S,1S,2R,3S,6R)-spiro[2-(3'-hydroxy-3'-cyclohexylprop-1'-ynyl)-3-hydroxy-6-methylbicyclo[4.2.0]octane-7,2''-(1'',3''-dioxolane)], prepared as shown in Preparation 14, is added. The mixture is refluxed for 3 hours, allowed to cool to room temperature and 2.5 ml of water added dropwise with vigorous stirring, followed by 2.5 ml of 15% aqueous sodium hydroxide and 7.5 ml of water. After 15 minutes the mixture is filtered and the filtrate concentrated under reduced pressure. The residue is chromatographed on silica gel, eluting with hexane:ethyl acetate mixture (2:1), giving (1'E)-(3'S,1S,2S,3S,6R)-spiro[2-(3'-hydroxy-3'-cyclohexylprop-1'-enyl)-3-hydroxy-6-methylbicyclo[4.2.0]octane-7,2''-(1'',3''-dioxolane)].

B. Similarly, starting with the appropriate compound of formula (12) or (13) in place of (3'S,1S,2R,3S,6R)-spiro[2-(3'-t-butyldimethylsilyloxy-3'-cyclohexylprop-1'-ynyl)-3-hydroxy-6-methylbicyclo[4.2.0]octane 7,2''-(1'',3''-dixolane)] in paragraph A above, the following compounds of formula (27) where Y is hydrogen, or Y is lower alkyl (exo or endo, or a mixture of both) are prepared:

(1'E)-(3'S,1R,2R,3R,6S)-spiro[2-(3'-hydroxy-3'-cyclohexylprop-1'-enyl)-3-hydroxy-6-ethylbicyclo[4.2.0]octane-7,1"-(1",3"-dioxolane)];
(1'E)-(3'S,1S,2S,3S,6R)-spiro[2-(3'-hydroxy-3'-cyclohexylprop-1'-enyl)-3-hydroxy-6-ethylbicyclo[4.2.0]octane-7,2"-(1",3"-dioxolane)];
(1'E)-(3'S,1R,2R,3R,6R)-spiro[2-(3'-hydroxy-3'-cyclohexylprop-1'-enyl)-3-hydroxy-6-isopropylbicyclo[4.2.0]octane-7,2"-(1",3"-dioxolane)];
(1'E)-(3'S,1S,2S,3S,6S) spiro[2-(3'-hydroxy-3'-cyclohexylprop-1'-enyl)-3-hydroxy-6-isopropylbicyclo[4.2.0]octane-7,2"-(1",3"-dioxolane)];
(1'E)-(3'S,1R,2R,3R,6S) spiro[2-(3'-hydroxy-3'-cyclohexylprop-1'-enyl)-3-hydroxy-6-n-hexylbicyclo[4.2.0]octane-7,2"-(1",3"-dioxolane)];
(1'E)-(3'S,1S,2S,3S,6R)-spiro[2-(3'-hydroxy-3'-cyclohexylprop-1'-enyl)-3-hydroxy-6-n-hexylbicyclo[4.2.0]octane-7,2"-(1",3"-dioxolane)];
(1'E)-(3'S,1R,2R,3R,6S)-spiro[2-(3'-hydroxy-4'-cyclohexylbut-1'-enyl)-3-hydroxy-6-methylbicyclo[4.2.0]octane-7,2"-(1",3"-dioxolane)];
(1'E)-(3'S,1S,2S,3S,6R)-spiro[2-(3'-hydroxy-4'-cyclohexylbut-1'-enyl)-3-hydroxy-6-methylbicyclo[4.2.0]octane-7,2"-(1",3"-dioxolane)];
(1'E)-(3'S,1R,2R,3R,6S)-spiro[2-(3'-hydroxy-4'-cyclopentylbut-1'-enyl)-3-hydroxy-6-methylbicyclo[4.2.0]octane-7,2"-(1",3"-dioxolane)];
(1'E)-(3'S,1S,2S,3S,6R)-spiro[2-(3'-hydroxy-4'-cyclopentylbut-1'-enyl)-3-hydroxy-6-methylbicyclo[4.2.0]octane-7,2"-(1",3"-dioxolane)];
(1'E)-(3'S,1R,2R,3R,6S)-spiro[2-(3'-hydroxydec-1'-enyl)-3-hydroxy-6-methylbicyclo[4.2.0]octane-7,2"-(1",3"-dioxolane)];
(1'E)-(3'S,1S,2S,3S,6R)-spiro[2-(3'-hydroxydec-1'-enyl)-3-hydroxy-6-methylbicyclo[4.2.0]octane-7,2"-(1",3"-dioxolane)];
(1'E)-(3'S,1R,2R,3R,6S)-spiro[2-(3'-hydroxy-4'-phenoxybut-1'-enyl)-3-hydroxy-6-methylbicyclo[4.2.0]octane-7,2"-(1",3"-dioxolane)];
(1'E)-(3'S,1S,2S,3S,6R)-spiro[2-(3'-hydroxy-4'-phenoxybut-1'-enyl)-3-hydroxy-6-methylbicyclo[4.2.0]octane-7,2"-(1",3"-dioxolane)];
(1'E)-(3'S,1R,2R,3R,6S)-spiro[2-(3'-hydroxy-4'-(endobicyclo[3.1.0]hex-6-yl)but-1'-enyl)-3-hydroxy-6-methylbicyclo[4.2.0]octane-7,2"-(1",3"-dioxolane)];
(1'E)-(3'S,1S,2S,3S,6R)-spiro[2-(3'-hydroxy-4'-(endobicyclo[3.1.0]hex-6-yl)but-1'-enyl)-3-hydroxy-6-methylbicyclo[4.2.0]octane-7,2"-(1",3"-dioxolane)];
(1'E)-(3'S,1S,2R,3R,6S)-spiro[2-(3'-hydroxy-3'cyclohexylprop-1'-enyl)-3-hydroxy-6,8-dimethylbicyclo[4.2.0]octane 7,2"-(1",3"-dioxolane)];
(1'E)-(3'S,1R,2S,3S,6R)-spiro[2-(3'-hydroxy-3'-cyclohexylprop-1'-enyl)-3-hydroxy-6,8-dimethylbicyclo[4.2.0]octane-7,2"-(1",3"-dioxolane)];
(1'E)-(3'S,1S,2R,3R,6S)-spiro[2-(3'-hydroxy-4'-cyclohexylbut-1'-enyl)-3-hydroxy-6,8-dimethylbicyclo[4.2.0]octane-7,2"-(1",3"-dioxolane)];
(1'E)-(3'S,1R,2S,3S,6R)-spiro[2-(3'-hydroxy-4'-cyclohexylbut-1'-enyl)-3-hydroxy-6,8-dimethylbicyclo[4.2.0]octane-7,2"-(1",3"-dioxolane)];
(1'E)-(3'S,1S,2R,3R,6S)-spiro[2-(3'-hydroxy-4'-cyclopentylbut-1'-enyl)-3-hydroxy-6,8-dimethylbicyclo[4.2.0]octane-7,2"-(1",3"-dioxolane)];
(1'E)-(3'S,1R,2S,3S,6R)-spiro[2-(3'-hydroxy-4'-cyclopentylbut-1'-enyl)-3-hydroxy-6,8-dimethylbicyclo[4.2.0]octane-7,2"-(1",3"-dioxolane)];
(1'E)-(3'S,1S,2R,3R,6S)-spiro[2-(3'-hydroxydec-1'-enyl)-3-hydroxy-6,8-dimethylbicyclo[4.2.0]octane-7,2"-(1",3"-dioxolane)];
(1'E)-(3'S,1R,2S,3S,6R)-spiro[2-(3'-hydroxydec-1'-enyl)-3-hydroxy-6,8-dimethylbicyclo[4.2.0]octane-7,2"-(1",3"-dioxolane)];
(1'E)-(3'S,1S,2R,3R,6S) spiro[2-(3'-hydroxy-4'-phenoxybut-1'-enyl)-3-hydroxy-6,8-dimethylbicyclo[4.2.0]octane-7,2"-(1",3"-dioxolane)];
(1'E)-(3'S,1R,2S,3S,6R)-spiro[2-(3'-hydroxy-4'-phenoxybut-1'-enyl)-3-hydroxy-6,8-dimethylbicyclo[4.2.0]octane-7,2"-(1",3"-dioxolane)];
(1'E)-(3'S,1S,2R,3R,6S)-spiro[2-(3'-hydroxy-3'-cyclohexylprop-1'-enyl)-3-hydroxy-6-methyl-8-ethylbicyclo[4.2.0]octane-7,2"-(1",3"-dioxolane)];
(1'E)-(3'S,1R,2S,3S,6R)-spiro[2-(3'-hydroxy-3'-cyclohexylprop-1'-enyl)-3-hydroxy-6-methyl-8-ethylbicyclo[4.2.0]octane-7,2"-(1",3"-dioxolane)];
(1'E)-(3'S,1S,2R,3R,6S) spiro[2-(3'-hydroxy-4'-cyclohexylbut-1'-enyl)-3-hydroxy-6-methyl-8-ethylbicyclo[4.2.0]octane-7,2"-(1",3"-dioxolane)];
(1'E)-(3'S,1R,2S,3S,6R)-spiro[2-(3'-hydroxy-4'-cyclohexylbut-1'-enyl)-3-hydroxy-6-methyl-8-ethylbicyclo[4.2.0]octane-7,2"-(1",3"-dioxolane)];
(1'E)-(3'S,1S,2R,3R,6S)-spiro[2-(3'-hydroxydec-1'-enyl)-3-hydroxy-6-methyl-8-ethylbicyclo[4.2.0]octane-7,2"-(1",3"-dioxolane)];
(1'E)-(3'S,1R,2S,3S,6R)-spiro[2-(3'-hydroxydec-1'-enyl)-3-hydroxy-6-methyl-8-ethylbicyclo[4.2.0]octane-7,2"-(1",3"-dioxolane)];
(1'E)-(3'S,1S,2R,3R,6S)-spiro[2-(3'-hydroxy-4'phenoxybut-1'enyl)-3-hydroxy-6-methyl-8-ethylbicyclo[4.2.0]octane-7,2"-(1",3"-dioxolane)];
(1'E)-(3'S,1R,2S,3S,6R)-spiro[2-(3'-hydroxy-4'-phenoxybut-1'-enyl)-3-hydroxy-6-methyl-8-ethylbicyclo[4.2.0]octane-7,2"-(1",3"-dioxolane)];
(1'E)-(3'S,1S,2R,3R,6S)-spiro[2-(3'-hydroxy-3'-cyclohexylprop-1'-enyl)-3-hydroxy-6-methyl-8-isobutylbicyclo[4.2.0]octane-7,2"-(1",3"-dioxolane)];
(1'E)-(3'S,1R,2S,3S,6R)-spiro[2-(3'-hydroxy-3'-cyclohexylprop-1'-enyl)-3-hydroxy-6-methyl-8-isobutylbicyclo[4.2.0]octane-7,2"-(1",3"-dioxolane)];
(1'E)-(3'S,1S,2R,3R,6S) spiro[2-(3'-hydroxy-3'-cyclohexylprop-1'-enyl)-3-hydroxy-6-methyl-8-n-hexylbicyclo[4.2.0]octane-7,2"-(1",3"-dioxolane)];
(1'E)-(3'S,1R,2S,3S,6R)-spiro[2-(3'-hydroxy-3'-cyclohexylprop-1'-enyl)-3-hydroxy-6-methyl-8-n-hexylbicyclo[4.2.0]octane-7,2"-(1",3"-dioxolane)];
(1'E)-(3'S,1S,2R,3R,6S)-spiro[2-(3'-hydroxy-3'-cyclohexylprop1'-enyl)-3-hydroxy-6-ethyl-8-methylbicyclo[4.2.0]octane-7,2"-(1",3"-dioxolane)];
(1'E)-(3'S,1R,2S,3S,6R)-spiro[2-(3'-hydroxy-3'-cyclohexylprop-1'-enyl)-3-hydroxy-6-ethyl-8-methylbicyclo[4.2.0]octane-7,2"-(1",3"-dioxolane)];
(1'E)-(3'S,1S,2R,3R,6S)-spiro[2-(3'-hydroxy-3'-cyclohexylprop-1'-enyl)-3-hydroxy-6,8-diethylbicyclo[4.2.0]octane-7,2"-(1",3"-dioxolane)];
(1'E)-(3'S,1R,2S,3S,6R)-spiro[2-(3'-hydroxy-3'-cyclohexylprop-1'-enyl)-3-hydroxy-6,8-diethylbicyclo[4.2.0]octane-7,2"-(1",3"-dioxolane)];
(1'E)-(3'S,1S,2R,3R,6S)-spiro[2-(3'-hydroxy-3'-cyclohexylprop-1'-enyl)-3-hydroxy-6-ethyl-8-isobutylbicyclo[4.2.0]octane-7,2"-(1",3"-dioxolane)];
(1'E)-(3'S,1R,2S,3S,6R)-spiro[2-(3'-hydroxy-3'-cyclohexylprop-1'-enyl)-3-hydroxy-6-ethyl-8-isobutylbicyclo[4.2.0]octane-7,2"-(1",3"-dioxolane)];

(1'E)-(3'S,1S,2R,3R,6R)-spiro[2-(3-'-cyclohexylprop-1'-enyl)-3-hydroxy-6-isopropyl-8-methylbicyclo[4.2.0]octane-7,2''-(1'',3''-dioxolane)];

(1'E)-(3'S,1R,2S,3S,6S)-spiro[2-(3'-hydroxy-3'-cyclohexylprop-1'-enyl)-3-hydroxy-6-isopropyl-8-methylbicyclo[4.2.0]octane-7,2''-(1'',3''-dioxolane)];

(1'E)-(3'S,1S,2R,3R,6R)-spiro[2-(3'-hydroxy-3'-cyclohexylprop-1'-enyl)-3-hydroxy-6-isopropyl-8-ethylbicyclo[4.2.0]octane-7,2''-(1'',3''-dioxolane)];

(1'E)-(3'S,1R,2S,3S,6S)-spiro[2-(3'-hydroxy-3'-cyclohexylprop-1'-enyl)-3-hydroxy-6-isopropyl-8-ethylbicyclo[4.2.0]octane-7,2''-(1'',3''-dioxolane)];

(1'E)-(3'S,1S,2R,3R,6R)-spiro[2-(3'-hydroxy-3'-cyclohexylprop-1'-enyl)-3-hydroxy-6-isopropyl-8-isobutylbicyclo[4.2.0]oxtane-7,2''-(1'',3''-dioxolane)];

(1'E)-(3'S,1R,2S,3S,6S) spiro[2-(3'-hydroxy-3'-cyclohexylprop-1'-enyl)-3-hydroxy-6-isopropyl-8-isobutylbicyclo[4.2.0]octane-7,2''-(1'',3''-dioxolane)];

(1'E)-(3'S,1S,2R,3R,6S)-spiro[2-(3'-hydroxy-3'-cyclohexylprop-1'-enyl)-3-hydroxy-6-n-hexyl-8-methylbicyclo[4.2.0]octane-7,2''-(1'',3''-dioxolane)];

(1'E)-(3'S,1R,2S,3S,6R)-spiro[2-(3'-hydroxy-3'-cyclohexylprop-1'-enyl)-3-hydroxy-6-n-hexyl-8-methylbicyclo[4.2.0]octane-7,2''-(1'',3''-dioxolane)];

(1'E)-(3'S,1S,2R,3R,6S)-spiro[2-(3'-hydroxy-3'-cyclohexylprop-1'-enyl)-3-hydroxy-6-n-hexyl-8-n-hexylbicyclo[4.2.0]octane-7,2''-(1'',3''-dioxolane)]; and (1'E)-(3'S,1R,2S,3S,6R)-spiro[2-(3'-hydroxy-3'-cyclohexylprop-1'-enyl)-3-hydroxy-6-n-hexyl-8-n-hexylbicyclo[4.2.0]octane-7,2''-(1'',3''-dioxolane)].

PREPARATION 16

Preparation of (1'E)-(3'S,1S,2S,3S,6R) and (1'E)-(3'R,1S,2S,3S,6R)-2-(3'-hydroxy-3'-cyclohexylprop-1'-enyl)-3-hydroxy-6-methylbicyclo[4.2.0]octan-7-one and Related Compounds of Formula (28) and (29)

A. A solution of 2.0 g of (1'E)-(3'S,1S,2S,3S,6R)-spiro[2-(3'-hydroxy-3'-cyclohexylprop-1'-enyl)-3-hydroxy-6-methylbicyclo[4.2.0]octane-7,2''-(1'',3''-dioxolane)], prepared as shown in Preparation 15, 30 ml of acetonitrile and 15 ml of 1.2M sulfuric acid is stirred at 65° C. for 2 hours. The reaction is quenched by neutralization at room temperature with aqueous sodium bicarbonate and the reaction mixture extracted with diethyl ether. The extracts are dried with magnesium sulfate, the solvent removed under reduced pressure and the residue chromatographed on silica gel, eluting with ethyl acetate-hexane (1:1), to give the two individual compounds (1'E)-(3'S,1S,2S,3S,6R)-2-(3'-hydroxy-3'-cyclohexylprop-1'-enyl)-3-hydroxy-6-methylbicyclo[4.2.0]octan-7-one and (1'E)-(3'R,1S,2S,3S,6R)-2-(3'-hydroxy-3'-cyclohexylprop-1'-enyl )-3-hydroxy-6-methylbicyclo[4.2.0]octan-7-one.

B. Similarly, starting with the appropriate compound of formula (27) in place of (1'E)-(3'S,1S,2S,3S,6R)-spiro[2-(3'-hydroxy-3'-cyclohexylprop-1'-enyl)-3-hydroxy-6-methylbicyclo[4.2.0]octane-7,2''-(1'',3''-dioxolane)] in paragraph A above, the following compounds of formula (28) and (29) where Y is hydrogen, or Y is lower alkyl (exo or endo, or a mixture of both) are prepared:

(1'E)-(3'S,1R,2R,3R,6S)-2-(3'-hydroxy-3'-cyclohexylprop-1'-enyl)-3-hydroxy-6-ethylbicyclo[4.2.0]octan-7-one;

(1'E)-(3'S,1S,2S,3S,6R)-2-(3'-hydroxy-3'-cyclohexylprop-1'-enyl)-3-hydroxy-6-ethylbicyclo[4.2.0]octan-7-one;

(1'E)-(3'R,1S,2S,3S,6R)-2-(3'-hydroxy-3'-cyclohexylprop-1'-enyl)-3-hydroxy-6-ethylbicyclo[4.2.0]octan-7-one;

(1'E)-(3'S,1R,2R,3R,6R)-2-(3'-hydroxy-3'-cyclohexylprop-1'-enyl)-3-hydroxy-6-isopropylbicyclo[4.2.0]octan-7-one;

(1'E)-(3'S,1S,2S,3S,6S)-2-(3'-hydroxy-3'-cyclohexylprop-1'-enyl)-3-hydroxy-6-isopropylbicyclo[4.2.0]octan-7-one;

(1'E)-(3'R,1S,2S,3S,6S)-2-(3'-hydroxy-3'-cyclohexylprop-1'-enyl)-3-hydroxy-6-isopropylbicyclo[4.2.0]octan-7-one;

(1'E)-(3'S,1R,2R,3R,6S)-2-(3'-hydroxy-3'-cyclohexylprop-1'-enyl)-3-hydroxy-6-n-hexylbicyclo[4.2.0]octan-7-one;

(1'E)-(3'S,1S,2S,3S,6R)-2-(3'-hydroxy-3'-cyclohexylprop-1'-enyl)-3-hydroxy-6-n-hexylbicyclo[4.2.0]octan-7-one;

(1'E)-(3'R,1S,2S,3S,6R)-2-(3'-hydroxy-3'-cyclohexylprop-1'-enyl)-3-hydroxy-6-n-hexylbicyclo[4.2.0]octan-7-one;

(1'E)-(3'S,1R,2R,3R,6S)-2-(3'-hydroxy-4'-cyclohexylbut-1'-enyl)-3-hydroxy-6-methylbicyclo[4.2.0]octan-7-one;

(1'E)-(3'S,1S,2S,3S,6R)-2-(3'-hydroxy-4'-cyclohexylbut-1'-enyl)-3-hydroxy-6-methylbicyclo[4.2.0]octan-7-one;

(1'E)-(3'R,1S,2S,3S,6R)-2-(3'-hydroxy-4'-cyclohexylbut-1'-enyl)-3-hydroxy-6-methylbicy:lo[4.2.0]octan-7-one;

(1'E)-(3'S,1R,2R,3R,6S)-2-(3'-hydroxy-4'-cyclopentylbut-1'-enyl)-3-hydroxy-6-methylbicyclo[4.2.0]octan-7-one;

(1'E)-(3'S,1S,2S,3S,6R)-2-(3'-hydroxy-4'-cyclopentylbut-1'-enyl)-3-hydroxy-6-methylbicyclo[4.2.0]octan-7-one;

(1'E)-(3'R,1S,2S,3S,6R)-2-(3'-hydroxy-4'-cyclopentylbut-1'-enyl)-3-hydroxy-6-methylbicyclo[4.2.0]octan-7-one;

(1'E)-(3'S,1R,2R,3R,6S)-2-(3'-hydroxydec-1'-enyl)-3-hydroxy-6-methylbicyclo[4.2.0]octan-7-one;

(1'E)-(3'S,1S,2S,3S,6R)-2-(3'-hydroxydec-1'-enyl)-3-hydroxy-6-methylbicyclo[4.2.0]octan-7-one;

(1'E)-(3'R,1S,2S,3S,6R)-2-(3'-hydroxydec-1'-enyl)-3-hydroxy-6-methylbicyclo[4.2.0]octan-7-one;

(1'E)-(3'S,1R,2R,3R,6S)-2-(3'-hydroxy-4'-phenoxybut-1'-enyl)-3-hydroxy-6-methylbicyclo[4.2.0]octan-7-one;

(1'E)-(3'S,1S,2S,3S,6R)-2-(3'-hydroxy-4'-phenoxybut-1'-enyl)-3-hydroxy-6-methylbicyclo[4.2.0]octan-7-one;

(1'E)-(3'R,1S,2S,3S,6R)-2-(3'-hydroxy-4'-phenoxybut-1'-enyl)-3-hydroxy-6-methylbicyclo[4.2.0]octan-7-one;

(1'E)-(3'S,1R,2R,3R,6S)-2-(3'-hydroxy-4'-methylbicyclo[4.2.0]octan-7-one;

(1'E)-(3'S,1S,2S,3S,6R)-2-(3'-hydroxy-4'-(endo-bicyclo[3.1.0]hex-6-yl)but-1'-enyl)-3-hydroxy-6-methylbicyclo[4.2.0]octan-7-one;

(1'E)-(3'R,1S,2S,3S,6R)-2-(3'-hydroxy-4'-(endo-bicyclo[3.1.0]hex-6-yl)but-1'-enyl)-3-hydroxy-6-methylbicyclo[4.2.0]octan-7-one;

(1'E)-(3'S,1R,2R,3R,6S)-2-(3'-hydroxy-3'-cyclohexylprop-1'-enyl)-3-hydroxy-6,8-dimethylbicyclo[4.2.0]octan-7-one;

(1'E)-(3'S,1R,2S,3S,6R)-2-(3'-hydroxy-3'-cyclohexyl-prop-1'-enyl)-3-hydroxy-6,8-dimethylbicy-clocyc[4.2.0]octan-7-one;
(1'E)-(3'R,1R,2S,3S,6R)-2-(3'-hydroxy-3'-cyclohexyl-prop-1'-enyl)-3-hydroxy-6,8-dimethylbicyclo[4.2.0]octan-7-one;
(1'E)-(3'S,1S,2R,3R,6S)-2-(3'-hydroxy-4'-cyclohexyl-but-1'-enyl)-3-hydroxy-6,8-dimethylbicyclo[4.2.0]octan-7-one;
(1'E)-(3'S,1R,2S,3S,6R)-2-(3'-hydroxy-4'-cyclohexyl-but-1'-enyl)-3-hydroxy-6,8-dimethylbicyclo[4.2.0]octan-7-one;
(1'E)-(3'R,1R,2S,3S,6R)-2-(3'-hydroxy-4'-cyclohexyl-but-1'-enyl)-3-hydroxy-6,8-dimethylbicyclo[4.2.0]octan-7-one;
(1'E)-(3'S,1S,2R,3R,6S)-2-(3'-hydroxy-4'-cyclopentyl-but-1'-enyl)-3-hydroxy-6,8-dimethylbicyclo[4.2.0]octan-7-one;
(1'E)-(3'S,1R,2S,3S,6R)-2-(3'-hydroxy-4'-cyclopentyl-but-1'-enyl)-3-hydroxy-6,8-dimethylbicyclo[4.2.0]octan-7-one;
(1'E)-(3'R,1R,2S,3S,6R)-2-(3'-hydroxy-4'-cyclopentyl-but-1'-enyl)-3-hydroxy-6,8-dimethylbicyclo[4.2.0]octan-7-one;
(1'E)-(3'S,1S,2R,3R,6S)-2-(3'-hydroxy-4'-phenoxybut-1'-enyl)-3-hydroxy-6,8-dimethylbicyclo[4.2.0]octan-7-one;
(1'E)-(3'S,1R,2S,3S,6R)-2-(3'-hydroxy-4'-phenoxybut-1'-enyl)-3-hydroxy-6,8-dimethylbicyclo[4.2.0]octan-7-one;
(1'E)-(3'R,1R,2S,3S,6R)-2-(3'-hydroxy-4'-phenoxybut-1'-enyl)-3-hydroxy-6,8-dimethylbicyclo[4.2.0]octan-7-one;
(1'E)-(3'S,1S,2R,3R,6S)-2-(3'-hydroxy-3'-cyclohexyl-prop-1'-enyl)-3-hydroxy-6-methyl-8-ethylbicyclo[4.2.0]octan-7-one;
(1'E)-(3'S,1R,2S,3S,6R)-2-(3'-hydroxy-3'-cyclohexyl-prop-1'-enyl)-3-hydroxy-6-methyl-8-ethylbicyclo[4.2.0]octan-7-one;
(1'E)-(3'R,1R,2S,3S,6R)-2-(3'-hydroxy-3'-cyclohexyl-prop-1'-enyl)-3-hydroxy-6-methyl-8-ethylbicyclo[4.2.0]octan-7-one;
(1'E)-(3'S,1S,2R,3R,6S)-2-(3'-hydroxy-3'-cyclohexyl-prop-1'-enyl)-3-hydroxy-6-methyl-8-n-hexylbicyclo[4.2.0]octan-7-one;
(1'E)-(3'S,1R,2S,3S,6R)-2-(3'-hydroxy-3'-cyclohexyl-prop-1'-enyl)-3-hydroxy-6-methyl-8-n-hexylbicyclo[4.2.0]octan-7-one;
(1'E)-(3'R,1R,2S,3S,6R)-2-(3'-hydroxy-3'-cyclohexyl-prop-1'-enyl)-3-hydroxy-6-methyl-8-n-hexylbicyclo[4.2.0]octan-7-one;
(1'E)-(3'S,1S,2R,3R,6S)-2-(3'-hydroxy-3'-cyclohexyl-prop-1'-enyl)-3-hydroxy-6-ethyl-8-methylbicyclo[4.2.0]octan-7-one;
(1'E)-(3'S,1R,2S,3S,6R)-2-(3'-hydroxy-3'-cyclohexyl-prop-1'-enyl)-3-hydroxy-6-ethyl-8-methylbicyclo[4.2.0]octan-7-one;
(1'E)-(3'R,1R,2S,3S,6R)-2-(3'-hydroxy-3'-cyclohexyl-prop-1'-enyl)-3-hydroxy-6-ethyl-8-methylbicyclo[4.2.0]octan-7-one;
(1'E)-(3'S,1S,2R,3R,6R)-2-(3'-hydroxy-3'-cyclohexyl-prop-1'-enyl)-3-hydroxy-6-isopropyl-8-methylbicyclo[4.2.0]octan-7-one;
(1'E)-(3'S,1R,2S,3S,6S)-2-(3'-hydroxy-3'-cyclohexyl-prop-1'-enyl)-3-hydroxy-6-isopropyl-8-methylbicyclo[4.2.0]octan 7-one;
(1'E)-(3'S,1S,2S,3S,6S)-2-(3'-hydroxy-3'-cyclohexyl-prop-1'-enyl)-3-hydroxy-6-isopropyl-8-methylbicyclo[4.2.0]octan-7-one;
(1'E)-(3'S,1S,2R,3R,6S)-2-(3'-hydroxy-3'-cyclohexyl-prop-1'-enyl)-3-hydroxy-6-n-hexyl-8-n-hexylbicyclo[4.2.0]octan 7-one;
(1'E)-(3'S,1R,2S,3S,6R)-2-(3'-hydroxy-3'-cyclohexyl-prop-1'-enyl)-3-hydroxy-6-n-hexyl-8-n-hexylbicyclo[4.2.0]octan-7-one; and
(1'E)-(3'R,1R,2S,3S,6R)-2-(3'-hydroxy-3'-cyclohexyl-prop-1'-enyl)-3-hydroxy-6-n-hexyl-8-n-hexylbicyclo[4.2.0]octan-7-one.

PREPARATION 17

Preparation of (3'R,1S,2S,3S,6R)-2-(3'-hydroxyl-3'-cyclohexylprop-1'-yl)-3-hydroxy-6-methylbicyclo[4.2.0]octan-7one and Related Compounds of Formula (32) and (33)

A. A solution of 2.0 g of (1'E)-(3'S,1S,2S,3S,6R)-spiro[2-(3'-hydroxy-3'-cyclohexylprop-1'-enyl)-3-hydroxy-6-methylbicyclo[4.2.0]octan-7-one, prepared as shown in Preparation 16, in 10 ml of ethanol was stirred under hydrogen in the presence of 200 mg of a 10% palladium on charcoal catalyst until the theoretical amount of hydrogen had been absorbed. The catalyst was filtered off, the solvent removed from the filtrate under reduced pressure and the residue chromatographed on silica gel eluting with ethyl acetate-hexane (1:1) to give (3'R,1S,2S,3S,6R)-2-(3'-hydroxy-3'-cyclohexylprop-1'-yl)-3-hydroxy-6-methylbicyclo[4.2.0]octan-7-one, the compound of formula (32).

B. Similarly, starting with the appropriate compound of formula (28) or (29) (or alternatively the compound of formula (16) or (17) may be used), in place of (1'E)-(3'S,1S,2S,3S,6R)-spiro[2-(3'-hydroxy-3'-cyclohexylprop-1'-enyl)-3-hydroxy-6-methylbicyclo[4.2.0]octan-7-one in paragraph A above, the following compounds of formula (32) and (33) where Y is hydrogen, or Y is lower alkyl (exo or endo, or a mixture of both) are prepared:

(3'R,1R,2R,3R,6S)-2-(3'-hydroxy 3'-cyclohexylprop-1'-yl)-3-hydroxy-6-ethylbicyclo[4.2.0]octan-7-one;
(3'R,1S,2S,3S,6R)-2-(3'-hydroxy-3'-cyclohexylprop-1'-yl)-3-hydroxy-6-ethylbicyclo[4.2.0]octan-7-one;
(3'S,1S,2S,3S,6R)-2-(3'-hydroxy-3'-cyclohexylprop-1'-yl)-3-hydroxy-6-ethylbicyclo[4.2.0]octan-7-one;
(3'R,1R,2R,3R,6R)-2-(3'-hydroxy-3'-cyclohexylprop-1'-yl)-3-hydroxy-6-isopropylbicyclo[4.2.0]octan-7-one;
(3'R,1S,2S,3S,6S)-2-(3'-hydroxy-3'-cyclohexylprop-1'-yl)-3-hydroxy-6-isopropylbicyclo[4.2.0]octan-7-one;
(3'S,1S,2S,3S,6S)-2-(3'-hydroxy-3'-cyclohexylprop-1'-yl)-3-hydroxy-6-isopropylbicyclo[4.2.0]octan-7-one;
(3'R,1R,2R,3R,6S)-2-(3'-hydroxy-3'-cyclohexylprop-1'-yl)-3-hydroxy-6-n-hexylbicyclo[4.2.0]octan-7-one;
(3'R,1S,2S,3S,6R)-2-(3'-hydroxy-3'-cyclohexylprop-1'-yl)-3-hydroxy-6-n-hexylbicyclo[4.2.0]octan-7-one;
(3'S,1S,2S,3S,6R)-2-(3'-hydroxy-3'-cyclohexylprop-1'-yl)-3-hydroxy-6-n-hexylbicyclo[4.2.0]octan-7-one;
(3'R,1R,2R,3R,6S)-2-(3'-hydroxy-4'-cyclohexylbut-1'-yl)-3-hydroxy-6-methylbicyclo[4.2.0]octan-7-one;
(3'R,1S,2S,3S,6R)-2-(3'-hydroxy-4'-cyclohexylbut-1'-yl)-3-hydroxy-6-methylbicyclo[4.2.0]octan-7-one;
(3'S,1S,2S,3S,6R)-2-(3'-hydroxy-4'-cyclohexylbut-1'-yl)-3-hydroxy-6-methylbicyclo[4.2.0]octan-7-one;
(3'R,1R,2R,3R,6S)-2-(3'-hydroxy-4'-cyclopentylbut-1'-yl)-3-hydroxy-6-methylbicyclo[4.2.0]octan-7-one;

(3′R,1S,2S,3S,6R)-2-(3′-hydroxy-4′-cyclopentylbut-1′-yl)-3-hydroxy 6-methylbicyclo[4.2.0]octan-7-one;
(3′S,1S,2S,3S,6R)-2-(3′-hydroxy-4′-cyclopentylbut-1′-yl)-3-hydroxy-6-methylbicyclo[4.2.0]octan-7-one;
(3′S,1R,2R,3R,6S)-2-(3′-hydroxydec-1′-yl)-3-hydroxy-6-methylbicyclo[4.2.0]octan-7-one;
(3′R,1S,2S,3S,6R)-2-(3′-hydroxydec-1′-yl)-3-hydroxy-6-methylbicyclo[4.2.0]octan-7-one;
(3′S,1S,2S,3S,6R)-2-(3′-hydroxydec 1′-yl)-3-hydroxy-6-methylbicyclo[4.2.0]octan-7-one;
(3′R,1R,2R,3R,6S)-2-(3′-hydroxy-4′-phenoxybut-1′-yl)-3-hydroxy-6-methylbicyclo[4.2.0]octan-7-one;
(3′R,1S,2S,3S,6R)-2-(3′-hydroxy-4′-phenoxybut-1′-yl)-3-hydroxy 6-methylbicyclo[4.2.0]octan-7 one;
(3′S,1S,2S,3S,6R)-2-(3′-hydroxy 4′-phenoxybut-1′-yl)-3-hydroxy-6-methylbicyclo[4 2.0]octan-7-one;
(3′R,1S,2R,3R,6S)-2 (3′-hydroxy-3′-cyclohexylprop-1′-yl)-3-hydroxy-6,8-dimethylbicyclo[4.2.0]octan-7-one;
(3′R,1R,2S,3S,6R)-2-(3′-hydroxy-3′-cyclohexylprop-1′-yl)-3-hydroxy-6,8-dimethylbicyclo[4.2.0]octan-7-one;
(3′S,1R,2S,3S,6R)-2-(3′-hydroxy-3′-cyclohexylprop-1′-yl)-3-hydroxy-6,8-dimethylbicyclo[4.2.0]octan-7-one;
(3′R,1S,2R,3R,6S)-2-(3′-hydroxy-4′-cyclohexylbut-1′-yl)-3-hydroxy-6,8-dimethylbicyclo[4. 2.0]octan-7-one;
(3′R,1R,2S,3S,6R)-2-(3′-hydroxy-4′-cyclohexylbut-1′-yl)-3-hydroxy-6,8-dimethylbicyclo[4.2.0]octan-7 -one;
(3′S,1R,2S,3S,6R)-2-(3′-hydroxy-4′-cyclohexylbut-1′-yl)-b 3-hydroxy-6,8-dimethylbicyclo[4.2.0]octan-7-one;
(3′R,1S,2R,3R,6S)-2-(3′-hydroxy-4′-cyclopentylbut-1′-yl)-3-hydroxy-6,8-dimethylbicyclo[4.2.0octan-7-one;
(3′R,1R,2S,3S,6R)-2-(3′-hydroxy-4′-cyclopentylbut-1′-yl)-3-hydroxy-6,8 -dimethylbicyclo[4.2.0]octan-7-one;
(3′S,1R,2S,3S,6R)-2-(3′-hydroxy-4′-cyclopentylbut-1′-yl)-3-hydroxy-6,8 -dimethylbicyclo[4.2.0octan7 -one;
(3′R,1S,2R,3R,6S)-2-(3′-hydroxy-4′-phenoxybut-1′-yl)-3-hydroxy-6,8-dimethylbicyclo[4.2.0]octan-7-one;
(3′R,1R,2S,3S,6R)-2-(3′-hydroxy 4′-phenoxybutl′yl)-3-hydroxy-6,8-dimethylbicyclo[4.2.0]octan-7-one;
(3′S,1R,2S,3S,6R)-2-(3′-hydroxy-4′-phenoxybutl′-yl)-3-hydroxy-6,8-dimethylbicyclo[4.2.0]octan-7-one;
(3′R,1S,2R,3R,6S)-2-(3′-hydroxy-3′-cyclohexylprop-1′-yl)-3-hydroxy-6-methyl-8-ethylbicyclo[4.2.0]octan-7-one;
(3′R,1R,2S,3S,6R)-2-(3′-hydroxy 3′-cyclohexylprop-1′-yl)-3-hydroxy-6-methyl-8-ethylbicyclo[4.2.0]octan-7-one,
(3′S,1R,2S,3S,6R) 2-(3′-hydroxy-3′cyclohexylprop-1′-yl)-3-hydroxy-6-methyl-8-ethylbicyclo[4.2.0]octan 7-one;
(3′R,1S,2R,3R,6S)-2-(3′-hydroxy-3′-cyclohexylprop-1′-yl)-3-hydroxy-6-methyl-8-n-hexylbicyclo[4.2.0]-octan-7-one;
(3′R,1R,2S,3S,6R)-2-(3′-hydroxy-3′-cyclohexylprop-1′-yl)-3-hydroxy-6-methyl-8-n-hexylbicyclo[4.2.0]octan-7-one;
(3′S,1R,2S,3S,6R)-2-(3′-hydroxy-3′-cyclohexylprop-1′-yl)-3-hydroxy-6-methyl-8-n-hexylbicyclo[4.2.0]-octan 7-one;
(3′R,1S,2R,3R,6S)-2 (3′-hydroxy- 3′-cyclohexylprop-1′yl)-3-hydroxy-6-ethyl- 8-methylbicyclo[4.2 0]octan-7-one;

(3′R,1R,2S,3S,6R) 2-(3′-hydroxy-3′-cyclohexylprop-1′-yl)-3-hydroxy-6-ethyl-8-methylbicyclo[4.2.0]octan-7-one:
(3′S,1R,2S,3S,6R) 2-(3′-hydroxy-3′-cyclohexylprop-1′yl)-3-hydroxy- 6-ethyl-8-methylbicyclo[4.2.0]octan-7-one;
(3′R,1S,2R,3R,6R)-2-(3′-hydroxy-3′-cyclohexylprop-1′-yl)-3-hydroxy-6-isopropyl-8-methylbicyclo[4.2.0]octan-7-one;
(3′R,1R,2S,3S,6S)-2-(3′-hydroxy-3′-cyclohexylprop-1′-yl)-3-hydroxy-6-isopropyl-8-methylbicyclo[4.2.0]octan-7-one;
(3′S,1S,2S,3S,6S)-2-(3′-hydroxy-3′-cyclohexylprop-1′-yl)-3-hydroxy-6-isopropyl-8-methylbicyclo[4.2.0]octan-7-one;
(3′R,1S,2R,3R,6S)-2-(3′hydroxy-3′-cyclohexylprop-1′-yl)-3-hydroxy-6-n-hexyl-8-n-hexylbicyclo[4.2.0]octan-7-one;
(3′R,1R,2S,3S,6R)-2-(3′-hydroxy-3′-cyclohexylprop-1′-yl)-3-hydroxy-6-n-hexyl-8-n-hexylbicyclo[4.2.0]octan- 7-one; and
(3′S,1R,2S,3S,6R)-2 (3′hydroxy 3′-cyclohexylprop-1′-yl)-3-hydroxy-6-n-hexyl-8-n-hexylbicyclo[4.2.0]octan-7-one.

PREPARATION 18

Preparation of 6-chlorobicyclo[4.2.0]oct-2-en-7-one oxime and Related Compounds of Formula (6A)

A solution of 6.2 g of 6-chlorobicyclo[4.2.0]oct-2-en-7-one, prepared as shown in Preparation 7, and 3.4 g. of hydroxylamine hydrochloride in 30 ml of pyridine was stirred at 0° C. for 1 hour, then stirred overnight at room temperature. The mixture was poured into water and extracted with methylene chloride. The extract was washed with 0.5N hydrochloric acid followed by brine, and dried over anhydrous sodium sulfate. The solvent was evaporated under reduced pressure and the residual pyridine removed under high vacuum. The residue was dissolved in diethyl ether, filtered and solvent removed from the filtrate under reduced pressure, to give 6-chlorobicyclo[4.2.0]oct-2-en-7-one oxime, the compound of formula (6A) where Y is hydrogen, 5.4 g.

B. Similarly, starting with the appropriate compound of formula (6) in place of 6-chlorobicyclo[4.2.0]oct-2-en-7-one in paragraph A above, the following compounds of formula (6) where Y is lower alkyl are prepared:

6-chloro-8-exo-methylbicyclo[4.2.0]oct-2-en-7-one oxime;
6-chloro 8-endo-methylbicyclo[4.2.0]oct-2-en-7-one oxime;
6-chloro-8-endo-ethylbicyclo[4.2.0]oct-2-en-7-one oxime,
6-chloro-8-exo-ethylbicyclo[4.2.0]oct-2-en-7-one oxime;
6-chloro-8-endo-isobutylbicyclo[4.2.0]oct-2-en-7-one oxime; and
6-chloro-8-exo isobutylbicyclo[4.2.0]oct-2-en-7-one oxime.
6-chloro-8-endo-n-hexylbicyclo[4.2.0]oct-2-en-7-one oxime; and
6-chloro-8-exo-n-hexylbicyclo[4.2.0]oct-2-en-7-one oxime.

PREPARATION 19

Preparation of 6-methylbicyclo[4.2.0 oct-2-en-7-one oxime and Related Compounds of Formula (7A)

To a slurry of 6.3 g of cuprous iodide in 70 ml of diethylether at 0° C. was added 44 ml of 1.5M methyllithium in ether over 15 minutes. The resulting solution was stirred for 20 minutes at 0° C., then cooled to −78° C. A solution of 6-chlorobicyclo[4.2.0]oct-2-en-7-one oxime, prepared as shown in Preparation 18, in ether was added and the mixture stirred at −78° C. to −60° C. for 30 minutes. Saturated ammonium chloride solution (10 ml) was slowly added and the mixture filtered. The filtrate was washed with ether, the combined washings dried over anhydrous sodium sulfate and solvent removed from the filtrate under reduced pressure, to give 6-methylbicyclo[4 2.0]oct-2-en-7-one oxime, the compound of formula (7A) where Y is hydrogen, 5.4 g.

B. Similarly, starting with the appropriate compound of formula (6A) in place of 6-chlorobicyclo[4.2.0]oct-2-en-7-one oxime in paragraph A above, the following compounds of formula (7A) where Y is hydrogen, or Y is lower alkyl (exo or endo) are prepared:
6-ethylbicyclo[4.2.0]oct-2-en-7-one oxime;
6-isopropylbicyclo[4.2.0]oct-2-en-7-one oxime;
6n-hexylbicyclo[4.2.0]oct-2-en-7-one oxime;
6-methyl-8methylbicyclo[4.2.0]oct-2-en-7-one oxime;
6methyl-8-ethylbicyclo[4.2.0]oct-2-en-7-one oxime;
6-methyl-8-isobutylbicyclo[4.2.0]oct-2-en-7-one oxime;
6-methyl-8-n-hexylbicyclo[4.2.0]oct-2-en-7-one oxime;
6-ethyl-8-methylbicyclo[4.2.0]oct-2-en-7-one oxime;
6-ethyl-8-ethylbicyclo[4.2.0]oct-2-en-7-one oxime;
6-ethyl-8-isobutylbicyclo[4.2.0]oct-2-en-7-one oxime;
6-isopropyl-8-methylbicyclo[4.2.0]oct-2-en-7-one oxime;
6-isopropyl-8-ethylbicyclo[4.2.0]oct-2 en-7-one oxime;
6-isopropyl-8-isobutylbicyclo[4.2.0]oct-2-en-7-one oxime;
6-n-hexyl-8-methylbicyclo[4.2.0]oct-2-en-7-one oxime; and
6-n-hexyl-8-n-hexylbicyclo[4.2.0]oct-2-en-7-one oxime.

PREPARATION 20

Preparation of 6-methylbicyclo[4.2.0]oct-2-en-7-one and Related Compounds of Formula (8)

A solution of 120 mg of 6-methylbicyclo[4.2.0]oct-2-en-7-one oxime, prepared as shown in Preparation 19, in 4 ml of levulinic acid/1N hydrochloric acid (9/1) was stirred at room temperature for 48 hours. The mixture was poured into water and extracted with hexane. The combined hexane extracts were washed with saturated sodium bicarbonate, brine and dried over anhydrous sodium sulfate. Solvent was carefully removed under reduced pressure, and the residue chromatographed on silica gel, eluting with 10% ethyl acetate in hexane, to give 6-methylbicyclo[4.2.0]oct-2-en-7-one, the compound of formula (8).

B. Similarly, starting with the appropriate compound of formula (7A) in place of 6-methylbicyclo[4.2.0]oct-2-en-7-one oxime in paragraph A above, the following compounds of formula (8) where Y is hydrogen, or Y is lower alkyl (exo or endo) are prepared:
6-ethylbicyclo[4.2.0]oct-2 -en-7-one;
6-isopropylbicyclo[4.2.0]oct-2-en-7-one;
6-n-hexylbicyclo[4.2.0]oct-2-en-7-one;
6-methyl-8-methylbicyclo[4.2.0]oct-2-en-7-one;
6-methyl-8-ethylbicyclo[4.2.0]oct-2-en-7-one;
6-methyl-8-isobutylbicyclo[4.2.0]oct-2-en-7-one;
6-methyl-8-n hexylbicyclo[4.2.0]oct-2-en-7-one;
6-ethyl-8-methylbicyclo[4.2.0]oct-2-en-7-one;
6-ethyl-8-ethylbicyclo[4.2.0]oct-2-en-7-one;
6-ethyl-8-isobutylbicyclo[4.2.0]oct-2-en-7-one;
6-isopropyl-8-methylbicyclo[4.2.0]oct-2-en-7-one;
6-isopropyl-8-ethylbicyclo[4.2.0]oct-2-en-7-one;
6-isopropyl-8-isobutylbicyclo[4.2.0]oct-2-en-7-one;
6-n-hexyl-8-methylbicyclo[4.2.0]oct-2-en-7-one; and
6-n-hexyl-8-n-hexylbicyclo[4.2.0]oct-2-en-7-one.

PREPARATION 21

Preparation of (3'S,1R,2S,3R,6S)-2-(3'-tert-butyldimethylsiloyloxy-3'-cyclohexylprop-1'-ynyl)-3-tert-butyldimethylsilyloxybicyclo[4.2.0]octan-7-one and Related Compounds of Formula (19)

A. A mixture of 0.50 g (3'S,1R,2S,3R,6S)-4-[2-(3'-hydroxy-3'-cyclohexylprop-1'-ynyl)-3-hydroxybicyclo[4.2.0]octan-7-one, the compound of formula (18), 0.68 g tert-butyldimethylsilyl chloride, 0.615 g of imidazole and 15 ml of N,N-dimethylformamide was stirred at 23° C. for 24 hours. After dilution with brine the mixture was extracted with ethyl acetate and the extracts dried over anhydrous sodium sulfate. Solvent was removed under reduced pressure, and the residue chromatographed on silica gel, eluting with 5% ethyl acetate in hexane, to give (3'S,1R,2S,3R,6S)-2-(3'-tert-butyldimethylsilyloxy-3'-cyclohexylprop-1'-ynyl)-3-tert-butyldimethylsilyloxybicyclo[4.2.0]octan-7-one, the compound of formula (19).

B. Similarly, starting with the appropriate compound of formula (18) in place of (3'S,1R,2S,3R, 6S)-4 -[2-(3'-hydroxy-3'-cyclohexylprop-1'-ynyl)-3-hydroxybicyclo[4.2.0]octan-7-one in paragraph A above, the following compounds of formula (19) are prepared:
(3'S,1S,2R,3S,6R)-2-(3't-butyldimethylsilyloxy-3'-cyclohexylprop-1'-ynyl)-3-t-butyldimethylsilyloxybicyclo[4.2.0]octan-7-one;
(3'S,1R,2S,3R,6S)-2-(3'-t-butyldimethylsilyloxy-4'-cyclohexylbut-1'-ynyl)-3-t-butyldimethylsilyloxybicyclo[4.2.0]octan-7-one;
(3'S,1S,2R,3S,6R)-2-(3'-t-butyldimethylsilyloxy-4'-cyclohexylbut-1'-ynyl)-3-t-butyldimethylsilyloxybicyclo[4.2.0]octan-7-one;
(3'S,1R,2S,3R,6S)-2-(3'-t-butyldimethylsilyloxy-4'-cyclopentylbut-1'-ynyl)-3-t-butyldimethylsilyloxybicyclo[4.2.0]octan-7-one;
(3'S,1S,2R,3S,6R)-2-(3'-t-butyldimethylsilyloxy-4'-cyclopentylbut-1'-ynyl)-3-t-butyldimethylsilyloxybicyclo[4.2.0]octan-7-one;
(3'S,1R,2S,3R,6S)-2-(3't-butyldimethylsilyloxydec-1'-ynyl)-3-t-butyldimethylsilyloxybicyclo]4.2.0]octan-7-one;
(3'S,1S,2R,3S,6R)-2-(3't-butyldimethylsilyloxydec-1'-ynyl)-3-t-butyldimethylsilyloxybicyclo[4.2.0]octan-7-one;
(3'S,1R,2S,3R,6S)-2-(3'-t-butyldimethylsilyloxy-4'-phenoxybut-1'-ynyl)-3-t-butyldimethylsilyloxybicyclo[4.2.0]octan-7-one;
(3'S,1S,2R,3S,6R)-2-(3'-t-butyldimethylsilyloxy-4'-phenoxybut-1'-ynyl)-3-t-butyldimethylsilyloxybicyclo[4.2.0]octan-7-one;
(3'S,1R,2S,3R,6S)-2-(3'-t-butyldimethylsilyloxy-4'-(endo-bicyclo[3.1.0]hex-6-yl)but-1'-ynyl)-3-t-butyldimethylsilyloxybicyclo[4.2.0]octan-7-one; and (3'S,1S,2R,3S,6R)-2-(3'-t-butyldimethylsilyloxy-4'-(endo-bicyclo[3.1.0]hex-6-yl)but-1'-ynyl)-3-t-butyldimethylsilyloxybicyclo[4.2.0]octan-7-one.

PREPARATION 22

Preparation of (3'S,1; R,2; S,3R,6S)-2-(3'-hydroxy-3'-cyclohexylprop-1'-ynyl)-3-hydroxy-6-ethylbicyclo[4.2.0]octan-7-one and Related Compounds of Formula (22)

A.

(1) A solution of 1M lithium hexamethyldisilazane (1.6 ml) in tetrahydrofuran was cooled to −78° C., and a solution of 671 mg of (3'S,1R,2S,3R, 6S)-2 -(3'-tert-butyldimethylsilyloxy-3'-cyclohexylprop-1'-ynyl)-3-tert-butyldimethylsilyloxybicyclo[4.2.0]octan-7-one, prepared as shown in Preparation 21, in 10 ml of tetrahydrofuran was added dropwise. The reaction mixture was stirred at −78° C. for 30 minutes, then 2 ml of ethyl iodide in 0.5 ml of hexamethylphosphoramide added in one portion. The reaction mixture was stirred at −78° C. for 1 hour, then allowed to warm slowly to room temperature. After stirring for 2 hours, saturated ammonium chloride was added, the mixture extracted with ethyl acetate, and the extracts dried over anhydrous sodium sulfate. Solvent was removed under reduced pressure, and the residue chromatographed on silica gel, eluting with 2% ethyl acetate in hexane, to give (3'S,1R,2S,3R,6S)-2-(3'-tertbutyldimethylsilyloxy-3'-cyclohexylprop-1'-ynyl)-3-tert-butyldimethylsilyloxy-6-ethylbicyclo[4.2.0]octan-7-one, the compound of formula (20).

(2) A solution of 500 mg of (3'S,1R,2S,3R,6S)-2-(3'-tert-butyldimethylsilyloxy-3'-cyclohexylprop-1'-ynyl)-3-tert-butyldimethylsilyloxy-6-ethylbicyclo[4.2.0]octan-7-one, prepared as shown in A(1) above, 10 ml of acetonitrile and 5 ml of 2N sulfuric acid was stirred at room temperature for 16 hours. The reaction was quenched by neutralization at room temperature with aqueous sodium bicarbonate and the reaction mixture extracted with diethyl ether. The extracts were dried with magnesium sulfate, the solvent removed under reduced pressure and the residue chromatographed on silica gel, eluting with 70% ethyl acetate in hexane, to give (3'S,1R,2S,3R,6S)-2-(3'-hydroxy-3'-cyclohexyl-prop-1'-ynyl)-3-hydroxy-6-ethylbicyclo[4.2.0]octan-7-one.

B. Similarly, starting with methyl iodide and following the procedure of paragraphs A(1) and A(2), above, the following compounds of formula (22) was prepared: (3'S,1R,2S,3R,6S)-2-(3'-hydroxy-3'-cyclohexylprop-1'-ynyl)-3-hydroxy-6-methylbicyclo[4.2.0]octan-7-one.

C. Similarly, starting with the appropriate alkyl halide in place of ethyl iodide and following the procedure of paragraphs A(1) and A(2), above, the following compounds of formula (22) are prepared:
(3'S,1R,2S,3R,6S)-2-(3'-hydroxy-3'-cyclohexylprop-1'-ynyl)-3-hydroxy-6-methylbicyclo[4.2.0]octan-7-one;
(3'S,1S,2R,3S,6R)-2-(3'hydroxy-3'-cyclohexylprop-1'-ynyl)-3-hydroxy-6-methylbicyclo[4.2.0]octan-7-one;
(3'S,1S,2R,3S,6R)-2-(3'-hydroxy-3'cyclohexylprop-1'-ynyl)-3-hydroxy-6-ethylbicyclo[4.2.0]octan-7-one;
(3'S,1R,2S,3R,6R)-2-(3'-hydroxy-3'-cyclohexylprop-1'-ynyl)-3-hydroxy-6-isopropylbicyclo[4.2.0]octan-7-one;
(3'S,1S,2R,3S,6S)-2-(3'-hydroxy-3'-cyclohexylprop-1'-ynyl)-3-hydroxy-6-isopropylbicyclo[4.2.0]octan-7-one;
(3'S,1R,2S,3R,6S)-2-(3'-hydroxy-3'-cyclohexylprop-1'-ynyl)-3-hydroxy-6-n-hexylbicyclo[4.2.0]octan-7-one;
(3'S,1S,2R,3S,6R)-2-(3'-hydroxy-3'-cyclohexylprop-1'-ynyl)-3-hydroxy-6-n-hexylbicyclo[4.2.0]octan-7-one;
(3'S,1R,2S,3R,6S)-2-(3'-hydroxy-4'-cyclohexylbut-1'-ynyl)-3-hydroxy-6-methylbicyclo[4.2.0]octan-7-one;
(3'S,1S,2R,3S,6R)-2-(3'-hydroxy-4'-cyclohexylbut-1'-ynyl)-3-hydroxy-6-methylbicyclo[4.2.0]octan-7-one;
(3'S,1R,2S,3R,6S)-2-(3'-hydroxy-4'-cyclohexylbut-1'-ynyl)-3-hydroxy-6-ethylbicyclo[4.2.0]octan-7-one;
(3'S,1S,2R,3S,6R)-2-(3'-hydroxy-4'-cyclohexylbut-1'-ynyl)-3 hydroxy-6-ethylbicyclo[4.2.0]octan-7-one;
(3'S,1R,2S,3R,6R)-2-(3'-hydroxy-4'-cyclohexylbut-1'-ynyl)-3-hydroxy-6-isopropylbicyclo[4.2.0]octan-7-one;
(3'S,1S,2R,3S,6S)-2-(3'-hydroxy-4'-cyclohexylbut-1'-ynyl)-3-hydroxy-6-isopropylbicyclo[4.2.0]octan-7-one;
(3'S,1R,2S,3R,6S)-2-(3'-hydroxy-4'-cyclohexylbut-1'-ynyl)-3-hydroxy-6-n-hexylbicyclo[4.2.0]octan-7-one;
(3'S,1S,2R,3S,6R)-2-(3'-hydroxy-4'-cyclohexylbut-1'-ynyl)-3-hydroxy-6-n-hexylbicyclo[4.2.0]octan-7-one;
(3'S,1R,2S,3R,6S)-2-(3'-hydroxy-4'-cyclopentylbut-1'-ynyl)-3-hydroxy-6-methylbicyclo[4.2.0]octan-7-one;
(3'S,1S,2R,3S,6R)-2-(3'-hydroxy-4'-cyclopentylbut-1'-ynyl)-3-hydroxy-6-methylbicyclo[4.2.0]octan-7-one;
(3'S,1R,2S,3R,6S)-2-(3'-hydroxy-4'-cyclopentylbut-1'-ynyl)-3-hydroxy-6-ethylbicyclo[4.2.0]octan-7-one;
(3'S,1S,2R,3S,6R)-2-(3'-hydroxy-4'-cyclopentylbut-1'-ynyl)-3-hydroxy-6-ethylbicyclo[4.2.0]octan-7-one;
(3'S,1R,2S,3R,6R)-2-(3'-hydroxy-4'-cyclopentylbut-1'-ynyl)-3-hydroxy-6-isopropylbicyclo[4.2.0]octan-7-one;
(3'S,1S,2R,3S,6S)-2-(3'-hydroxy-4'-cyclopentylbut-1'-ynyl)-3-hydroxy-6-isopropylbicyclo[4.2.0]octan-7-one;
(3'S,1R,2S,3R,6S)-2-(3'-hydroxy-4'-cyclopentylbut-1'-ynyl)-3-hydroxy-6-n-hexylbicyclo[4.2.0]octan-7-one;
(3'S,1S,2R,3S,6R)-2-(3'-hydroxy-4'-cyclopentylbut-1'-ynyl)-3-hydroxy-6-n-hexylbicyclo[4.2.0]octan-7-one;
(3'S,1R,2S,3R,6S)-2-(3'-hydroxydec-1'-ynyl)-3-hydroxy-6-methylbicyclo[4.2.0]octan-7-one;
(3'S,1S,2R,3S,6R)-2-(3'-hydroxydec-1'-ynyl)-3-hydroxy-6-methylbicyclo[4.2.0]octan-7-one;
(3'S,1R,2S,3R,6S)-2-(3'-hydroxydec-1'-ynyl)-3-hydroxy-6-ethylbicyclo[4.2.0]octan-7-one;
(3'S,1S,2R,3S,6R)-2-(3'-hydroxydec-1'-ynyl)-3-hydroxy-6-ethylbicyclo[4.2.0]octan-7-one;
(3'S,1R,2S,3R,6R)-2-(3'-hydroxydec-1'-ynyl)-3-hydroxy-6-isopropylbicyclo[4.2.0]octan-7-one;
(3'S,1S,2R,3S,6S)-2-(3'-hydroxydec-1'-ynyl)-3-hydroxy-6-isopropylbicyclo[4.2.0]octan-7-one;
(3'S,1R,2S,3R,6S)-2-(3'-hydroxydec-1'ynyl)-3-hydroxy-6-n-hexylbicyclo[4.2.0]octan-7-one;
(3'S,1S,2R,3S,6R)-2-(3'-hydroxydec-1'-ynyl)-3-hydroxy-6-n-hexylbicyclo[4.2.0]octan-7-one;
(3'S,1R,2S,3R,6S)-2-(3'-hydroxy-4'-phenoxybut-1'-ynyl)-3-hydroxy-6-methylbicyclo[4.2.0]octan-7-one;
(3'S,1S,2R,3S,6R)-2-(3'-hydroxy-4'-phenoxybut-1'-ynyl)-3-hydroxy-6-methylbicyclo[4.2.0]octan-7-one;
(3'S,1R,2S,3R,6S)-2-(3'-hydroxy-4'-phenoxybut-1'-ynyl)-3-hydroxy-6-ethylbicyclo[4.2.0]octan-7-one;
(3'S,1S,2R,3S,6R)-2-(3'-hydroxy-4'-phenoxybut-1'-ynyl)-3-hydroxy-6-ethylbicyclo[4.2.0]octan-7-one;
(3'S,1R,2S,3R,6R)-2-(3'-hydroxy-4'-phenoxybut-1'-ynyl)-3-hydroxy-6-isopropylbicyclo[4.2.0]octan-7-one;

(3'S,1S,2R,3S,6S)-2-(3'-hydroxy-4'-phenoxybut-1'-ynylynyl)-3-hydroxy-6-isopropylbicyclo[4.2.0]octan-7-one;

(3'S,1R,2S,3R,6S)-2-(3'-hydroxy-4'-phenoxybut-1'-ynyl)-3-hydroxy-6-n-hexylbicyclo[4.2.0]octan-7-one;

(3'S,1S,2R,3S,6R)-2-(3'-hydroxy-4'-phenoxybut-1'-ynyl)-3-hydroxy-6-n-hexylbicyclo[4.2.0]octan-7-one;

(3'S,1R,2S,3R,6S)-2-(3'-hydroxy-4'-endo-bicyclo[3.1.0]hex-6-yl)but-1'-ynyl)-3-hydroxy-6-methylbicyclo[4.2.0]octan-7-one;

(3'S,1S,2R,3S,6R) 2-(3'-hydroxy-4'-endo-bicyclo[3.1.0]hex-6-yl)but-1'-ynyl)-3-hydroxy-6-methylbicyclo[4.2.0]octan-7-one;

(3'S,1R,2S,3R,6S)-2-(3'-hydroxy-4'-endo-bicyclo[3.1.0]hex-6-yl)but-1'-ynyl)-3-hydroxy-6-ethylbicyclo[4.2.0]octan-7-one;

(3'S,1S,2R,3S,6R)-2-(3'-hydroxy-4'-endo-bicyclo[3.1.0]hex-6-yl)but-1'-ynyl)-3-hydroxy-6-ethylbicyclo[4.2.0]octan-7-one;

(3'S,1R,2S,3R,6R)-2-(3'-hydroxy-4'-endo-bicyclo[3.1.0]hex-6-yl)but-1'-ynyl)-3-hydroxy-6-isopropylbicyclo[4.2.0]octan-7-one;

(3'S,1S,2R,3S,6S)-2-(3'-hydroxy-4'-endo-bicyclo[3.1.0]hex-6-yl)but-1'-ynyl)-3-hydroxy-6-isopropylbicyclo[4.2.0]octan-7-one;

(3'S,1R,2S,3R,6S)-2-(3'-hydroxy-4'-endo-bicyclo[3.1.0]hex-6-yl)but-1'-ynyl)-3-hydroxy-6-n-hexylbicyclo[4.2.0]octan-7-one; and (3'S,1S,2R,3S,6R)-2-(3'-hydroxy-4'-endo-bicyclo[3.1.0]hex-6-yl)but-1'-ynyl)-3-hydroxy-6-n-hexylbicyclo[4.2.0]octan-7-one.

PREPARATION 23

Preparation of (3'S,1S,2S,3R,6S)-2-(3'-tertbutyldimethylsilyloxy-3'-cyclohexylprop-1'-ynyl)-3-tert-butyldimethylsilyloxy-6,8-dimethylbicyclo[4.2.0]-octan-7-one and Related Compounds of Formulas (21)

A.

(1) A solution of 1M lithium hexamethyldisilazane (0.87 ml) in tetrahydrofuran was cooled to −78° C., and a solution of 671 mg of (3'S,1R,2S,3R,6S)-2-(3'-tert butyldimethylsilyloxy-3'-cyclohexylprop-1'-ynyl)-3-tert-butyldimethylsilyloxy-6-methylbicyclo[4.2.0]octan-7-one, prepared as shown in Preparation 22 A(1), in 10 ml of tetrahydrofuran was added dropwise. The reaction mixture was stirred at −78° C. for 30 minutes, then 1 ml of methyl iodide in 0.5 ml of hexamethylphosphoramide added in one portion. The reaction mixture was stirred at −78° C. for 1 hour, then allowed to warm slowly to room temperature. After stirring for 2 hours, saturated ammonium chloride was added, the mixture extracted with ethyl acetate, and the extracts dried over anhydrous sodium sulfate. Solvent was removed under reduced pressure, and the residue chromatographed on silica gel, eluting with 2% ethyl acetate in hexane, to give 250 mg of (3'S,1S,2S,3R,6S)-2-(3'-tert-butyldimethylsilyloxy-3'-cyclohexylprop-1'-ynyl)-3-tert-butyldimethylsilyloxy-6,8-dimethylbicyclo[4.2.0]octan-7-one, the compound of formula (21).

(2) A solution of 150 mg of (3'S,1S,2S,3R,6S)-2-(3'-tert-butyldimethylsilyloxy-3'-cyclohexylprop-1'ynyl)-3-tert-butyldimethylsilyloxy-6-methylbicyclo[4.2.0]octan-7-one, prepared as shown in A(1) above, 10 ml of acetonitrile and 5 ml of 2N sulfuric acid was stirred at room temperature for 16 hours. The reaction was quenched by neutralization at room temperature with aqueous sodium bicarbonate and the reaction mixture extracted with diethyl ether. The extracts were dried with magnesium sulfate, the solvent removed under reduced pressure and the residue chromatographed on silica gel, eluting with 70% ethyl acetate in hexane, to give (3'S,1S,2S,3R,6S)-2-(3'-hydroxy-3'-cyclohexylprop-1'-ynyl)-3 hydroxy-6,8-dimethylbicyclo[4.2.0]octan-7-one, the compound of formula (23).

B. Similarly, starting with the appropriate compound of formula (20) in place of (3'S,1R,2S,3R,6S)-2-(3'-tert-butyldimethylsilyloxy-3'-cyclohexylprop-1'ynyl)-3-tert-butyldimethylsilyloxy-6-methylbicyclo[4.2.0]octan-7-one and optionally replacing methyl iodide with the appropriate alkyl halide, and following the procedure of paragraphs A(1) and A(2), the following compounds of formula (22) are prepared:

(3'S,1R,2R,3S,6R)-2-(3'-hydroxy-3'-cyclohexylprop-1'-ynyl)-3-hydroxy-6,8-dimethyl-bicyclo[4.2.0]octan-7-one;

(3'S,1S,2S,3R,6S)-2-(3'-hydroxy-4'-cyclohexylbut-1'-ynyl)-3-hydroxy-6,8-dimethylbicyclo[4.2.0]octan-7-one;

(3'S,1R,2R,3S,6R)-2-(3'-hydroxy-4'-cyclohexylbut-1'-ynyl)-3-hydroxy-6,8-dimethylbicyclo[4.2.0]octan-7-one;

(3'S,1S,2S,3R,6S)-2-(3'-hydroxy-4'-cyclopentylbut-1'-ynyl)-3-hydroxy-6,8-dimethylbicyclo[4.2.0]octan-7-one;

(3'S,1R,2R,3S,6R)-2-(3'-hydroxy-4'-cyclopentylbut-1'-ynyl)-3-hydroxy-6,8-dimethylbicyclo[4.2.0]octan-7-one;

(3'S,1S,2S,3R,6S)-2-(3'-hydroxydec-1'-ynyl)-3-hydroxy-6,8-dimethylbicyclo[4.2.0]octan-7-one;

(3'S,1R,2R,3S,6R)-2-(3'-hydroxydec-1'-ynyl)-3-hydroxy-6,8-dimethylbicyclo[4.2.0]octan-7-one;

(3'S,1S,2S,3R,6S)-2-(3'-hydroxy-4'-phenoxybut-1'-ynyl)-3-hydroxy-6,8-dimethylbicyclo[4.2.0]octan-7-one;

(3'S,1R,2R,3S,6R)-2-(3'-hydroxy-4'-phenoxybut-1'-ynyl)-3-hydroxy-6,8-dimethylbicyclo[4.2.0]octan-7-one;

(3'S,1S,2S,3R,6S)-2-(3'-hydroxy-3'-cyclohexylprop-1'-ynyl)-3-hydroxy-6-methyl-8-ethylbicyclo[4.2.0]octan-7-one;

(3'S,1R,2R,3S,6R)-2-(3'-hydroxy-3'-cyclohexylprop-1'-ynyl)-3-hydroxy-6-methyl-8-ethylbicyclo[4.2.0]octan-7-one;

(3'S,1S,2S,3R,6S)-2-(3'-hydroxy-4'-cyclohexylbut-1'-ynyl)-3-hydroxy-6-methyl-8-ethylbicyclo[4.2.0]octan-7-one;

(3'S,1R,2R,3S,6R)-2-(3'-hydroxy-4'-cyclohexylbut-1'ynyl)-3-hydroxy-6-methyl-8-ethylbicyclo[4.2.0]octan-7-one;

(3'S,1S,2S,3R,6S)-2-(3'-hydroxydec-1'-ynyl) 3-hydroxy-6-methyl-8-ethylbicyclo[4.2.0]octan-7-one;

(3'S,1R,2R,3S,6R)-2-(3'-hydroxydec-1'-ynyl)-3-hydroxy-6-methyl-8-ethylbicyclo[4 2.0]octan-7-one;

(3'S,1S,2S,3R,6S)-2-(3'-hydroxy-4'-phenoxybut-1'-ynyl)-3-hydroxy-6-methyl-8-ethylbicyclo[4.2.0]octan-7-one;

(3'S,1R,2R,3S,6R)-2-(3'-hydroxy-4'-phenoxybut-1'-ynyl)-3-hydroxy-6-methyl-8-ethylbicyclo[4.2.0]octan-7-one;

(3'S,1S,2S,3R,6S)-2-(3'-hydroxy-3'-cyclohexylprop-1'-ynyl)-3-hydroxy-6-methyl-8-isobutylbicyclo[4 2.0]octan-7-one;

(3'S,1R,2R,3S,6R)-2-(3'-hydroxy-3'-cyclohexylprop-1'-ynyl)-3-hydroxy-6-methyl-8-isobutylbicyclo[4.2.0]octan7-one;

(3'S,1S,2S,3R,6S)-2-(3'-hydroxy-3'-cyclohexylprop-1'-ynyl)-3-hydroxy-6-methyl-8-n-hexylbicyclo[4.2.0]octan-7-one;

(3'S,1R,2R,3S,6R)-2-(3'-hydroxy-3'-cyclohexylprop-1'-ynyl)-3-hydroxy-6-methyl-8-n-hexylbicyclo[4.2.0]octan-7-one;

(3'S,1S,2S,3R,6S)-2-(3'-hydroxy-3'-cyclohexylprop-1'-ynyl)-3-hydroxy-6-ethyl-8-methylbicyclo[4.2.0]octan-7-one;

(3'S,1R,2R,3S,6R)-2-(3'-hydroxy-3'-cyclohexylprop-1'-ynyl)-3-hydroxy-6-ethyl-8-methylbicyclo[4.2.0]octan-7-one;

(3'S,1S,2S,3R,6S)-2-(3'-hydroxy-3'-cyclohexylprop-1'-ynyl)-3-hydroxy-6,8-diethylbicyclo[4.2.0]octan-7-one;

(3'S,1R,2R,3S,6R)-2-(3'-hydroxy-3'-cyclohexylprop-1'-ynyl)-3-hydroxy-6,8-diethylbicyclo[4.2.0]octan-7-one;

(3'S,1S,2S,3R,6S)-2-(3'-hydroxy-3'-cyclohexylprop-1'-ynyl)-3-hydroxy-6-ethyl-8-isobutylbicyclo[4.2.0]octan-7-one;

(3'S,1R,2R,3S,6R)-2-(3'-hydroxy-3'-cyclohexylprop-1'-ynyl)-3-hydroxy-6-ethyl-8-isobutylbicyclo[4.2.0]octan-7-one;

(3'S,1S,2S,3R,6R)-2-(3'-hydroxy-3'-cyclohexylprop-1'-ynyl)-3-hydroxy-6-isopropyl-8-methylbicyclo[4.2.0]octan-7-one;

(3'S,1R,2R,3S,6S)-2-(3'-hydroxy-3'-cyclohexylprop-1'-ynyl)-3-hydroxy-6-isopropyl-8-methylbicyclo[4.2.0]octan-7-one;

(3'S,1S,2S,3R,6R)-2-(3'-hydroxy-3'-cyclohexylprop-1'-ynyl)-3-hydroxy-6-isopropyl-8-ethylbicyclo[4.2.0]octan-7-one;

(3'S,1R,2R,3S,6S)-2-(3'-hydroxy-3'-cyclohexylprop-1'-ynyl)-3-hydroxy-6-isopropyl-8-ethylbicyclo[4.2.0]octan-7-one;

(3'S,1S,2S,3R,6R)-2-(3'-hydroxy-3'-cyclohexylprop-1'-ynyl)-3-hydroxy-6-isopropyl-8-isobutylbicyclo[4.2.0]octan-7-one;

(3'S,1R,2R,3S,6S)-2-(3'-hydroxy-3'-cyclohexylprop-1'-ynyl)-3-hydroxy-6-isopropyl-8-isobutylbicyclo[4.2.0]octan-7-one;

(3'S,1S,2S,3R,6S)-2-(3'-hydroxy-3'-cyclohexylprop-1'-ynyl)-3-hydroxy-6-n-hexyl-8-methylbicyclo[4.2.0]octan-7-one;

(3'S,1R,2R,3S,6R)-2-(3'-hydroxy-3'-cyclohexylprop-1'-ynyl)-3-hydroxy-6-n-hexyl-8-methylbicyclo[4.2.0]octan-7-one;

(3'S,1S,2S,3R,6S)-2-(3'-hydroxy-3'-cyclohexylprop-1'-ynyl)-3-hydroxy-6-n-hexyl-8-n-hexylbicyclo[4.2.0]octan-7-one; and (3'S,1R,2R,3S,6R)-2-(3'-hydroxy-3'-cyclohexylprop-1'-ynyl)-3-hydroxy-6-n-hexyl-8-n-hexylbicyclo[4.2.0]octan-7-one.

EXAMPLE 1

Preparation of
(Z)-(3'S,1S,2R,3S,6R)-4-[2-(3'-hydroxy-3'-cyclohexylprop-1'-ynyl)-3-hydroxy-6-ethylbicyclo[4.2.0]oct-7-ylidene]butanoic acid and
(E)-(3'S,1S,2R,3S,6R)-4-[2-(3'-hydroxy-3'cyclohexylprop-1'-ynyl)-3-hydroxy-6-ethylbicyclo[4.2.0]-oct-7-ylidene]butanoic acid and Related Compounds of Formulas (1), (2) and (3) in which $R_1$ is $-CO_2H$.

A. A stock solution of dimsyl sodium was prepared by dissolving 1.44 g sodium hydride in 30 ml dimethyl sulfoxide at 65° C. under nitrogen. To a stirred slurry of 773 mg of 3-carboxypropyltriphenylphosphonium bromide in 25 ml dimethyl sulfoxide under nitrogen was added 15 ml of the stock solution of dimsyl sodium. After 20 min at 23° C. a solution of 110 mg of (3'S,1S,2R,3S,6R)-2-(3'-hydroxy-3'-cyclohexylprop-1'-ynyl)-3-hydroxy-6-ethylbicyclo[4.2.0]octane-7-one in 4 ml of dimethyl sulfoxide was added in one portion. After 2 hours at 60° C. the mixture was poured on to 75 ml 5% sodium carbonate solution. This mixture was washed with two 60 ml portions of ethyl acetate and was then acidified with 6N hydrochloric acid. The aqueous layer was extracted three times with 50 ml portions of diethyl ether. The combined ether extract was concentrated to 20 ml and this was kept at −20° C. for 2 h. The resulting precipitate was filtered and was discarded. Evaporation of the filtrate gave 1.73 mg of an oil. This material was purified by silica gel flash chromatography using a solvent mixture of acetic acid-methanol-methylene chloride (0.1:5:95) to give 337 mg of an oil. Further purification by HPLC using a solvent mixture of acetic acid-isopropanol-hexane (0.1:8:92) separated the product mixture into the individual (E) and (Z) isomers of formula (1).

The first eluted was:
(E)-(3'S,1S,2R,3S,6R)-4-[2-(3'-hydroxy-3'-cyclohexylprop-1'-ynyl)-3-hydroxy-6-ethylbicyclo[4.2.0]oct-7-ylidene]butanoic acid, 48 mg. CIMS m/z 374(M+)

The second eluted was:
(Z)-(3'S,1S,2R,3S,6R)-4-[2-(3'-hydroxy-3'-cyclohexylprop-1'-ynyl)-3-hydroxy-6-ethylbicyclo[4.2.0]oct-7-ylidene]butanoic acid, 360 mg. CIMS m/z 374(M+) $[\alpha]_D^{25} = -60.03$ (C=0.578, CHCl$_3$).

B. Similarly, starting with the appropriate compound of formula (16), (17), (22), (23), (28), (29), (32) or (33) in place of (3'S,1S,2R,3S,6R) 2-(3'-hydroxy-3'-cyclohexylprop-1'ynyl)-3 hydroxy-6-ethylbicyclo[4.2.0]octane-7-one in paragraph A above, obtained as described in Preparations 13, 16 and 17, and optionally replacing 3-carboxypropyltriphenylphosphonium bromide with other appropriate carboxyalkyltriphenylphosphonium bromides, the following compounds of formulas (1), (2) or (3) were obtained:

(E)-(3'S,1R,2S,3R,6S)-4 [2-(3'-hydroxy-3'-cyclohexylprop-1'-ynyl)-3-hydroxy-6-ethylbicyclo[4.2.0]oct-7-ylidene]butanoic acid;

(Z)-(3'S,1R,2S,3R,6S)-4-[2-(3'-hydroxy-3'-cyclohexylprop-1'-ynyl)-3-hydroxy-6-ethylbicyclo[4.2.0]oct-7-ylidene]butanoic acid;
$[\alpha]_D^{25} = +94.51$ (C=0.2667, CHCl$_3$).

(Z)-(3'S,1R,2S,3R,6S)-4-[2-(3'hydroxy-3'-cyclohexylprop-1'-ynyl)-3-hydroxy-6-methylbicyclo[4.2.0]oct-7-ylidene]butanoic acid, ms 360 (M+);

(E)-(3'S,1R,2S,3R,6S)-4-[2-(3'-hydroxy-3'-cyclohexyl-prop-1'-ynyl)-3-hydroxy-6-methylbicyclo[4.2.0]oct-7-ylidene]butanoic acid, ms 360 (M+);

(Z)-(3'S,1S,2R,3S,6R)-4-[2-(3'-hydroxy-3'-cyclohexyl-prop-1'-ynyl)-3-hydroxy-6-methylbicyclo[4.2.0]oct-7-ylidene]butanoic acid, ms 360 (M+);

(E)-(3'S,1S,2R,3S,6R)-4-[2-(3'-hydroxy-3'-cyclohexyl-prop-1'-ynyl)-3-hydroxy-6-methylbicyclo[4.2.0]oct-7-ylidene]butanoic acid, ms 360 (M+);

(Z)-(3'S,1R,2S,3R,6S)-5-[2-(3'-hydroxy-3'-cyclohexyl-prop-1'-ynyl)-3-hydroxy-6-methylbicyclo[4.2.0]oct-7-ylidene]pentanoic acid, ms 392 (MNH$_4$+);

(Z) (3'S,1S,2R,3S,6R)-5-[2-(3'-hydroxy-3'-cyclohexyl-prop-1'ynyl)-3-hydroxy-6-methylbicyclo[4.2.0]oct-7-ylidene]pentanoic acid, ms 392 (MNH$_4$+);

(Z) (3'S,1S,2R,3S,6R)-6-[2-(3'-hydroxy-3'-cyclohexyl-prop-1'-ynyl)-3-hydroxy-6-methylbicyclo[4.2.0]oct-7-ylidene]hexanoic acid, ms 406 (MNH$_4$+);

(Z)-(3'S,1S,2R,3S,6R)-4-[2-(3'-hydroxy-3'-cyclohexyl-prop-1'-ynyl)-3-hydroxy-6-methyl-8-exo-methylbicyclo[4.2.0]oct-7-ylidene]butanoic acid;
$[\alpha]_D^{25} = -30.92$ (C=0.5691, CHCl$_3$)

(Z)-(3'-S,1S,2R,3S,6R)-4-[2-(3'-hydroxy-3'-cyclohexyl-prop-1'ynyl)-3-hydroxy-6-methyl 8-endo-methyl-bicyclo[4.2.0]oct-7-ylidene]butanoic acid;
$[\alpha]_D^{25} = -62.57$ (C=0.3036, CHCl$_3$)

(E)-(3'S,1S,2R,3S,6R)-4-[2-(3'-hydroxy-3'-cyclohexyl-prop-1'-ynyl)-3-hydroxy-6-methyl-8-endo-methyl-bicyclo[4.2.0]oct-7-ylidene]butanoic acid;

(E)-(3'S,1S,2R,3S,6R)-4-[2-(3'-hydroxy-3'-cyclohexyl-prop-1'-ynyl)-3-hydroxy-6-methyl-8-exo-methylbicyclo[4.2.0]oct-7-ylidene]butanoic acid;
$[\alpha]_D^{25} = -67.33$ (C=0.3718, CHCl$_3$)

(Z) (3'S,1R,2S,3R,6S)-4-[2-(3'-hydroxy-3'-cyclohexyl-prop-1'-ynyl)-3-hydroxy-6-methyl-8-endo-methyl-bicyclo[4.2.0]oct-7-ylidene]butanoic acid; MS 374 (M+);

(Z)-(3'S,1R,2S,3R,6S)-4-[2-(3'-hydroxy-3'-cyclohexyl-prop-1'-ynyl)-3-hydroxy-6-methyl-8-exo-methylbicyclo[4.2.0]oct-7-ylidene]butanoic acid, ms 392 (MNH$_4$+), and (E)-(3'S,1R,2S,3R,6S)-4-[2-(3'-hydroxy-3'-cyclohexyl-prop-1,-ynyl)-3-hydroxy-6-methyl-8-exo methylbicyclo[4.2.0]oct-7-ylidene]butanoic acid, ms 392 (MNH$_4$+).

C. Similarly, starting with the appropriate compound of formula (16), (17), (22), (23), (28), (29), (32) or (33) in place of (3'S,1S,2R,3S,6R)-2-(3'-hydroxy-3'-cyclohexylprop-1'-ynyl)-3-hydroxy-6-ethylbicyclo[4.2.0]octane-7-one in paragraph A above, obtained as described in Preparations 13, 16 and 17, and optionally replacing 3-carboxypropyltriphenylphosphonium bromide with other appropriate carboxyalkyltriphenylphosphonium bromides, the following compounds of formulas (1), (2) or (3) are obtained as the E isomer and the Z isomer, where Y is hydrogen or Y is lower alkyl (exo or endo):

(3'R,1S,2S,3S,6R)-4-[2-(3'-hydroxy-3'-cyclohexylprop-1-yl)-3-hydroxy-6-methylbicyclo[4.2.0]oct-7-ylidene]butanoic acid;

(3'R,1S,2R,3S,6R)-4-[2-(3'-hdyroxy-3'-cyclohexylprop-1'-ynyl)-3-hdyroxy-6-methylbicyclo[4.2.0]oct-7-ylidene]butanoic acid;

(3'R,1S,2R,3S,6R)-4-[2-(3'-hydroxy-3'-cyclohexylprop-1'-ynyl)-3-hydroxy-6-ethylbicyclo[4.2.0]oct-7-ylidene]butanoic acid;

(3'S,1S,2R,3S,6R)-5-[2-(3'-hydroxy-3'-cyclohexylprop-1'-ynyl)-3-hydroxy-6-ethylbicyclo[4.2.0]oct-7-ylidene]pentanoic acid;

(3'S,1S,2R,3S,6R)-6-[2-(3'-hydroxy-3'-cyclohexylprop-1'-ynyl)-3-hydroxy-6-ethylbicyclo[4.2.0]oct-7-ylidene]hexanoic acid;

(3'S,1R,2S,3R,6R)-4-[2-(3'-hydroxy-3'cyclohexylprop-1'-ynyl)-3-hydroxy-6-isopropylbicyclo[4.2.0]oct-7-ylidene]butanoic acid;

(3'S,1S,2R,3S,6S)-4-[2-(3'-hydroxy-3'-cyclohexylprop-1'-ynyl)-3-hydroxy-6-isopropylbicyclo[4.2.0]oct-7ylidene]butanoic acid;

(3'S,1R,2S,3R,6S)-4-[2-(3'-hydroxy-3'-cyclohexylprop-1'-ynyl)-3-hydroxy-6-n-hexylbicyclo[4.2.0]oct-7-ylidene]butanoic acid;

(3'S,1S,2R,3S,6R)-4-[2-(3'-hydroxy-3'-cyclohexylprop-1'-ynyl)-3-hydroxy-6-n-hexylbicyclo[4.2.0]oct-7-ylidene]butanoic acid;

(3'S,1R,2S,3R,6S)-4-[2-(3'-hydroxy-4'-cyclohexylbut-1'ynyl)-3-hydroxy-6-methylbicyclo[4.2.0]oct-7-ylidene]butanoic acid;

(3'S,1S,2R,3S,6R)-4-[2-(3'-hydroxy-4'-cyclohexylbut-1'-ynyl)-3-hydroxy-6-methylbicyclo[4.2.0]oct-7-ylidene]butanoic acid;

(3'S,1R,2S,3R,6S)-4-[2-(3'-hydroxy-4'-cyclopentylbut-1'-ynyl)-3-hydroxy-6-methylbicyclo[4.2.0]oct-7-ylidene]butanoic acid;

(3'S,1S,2R,3S,6R)-4-[2-(3'-hydroxy-4'-cyclopentylbut-1'ynyl)-3-hydroxy-6-methylbicyclo[4.2.0]oct-7-ylidene]butanoic acid;

(3'S,1R,2S,3R,6S)-4-[2-(3'-hydroxydec-1'-ynyl)-3-hydroxy-6-methylbicyclo[4.2.0]oct-7-ylidene]-butanoic acid;

(3'S,1S,2R,3S,6R)-4-[2-(3'-hydroxydec-1'-ynyl)-3-hydroxy-6-methylbicyclo[4.2.0]oct-7-ylidene]-butanoic acid;

(3'S,1R,2S,3R,6S)-4-[2-(3'-hydroxy-4'-phenoxybut-1'-ynyl)-3-hydroxy-6-methylbicyclo[4.2.0]oct-7-ylidene]butanoic acid;

(3'S,1S,2R,3S,6R)-4-[2-(3'-hydroxy-4'-phenoxybut-1'-ynyl)-3-hydroxy-6-methylbicyclo[4.2.0]oct-7-ylidene]butanoic acid;

(3'S,1R,2S,3R,6S)-4-[2-(3'-hydroxy-4'-(endo-bicyclo[3.1.0]hex-6-yl)but-1'-ynyl)-3-hydroxy-6-methylbicyclo[4.2.0]oct-7-ylidene]butanoic acid;

(3'S,1S,2R,3S,6R)-4-[2-(3'-hydroxy-4'(endo-bicyclo[3.1.0]hex-6-yl)but-1'-ynyl)-3-hydroxy-6-methylbicyclo[4.2.0]oct-7-ylidene]butanoic acid;

(3'R,1S,2R,3S,6R)-4-[2-(3'-hydroxy-3'-cyclohexylprop-1'-ynyl)-3-hydroxy-6,8-dimethylbicyclo[4.2.0]oct-7-ylidene]butanoic acid:

(3'S,1S,2R,3S,6R)-5-[2-(3'-hydroxy-3'-cyclohexylprop-1'-ynyl)-3-hydroxy-6,8-dimethylbicyclo[4.2.0]oct-7-ylidene]pentanoic acid;

(3'S,1S,2R,3S,6R)-6-[2-(3'-hydroxy-3'-cyclohexylprop-1'-ynyl)-3-hydroxy-6,8-dimethylbicyclo[4.2.0]oct-7-ylidene]hexanoic acid;

(3'S,1R,2S,3R,6S)-4-[2-(3'-hydroxy-4'-cyclohexylbut-1'ynyl)-3-hydroxy-6,8-dimethylbicyclo[4.2.0]oct-7-ylidene]butanoic acid;

(3'S,1S,2R,3S,6R)-4-[2-(3'-hydroxy-4'-cyclohexylbut-1'ynyl)-3-hydroxy-6,8-dimethylbicyclo[4.2.0]oct-7-ylidene]butanoic acid;

(3'S,1R,2S,3R,6S)-4[2-(3'-hydroxy-4'-cyclopentylbut1'-ynyl)-3-hydroxy-6,8-dimethylbicyclo[4.2.0]oct-7ylidene]butanoic acid;

(3'S,1S,2R,3S,6R)-4-[2-(3'-hydroxy-4'-cyclopentylbut-1'-ynyl)-3-hydroxy-6,8-dimethylbicyclo[4.2.0]oct-7-ylidene]butanoic acid;
(3'S,1R,2S,3R,6S)-4-[2-(3'-hydroxydec-1'-ynyl)-3-hydroxy-6,8-dimethylbicyclo[4.2.0]oct-7-ylidene]butanoic acid;
(3'S,1S,2R,3S,6R)-4-[2-(3'-hydroxydec-1'-ynyl)-3-hydroxy-6,8-dimethylbicyclo[4.2.0]oct-7-ylidene]butanoic acid;
(3'S,1R,2S,3R,6S)-4-[2-(3'-hydroxy-4'-phenoxybut-1'-ynyl)-3-hydroxy-6,8-dimethylbicyclo[4.2.0]oct-7-ylidene]butanoic acid;
(3'S,1S,2R,3S,6R)-4-[2-(3'-hydroxy-4'-phenoxybut-1'-ynyl)-3-hydroxy-6,8-dimethylbicyclo[4.2.0]oct-7-ylidene]butanoic acid;
(3'S,1R,2S,3R,6S)-4-[2-(3'-hydroxy-3'-cyclohexylprop-1'ynyl)-3-hydroxy-6-methyl-8-ethylbicyclo[4.2.0]oct-7-ylidene] butanoic acid;
(3'S,1S,2R,3S,6R)-4-[2-(3'-hydroxy-3'-cyclohexylprop-1'-ynyl)-3-hydroxy-6-methyl-8-ethylbicyclo[4.2.0]oct-7-ylidene]butanoic acid;
(3'S,1R,2S,3R,6S)-4-[2-(3'-hydroxy-4'-cyclohexylbut-1'-ynyl)-3-hydroxy-6-methyl-8-ethylbicyclo[4.2.0]oct-7-ylidene]butanoic acid;
(3'S,1S,2R,3S,6R)-4-[2-(3'-hydroxy-4'-cyclohexylbut-1'-ynyl)-3-hydroxy-6-methyl-8-ethylbicyclo[4.2.0]oct-7-ylidene]butanoic acid;
(3'S,1R,2S,3R,6S)-4-[2-(3'-hydroxydec-1'-ynyl)-3-hydroxy-6-methyl-8-ethylbicyclo[4.2.0]oct-7-ylidene]butanoic acid;
(3'S,1S,2R,3S,6R)-4-[2-(3'-hydroxydec-1'-ynyl)-3-hydroxy-6-methyl-8-ethylbicyclo[4.2.0]oct-7-ylidene]butanoic acid;
(3'S,1R,2S,3R,6S)-4-[2-(3'-hydroxy-4'-phenoxybut-1'-ynyl)-3-hydroxy-6-methyl-8-ethylbicyclo[4.2.0]oct-7-ylidene]butanoic acid;
(3'S,1S,2R,3S,6R)-4-[2-(3'-hydroxy-4'-phenoxybut-1'-ynyl)-3-hydroxy-6-methyl-8-ethylbicyclo[4.2.0]oct-7-ylidene]butanoic acid;
(3'S,1R,2S,3R,6S)-4-[2-(3'-hydroxy-3'-cyclohexylprop-1'ynyl)-3-hydroxy-6-methyl-8-isobutylbicyclo[4.2.0]oct-7-ylidene]butanoic acid;
(3'S,1S,2R,3S,6R)-4-[2-(3'-hydroxy-3'-cyclohexylprop-1'-ynyl)-3-hydroxy-6-methyl-8-isobutylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6-methyl-8-n-hexylbicyclo[4.2.0]oct-7-ylidene]butanoic acid;
(3'S,1S,2R,3S,6R)-4-[2-(3'-hydroxy-3'-cyclohexylprop-1'-ynyl)-3-hydroxy-6-methyl-8-n-hexylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6-ethyl-8-methylbicyclo[4.2.0]oct-7-ylidene]butanoic acid;
(3'S,1S,2R,3S,6R)-4-[2-(3'-hydroxy-3'-cyclohexylprop-1'-ynyl)-3-hydroxy-6-ethyl-8-methylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6,8-diethylbicyclo[4.2.0]oct-7-ylidene]butanoic acid;
(3'S,1S,2R,3S,6R)-4-[2-(3'-hydroxy-3'-cyclohexylprop-1'-ynyl)-3-hydroxy-6,8-diethylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6-ethyl-8-isobutylbicyclo[4.2.0]oct-7-ylidene]butanoic acid;
(3'S,1S,2R,3S,6R)-4-[2-(3'-hydroxy-3'-cyclohexylprop-1'-ynyl)-3-hydroxy-6-ethyl-8-isobutylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6-isopropyl-8-methylbicyclo[4.2.0]oct-7-ylidene]butanoic acid;
(3'S,1S,2R,3S,6S)-4-[2-(3'-hydroxy-3'-cyclohexylprop-1'-ynyl)-3-hydroxy-6-isopropyl-8-methylbicyclo[4.2.0]oct-7-ylidene]butanoic acid;
(3'S,1R,2S,3R,6R)-4-[2-(3'-hydroxy-3'-cyclohexylprop-1'-ynyl)-3-hydroxy-6-isopropyl-8-ethylbicyclo[4.2.0]oct-7-ylidene]butanoic acid;
(3'S,1S,2R,3S,6S)-4-[2-(3'-hydroxy-3'-cyclohexylprop-1'-ynyl)-3-hydroxy-6-isopropyl-8-ethylbicyclo[4.2.0]oct-7-ylidene]butanoic acid;
(3'S,1R,2S,3R,6R)-4-[2-(3'hydroxy-3'-cyclohexylprop-1'-ynyl)-3-hydroxy-6-isopropyl-8-isobutylbicyclo[4.2.0]oct-7-ylidene]butanoic acid;
(3'S,1S,2R,3S,6S)-4-[2-(3'-hydroxy 3'-cyclohexylprop-1'-ynyl)-3-hydroxy-6-isopropyl-8-isobutylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6-n-hexyl-8-methylbicyclo[4.2.0]oct-7-ylidene]butanoic acid;
(3'S,1S,2R,3S,6R)-4-[2-(3'-hydroxy-3'-cyclohexylprop-1'ynyl)-3-hydroxy-6-n-hexyl-8-methylbicyclo[4.2.0]oct-7-ylidene]butanoic acid;
(3'S,1R,2S,3R,6S)-4-[2-(3'-hydroxy-3'-cyclohexylprop-1'-ynyl)-3-hydroxy-6-n-hexyl-8-n-hexylbicyclo[4.2.0]oct-7-ylidene]butanoic acid; and
(3'S,1S,2R,3S,6R)-4-[2-(3'-hydroxy-3'-cyclohexylprop-1'-ynyl)-3-hydroxy-6-n-hexyl-8-n-hexylbicyclo[4.2.0]oct-7-ylidene]butanoic acid.

(1'E)-(3'S,1S,2S,3S,6R)-4-[2-(3'-hydroxy-3'-cyclohexylprop-1'-enyl)-3-hydroxy-6-methylbicyclo[4.2.0]oct-7-ylidene]butanoic acid;
(1'E)-(3'S,1S,2S,3S,6R)-5-[2-(3'-hydroxy-3'-cyclohexylprop-1'-enyl)-3-hydroxy-6-methylbicyclo[4.2.0]oct-7-ylidene]pentanoic acid;
(1'E) (3'S,1S,2S,3S,6R)-6-[2-(3'hydroxy-3'-cyclohexylprop-1'-enyl)-3-hydroxy-6-methylbicyclo[4.2.0]oct-7-ylidene]hexanoic acid;
(1'E) (3'S,1R,2R,3R,6S)-4-[2-(3'-hydroxy-3'-cyclohexylprop-1'-enyl)-3-hydroxy-6-methylbicyclo[4.2.0]oct-7-ylidene]butanoic acid;
(1'E)-(3'R,1S,2S,3S,6R)-4-[2-(3'-hydroxy-3'-cyclohexylprop-1'-enyl)-3-hydroxy-6-methylbicyclo[4.2.0]oct-7-ylidene]butanoic acid;
(1'E)-(3'S,1S,2S,3S,6R)-4-[2-(3'-hydroxy-3'-cyclohexylprop-1'-enyl)-3-hydroxy-6-ethylbicyclo[4.2.0]oct-7-ylidene]butanoic acid;
(1'E)-(3'S,1R,2R,3R,6S)-4-[2-(3'-hydroxy-3'-cyclohexylprop-1'-enyl)-3-hydroxy-6-ethylbicyclo[4.2.0]oct-7-ylidene]butanoic acid;
(1'E) (3'R,1S,2S,3S,6R)-4-[2-(3'-hydroxy-3'-cyclohexylprop-1'-enyl)-3-hydroxy-6-ethylbicyclo[4.2.0]oct-7-ylidene]butanoic acid;
(1'E)-(3'S,1S,2S,3S,6S)-4-[2-(3'-hydroxy-3'-cyclohexylprop-1'-enyl)-3-hydroxy-6-isopropylbicyclo[4.2.0]oct-7-ylidene]butanoic acid;
(1'E)-(3'R,1S,2S,3S,6S)-4-[2-(3'-hydroxy-3'-cyclohexylprop-1'-enyl)-3-hydroxy-6-isopropylbicyclo[4.2.0]oct-7-ylidene]butanoic acid;
(1'E)-(3'S,1S,2S,3S,6R)-4-[2-(3'-hydroxy-4'-cyclohexylbut-1'-enyl)-3-hydroxy-6-methylbicyclo[4.2.0]oct-7-ylidene]butanoic acid;

(1′E)-(3′R,1S,2S,3S,6R)-4-[2-(3′-hydroxy-4′-cyclohexylbut-1′-enyl)-3-hydroxy-6-methylbicyclo[4.2.0]oct-7-ylidene]butanoic acid;

(1′E)-(3′S,1S,2S,3S,6R)-4-[2-(3′-hydroxy-4′-cyclopentylbut-1′-enyl)-3-hydroxy-6-methylbicyclo[4.2.0]oct-7-ylidene]butanoic acid;

(1′E)-(3′R,1S,2S,3S,6R) -4-[2-(3′-hydroxy-4′-cyclopentylbut-1′enyl)-3-hydroxy-6-methylbicyclo[4.2.0]oct-7-ylidene]butanoic acid;

(1′E)-(3′S,1S,2S,3S,6R)-4-[2-(3′-hydroxydec-1′-enyl)-3-hydroxy-6-methylbicyclo[4.2.0]oct-7-ylidene]butanoic acid;

(1′E)-(3′R,1S,2S,3S,6R)-4-[2-(3′-hydroxydec-1′-enyl)-3-hydroxy-6-methylbicyclo[4.2.0]oct-7-ylidene]butanoic acid;

(1′E)-(3′S,1S,2S,3S,6R)-4-[2-(3′-hydroxy-4′-phenoxybut-1′-enyl)-3-hydroxy-6-methylbicyclo[4.2.0]oct-7-ylidene]butanoic acid;

(1′E)-(3′R,1S,2S,3S,6R)-4-[2-(3′-hydroxy-4′-phenoxybut-1′-enyl)-3-hydroxy 6-methylbicyclo[4.2.0]oct-7-ylidene]butanoic acid;

(1′E)-(3′S,1S,2S,3S,6R)-4-[2-(3′-hydroxy-4′-(endo-bicyclo[3.1.0]hex-6-yl)but-1′-enyl)-3-hydroxy-6-methylbicyclo[4.2.0]oct-7-ylidene]butanoic acid;

(1′E)-(3′R,1S,2S,3S,6R)-4-[2-(3′-hydroxy-4′-(endo-bicyclo[3.1.0]hex-6-yl)but-1′enyl)-3-hydroxy-6-methylbicyclo[4.2.0]oct-7-ylidene]butanoic acid;

(1′E)-(3′S,1R,2R,3R,6S)-4-[2-(3′-hydroxy-3′-cyclohexylprop-1′enyl)-3-hydroxy-6,8-dimethylbicyclo[4.2.0]oct-7-ylidene]butanoic acid;

(1′E)-(3′S,1S,2S,3S,6R)-4-[2-(3′-hydroxy-3′-cyclohexylprop-1′enyl)-3-hydroxy-6,8-dimethylbicyclo[4.2.0]oct-7-ylidene]pentanoic acid;

(1′E)-(3′S,1S,2S,3S,6R)-5-[2-(3′-hydroxy-3′-cyclohexylprop-1′-enyl)-3-hydroxy-6,8-dimethylbicyclo[4.2.0]oct-7-ylidene]butanoic acid;

(1′E)-(3′S,1S,2S,3S,6R)-6-[2-(3′-hydroxy-3′-cyclohexylprop-1′-enyl)-3-hydroxy-6,8-dimethylbicyclo[4 2.0]oct-7-ylidene]hexanoic acid;

(1′E)-(3′R,1S,2S,3S,6R)-4-[2-(3′-hydroxy-3′-cyclohexylprop-1′enyl)-3-hydroxy-6,8-dimethylbicyclo[4.2.0]oct-7-ylidene]butanoic acid;

(1′E)-(3′S,1S,2S,3S,6R)-4-[2-(3′-hydroxy-4′-cyclohexylbut-1′enyl)-3-hydroxy-6,8-dimethylbicyclo[4.2.0]oct-7-ylidene]butanoic acid;

(1′E)-(3′R,1S,2S,3S,6R)-4-[2-(3′-hydroxy-4′-cyclohexylbut-1′enyl)-3-hydroxy-6.8-dimethylbicyclo[4.2.0]oct-7-ylidene]butanoic acid;

(1′E)-(3′S,1S,2S,3S,6R)-4-[2-(3′-hydroxy-4′-cyclopentylbut-1′enyl)-3-hydroxy-6,8-dimethylbicyclo[4.2.0]oct-7-ylidene]butanoic acid;

(1′E)-(3′R,1S,2S,3S,6R)-4-[2-(3′-hydroxy-4′-cyclopentylbut-1′-enyl)-3-hydroxy-6,8-dimethylbicyclo[4.2.0]oct-7-ylidene]butanoic acid;

(1′E)-(3′S,1S,2S,3S,6R)-4-[2-(3′-hydroxy-4′-phenoxybut-1′-enyl)-3-hydroxy-6,8-dimethylbicyclo[4.2.0]oct-7-ylidene]butanoic acid;

(1′E)-(3′R,1S,2S,3S,6R)-4-[2-(3′-hydroxy-4′-phenoxybut1′-enyl)-3-hydroxy-6,8-dimethylbicyclo[4.2.0]oct-7-ylidene]butanoic acid;

(1′E)-(3′S,1S,2S,3S,6R)-4-[2-(3′-hydroxy-3′-cyclohexylprop-1′-enyl)-3-hydroxy-6-methyl-8-ethylbicyclo[4.2.0]oct-7-ylidene]butanoic acid;

(1′E)-(3′R,1S,2S,3S,6R)-4-[2-(3′-hydroxy-3′-cyclohexylprop-1′-enyl)-3-hydroxy-6-methyl-8-ethylbicyclo[4.2.0]oct-7-ylidene]butanoic acid;

(1′E)-(3′S,1S,2S,3S,6R)-4-[2-(3′-hydroxy-3′-cyclohexylprop-1′-enyl)-3-hydroxy-6-methyl-8-n-hexylbicyclo[4.2.0]oct-7-ylidene]butanoic acid;

(1′E)-(3′R,1S,2S,3S,6R)-4-[2-(3′-hydroxy-3′-cyclohexylprop-1′-enyl)-3-hydroxy-6-methyl-8-n-hexylbicyclo[4.2.0]oct-7-ylidene]butanoic acid;

(1′E)-(3′S,1S,2S,3S,6R)-4-[2-(3′-hydroxy-3′-cyclohexylprop-1′-enyl)-3-hydroxy-6-ethyl-8-methylbicyclo[4.2.0]oct-7-ylidene]butanoic acid;

(1′E)-(3′R,1S,2S,3S,6R)-4-[2-(3′-hydroxy-3′-cyclohexylprop-1′-enyl)-3-hydroxy-6-ethyl-8-methylbicyclo[4.2.0]oct-7-ylidene]butanoic acid;

(1′E)-(3′S,1S,2S,3S,6S)-4-[2-(3′-hydroxy-3′-cyclohexylprop-1′-enyl)-3-hydroxy-6-isopropyl-8-methylbicyclo[4.2.0]oct-7-ylidene]butanoic acid;

(1′E)-(3′S,1R,2S,3S,6S)-4-[2-(3′-hydroxy-3′-cyclohexylprop-1′-enyl)-3-hydroxy-6-isopropyl-8-methylbicyclo[4.2.0]oct-7-ylidene]butanoic acid;

(1′E)-(3′S,1S,2S,3S,6R)-4-[2-(3′-hydroxy-3′-cyclohexylprop-1′-enyl)-3-hydroxy-6-n-hexyl-8-n-hexylbicyclo[4.2.0]oct-7-ylidene]butanoic acid; and (1′E)-(3′R,1S,2S,3S,6R)-4-[2-(3′-hydroxy-3′-cyclohexylprop-1′-enyl)-3-hydroxy-6-n-hexyl-8-n-hexylbicyclo[4.2.0]oct-7-ylidene]butanoic acid.

(3′R,1R,2R,3R,6S)-4-[2-(3′-hydroxy-3′-cyclohexylprop-1′-yl)-3-hydroxy-6-ethylbicyclo[4.2.0]oct-7-ylidene]butanoic acid;

(3′R,1S,2S,3S,6R)-4-[2-(3′-hydroxy-3′cyclohexylprop-prop-1′-yl)-3-hydroxy-6-ethlbicyclo[4.2.0]oct-7-ylidene]butanoic acid;

(3′R,1S,2S,3S,6R)-5-[2-(3′-hydroxy-3′-cyclohexylprop-1′yl)-3-hydroxy-6-ethylbicyclo[4.2.0]oct-7-ylidene]pentanoic acid;

(3′S,1S,2S,3S,6R)-6-[2-(3′-hydroxy-3′-cyclohexylprop-1′yl)-3-hydroxy-6-ethylbicyclo[4.2.0]oct-7-ylidene]hexanoic acid;

(3′R,1S,2S,3S,6R)-4-[2-(3′-hydroxy-3′-cyclohexylprop-1′yl)-3-hydroxy-6-ethylbicyclo[4.2.0]oct-7-ylidene]butanoic acid;

(3′R,1R,2R,3R,6R)-4-[2-(3′-hydroxy-3′-cyclohexylprop-1′-yl)-3-hydroxy-6-isopropylbicyclo[4.2.0]oct-7-ylidene]butanoic acid;

(3′S,1S,2S,3S,6S)-4-[2-(3′-hydroxy-3′-cyclohexylprop-1′-yl)-3-hydroxy-6-isopropylbicyclo[4.2.0]oct-7-ylidene]butanoic acid;

(3′R,1S,2S,3S,6S)-4-[2-(3′-hydroxy-3′-cyclohexylprop-1′-yl)-3-hydroxy-6-isopropylbicyclo[4.2.0]oct-7ylidene]butanoic acid;

(3′R,1R,2R,3R,6S)-4-[2-(3′-hydroxy-3′-cyclohexylprop-1′-yl)-3-hydroxy-6-n-hexylbicyclo[4.2.0]oct-7ylidene]butanoic acid;

(3′S,1S,2S,3S,6R)-4-[2-(3′-hydroxy-3′-cyclohexylprop-1′-yl)-3-hydroxy-6-n-hexylbicyclo[4.2.0]oct-7-ylidene]butanoic acid;

(3′R,1S,2S,3S,6R)-4-[2-(3′-hydroxy-3′-cyclohexylprop-1′-yl)-3-hydroxy-6-n-hexylbicyclo[4.2.0]oct-7-ylidene]butanoic acid;

(3′R,1R,2R,3R,6S)-4-[2-(3′-hydroxy-4′-cyclohexylbut-1′-yl)-3-hydroxy-6-methylbicyclo[4.2.0]oct-7-ylidene]butanoic acid;

(3′S,1S,2S,3S,6R)-4-[2-(3′-hydroxy-4′-cyclohexylbut-1′-yl)-3-hydroxy-6-methylbicyclo[4.2.0]oct-7-ylidene]butanoic acid;

(3′R,1S,2S,3S,6R)-4-[2-(3′-hydroxy-4′-cyclohexylbut-1′-yl)-3-hydroxy-6-methylbicyclo[4.2.0]oct-7-ylidene]butanoic acid;

(3'R,1R,2R,3R,6S)-4-[2-(3'-hydroxy-4'-cyclopentylbut-1'-yl)-3-hydroxy-6-methylbicyclo[4.2.0]oct-7-ylidene]butanoic acid;
(3'S,1S,2S,3S,6R)-4-[2-(3'-hydroxy-4'-cyclopentylbut-1'-yl)-3-hydroxy-6-methylbicyclo[4.2.0]oct-7-ylidene]butanoic acid;
(3'R,1S,2S,3S,6R)-4-[2-(3'-hydroxy-4'-cyclopentylbut-1'-yl)-3-hydroxy-6-methylbicyclo[4.2.0]oct-7-ylidene]butanoic acid;
(3'S,1R,2R,3R,6S)-4-[2-(3'-hydroxydec-1'-yl)-3-hydroxy-6-methylbicyclo[4.2.0]oct-7-ylidene]butanoic acid;
(3'R,1S,2S,3S,6R)-4-[2-(3'-hydroxydec-1'-yl)-3-hydroxy-6-methylbicyclo[4.2.0]oct-7-ylidene]butanoic acid;
(3'S,1S,2S,3S,6R)-4-[2-(3'-hydroxydec-1'-yl)-3-hydroxy-6-methylbicyclo[4.2.0]oct-7-ylidene]butanoic acid;
(3'R,1R,2R,3R,6S)-4-[2-(3'-hydroxy-4'-phenoxybut-1'-yl)-3-hydroxy-6-methylbicyclo[4.2.0]oct-7-ylidene]butanoic acid;
(3'S,1S,2S,3S,6R)-4-[2-(3'-hydroxy-4'-phenoxybut-1'-yl)-3-hydroxy-6-methylbicyclo[4.2.0]oct-7-ylidene]butanoic acid;
(3'R,1S,2S,3S,6R)-4-[2-(3'-hydroxy-4'-phenoxybut-1'-yl)-3-hydroxy-6-methylbicyclo[4.2.0]oct-7-ylidene]butanoic acid;
(3'R,1R,2R,3R,6S)-4-[2-(3'-hydroxy-3'-cyclohexylprop-1'-yl)-3-hydroxy-6,8-dimethylbicyclo[4.2.0]oct-7-ylidene]butanoic acid;
(3'S,1S,2S,3S,6R)-4-[2-(3'-hydroxy-3'-cyclohexylprop-1'-yl)-3-hydroxy-6,8-dimethylbicyclo[4.2.0]oct-7-ylidene]butanoic acid;
(3'R,1S,2S,3S,6R)-5-[2-(3'-hydroxy-3'-cyclohexylprop-1'-yl)-3-hydroxy-6,8-dimethylbicyclo[4.2.0]oct-7-ylidene]pentanoic acid;
(3'R,1S,2S,3S,6R)-6-[2-(3'-hydroxy-3'-cyclohexylprop-1'-yl)-3-hydroxy-6,8-dimethylbicyclo[4.2.0]oct-7-ylidene]hexanoic acid;
(3'R,1S,2S,3S,6R)-4-[2-(3'-hydroxy-3'-cyclohexylprop-1'-yl)-3-hydroxy-6,8-dimethylbicyclo[4.2.0]oct-7-ylidene]butanoic acid;
(3'R,1R,2R,3R,6S)-4-[2-(3'-hydroxy-4'-cyclohexylbut-1'-yl)-3-hydroxy-6,8-dimethylbicyclo[4.2.0]oct-7-ylidene]butanoic acid;
(3'S,1S,2S,3S,6R)-4-[2-(3'-hydroxy-4'-cyclohexylbut-1'-yl)-3-hydroxy-6,8-dimethylbicyclo[4.2.0]oct-7-ylidene]butanoic acid;
(3'R,1S,2S,3S,6R)-4-[2-(3'-hydroxy-4'-cyclohexylbut-1'-yl)-3-hydroxy-6,8-dimethylbicyclo[4.2.0]oct-7-ylidene]butanoic acid;
(3'R,1R,2R,3R,6S)-4-[2-(3'-hydroxy-4'-cyclopentylbut-1'-yl)-3-hydroxy-6,8-dimethylbicyclo[4.2.0]oct-7-ylidene]butanoic acid;
(3'S,1S,2S,3S,6R)-4-[2-(3'-hydroxy-4'-cyclopentylbut-1'-yl)-3-hydroxy-6,8-dimethylbicyclo[4.2.0]oct-7-ylidene]butanoic acid;
(3'R,1S,2S,3S,6R)-4-[2-(3'-hydroxy-4'-cyclopentylbut-1'-yl)-3-hydroxy-6,8-dimethylbicyclo[4.2.0]oct-7-ylidene]butanoic acid;
(3'R,1R,2R,3R,6S)-4-[2-(3'-hydroxy-4'-phenoxybut-1'-yl)-3-hydroxy-6,8-dimethylbicyclo[4.2.0]oct-7-ylidene]butanoic acid;
(3'S,1S,2S,3S,6R)-4-[2-(3'-hydroxy-4'-phenoxybut-1'-yl)-3-hydroxy-6,8-dimethylbicyclo[4.2.0]oct-7-ylidene]butanoic acid;
(3'R,1S,2S,3S,6R)-4-[2-(3'-hydroxy-4'-phenoxybut-1'-yl)-3-hydroxy-6,8-dimethylbicyclo[4.2.0]oct-7-ylidene]butanoic acid;
(3'R,1R,2R,3R,6S)-4-[2-(3'-hydroxy-3'-cyclohexylprop-1'-yl)-3-hydroxy-6-methyl-8-ethylbicyclo[4.2.0]oct-7-ylidene]butanoic acid;
(3'S,1S,2S,3S,6R)-4-[2-(3'-hydroxy-3'-cyclohexylprop-1'-yl)-3-hydroxy-6-methyl-8-ethylbicyclo[4.2.0]oct-7-ylidene]butanoic acid;
(3'R,1S,2S,3S,6R)-4-[2-(3'-hydroxy-3'-cyclohexylprop-1'-yl)-3-hydroxy-6-methyl-8-ethylbicyclo[4.2.0]oct-7-ylidene]butanoic acid;
(3'R,1R,2R,3R,6S)-4-[2-(3'-hydroxy-3'-cyclohexylprop-1'-yl)-3-hydroxy-6-methyl-8-n-hexylbicyclo[4.2.0]oct-7-ylidene]butanoic acid;
(3'S,1S,2S,3S,6R)-4-[2-(3'-hydroxy-3'-cyclohexylprop-1'-yl)-3-hydroxy-6-methyl-8-n-hexylbicyclo[4.2.0]oct-7-ylidene]butanoic acid;
(3'R,1S,2S,3S,6R)-4-[2-(3'-hydroxy-3'-cyclohexylprop-1'-yl)-3-hydroxy-6-methyl-8-n-hexylbicyclo[4.2.0]oct-7-ylidene]butanoic acid;
(3'R,1R,2R,3R,6S)-4-[2-(3'-hydroxy-3'-cyclohexylprop-1'-yl)-3-hydroxy-6-ethyl-8-methylbicyclo[4.2.0]oct-7-ylidene]butanoic acid;
(3'S,1S,2S,3S,6R)-4-[2-(3'-hydroxy-3'-cyclohexylprop-1'-yl)-3-hydroxy-6-ethyl-8-methylbicyclo[4.2.0]oct-7-ylidene]butanoic acid;
(3'R,1S,2S,3S,6R)-4-[2-(3'-hydroxy-3'-cyclohexylprop-1'-yl)-3-hydroxy-6-ethyl-8-methylbicyclo[4.2.0]oct-7-ylidene]butanoic acid;
(3'R,1R,2R,3R,6R)-4-[2-(3'-hydroxy-3'-cyclohexylprop-1'-yl)-3-hydroxy-6-isopropyl-8-methylbicyclo[4.2.0]oct-7-ylidene]butanoic acid;
(3'R,1S,2S,3S,6S)-4-[2-(3'-hydroxy-3'-cyclohexylprop-1'-yl)-3-hydroxy-6-isopropyl-8-methylbicyclo[4.2.0]oct-7-ylidene]butanoic acid;
(3'R,1R,2R,3R,6S)-4-[2-(3'-hydroxy-3'-cyclohexylprop-1'-yl)-3-hydroxy-6-n-hexyl-8-n-hexylbicyclo[4.2.0]oct-7-ylidene]butanoic acid;
(3'S,1S,2S,3S,6R)-4-[2-(3'-hydroxy-3'-cyclohexylprop-1'-yl)-3-hydroxy-6-n-hexyl 8-n-hexylbicyclo[4.2.0]oct-7-ylidene]butanoic acid; and
(3'R,1S,2S,3S,6R)-4-[2-(3'-hydroxy-3'-cyclohexylprop-1'-yl)-3-hydroxy-6-n-hexyl-8-n-hexylbicyclo[4.2.0]oct-7-ylidene]butanoic acid.

D. If in Preparation 11 the chiral lithium salt of (S)-3-t butyldimethylsilyloxy-3-cyclohexylprop-1-yne is replaced with a racemic compound of formula B, i.e. prepared from a racemic acetylenic alcohol, the subsequent preparations set forth above will yield racemic compounds of formula (1), (2) and (3) rather than optically pure compounds. For example:

(Z)-(3'SR,1SR,2RS,3SR,6RS)-4-[2-(3'-hydroxy-3'-cyclohexylprop-1'-ynyl)-3-hydroxy-6-methylbicyclo[4.2.0]oct-7-ylidene]butanoic acid;
(Z)-(3'SR,1SR,2RS,3SR,6RS)-4-[2-(3'-hydroxy-3'-cyclohexylprop-1'-ynyl)-3-hydroxy-6-ethylbicyclo[4.2.0]oct-7-ylidene]butanoic acid;
(Z)-(3'SR,1SR,2RS,3SR,6RS)-4-[2-(3'-hydroxy-3'-cyclohexylprop-1'-ynyl)-3-hydroxy-6-methyl-8-exo-methylbicyclo[4.2.0]oct-7-ylidene]butanoic acid;
(Z)-(3'SR,1SR,2RS,3SR,6RS)-4-[2-(3'-hydroxy-3'-cyclohexylprop-1'-ynyl)-3-hydroxy-6-methyl-8-endo-methylbicyclo[4.2.0]oct-7-ylidene]butanoic acid;
(Z)-(3'SR,1SR,2RS,3SR,6RS)-4-[2-(3'-hydroxy-3'-cyclohexylprop-1'-ynyl)-3-hydroxy-6-methylbicyclo[4.2.0]oct-7-ylidene]pentanoic acid;

(Z)-(3'SR,1RS,2SR,3RS,6SR)-4-[2-(3'-hydroxy-3'-cyclohexylprop-1'-ynyl)-3-hydroxy-6-methylbicyclo[4.2.0]oct-7-ylidene]butanoic acid;

(Z)-(3'SR,1RS,2SR,3RS,6SR)-4-[2-(3'-hydroxy-3'-cyclohexylprop-1'-ynyl)-3-hydroxy-6-methyl-8-exo-methylbicyclo[4.2.0]oct-7-ylidene]butanoic acid;

(Z)-(3'SR,1RS,2SR,3RS,6SR)-4-[2-(3'-hydroxy-3'-cyclohexylprop-1'-ynyl)-3-hydroxy-6-methyl-8-endo-methylbicyclo[4.2.0]oct-7-ylidene]butanoic acid; and (Z)-(3'RS,1SR,2SR,3SR,6RS)-4-[2-(3'-hydroxy-3'-cyclohexylprop-1-yl)-3-hydroxy-6-methyl-8-exo-methylbicyclo[4.2.0]oct-7-ylidene]butanoic acid.

EXAMPLE 2

Preparation of Salt Derivatives from Acids

This example illustrates methods for preparing the pharmaceutically acceptable salts of the invention. To prepare a sodium salt, for example, of a compound of formula (1), (2) or (3) where $R_1$ is $CO_2H$, for example (Z)-(3'S,1S,2R,3S,6R)-4-[2-(3'-hydroxy-3'-cyclohexylprop-1'-ynyl)-3-hydroxy-6-methylbicyclo[4.2.0.]oct-7-ylidene]butanoic acid, the acid is dissolved in methanol and one molar equivalent of sodium hydroxide dissolved in water is added. The solvent is removed under reduced pressure and the residue recrystallized from a suitable solvent, for example ethyl acetate methanol, to furnish the desired sodium salt.

The sodium salts of other compounds of formula (1), (2) or (3), where $R_1$ is $CO_2H$, made as shown in Example 1, are similarly prepared using the above procedure. Other salts are similarly prepared, replacing sodium hydroxide with the desired base.

EXAMPLE 3

Preparation of Acid Derivatives from Salts

The sodium salt of (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butanoic acid, prepared as shown in Example 3, is suspended in ethyl acetate and stirred with 2 molar equivalents of dilute aqueous sulfuric acid until the salt is completely dissolved. The organic layer is separated, washed with water, dried over magnesium sulfate and evaporated to give (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butanoic acid.

Similarly, other salts of compounds of formula (1), (2) or (3) where $R_1$ is $CO_2H$ are converted to the corresponding free acid.

EXAMPLE 4

Preparation of Methtl (Z)-(3'S,1S,2R,3S,6R)-4-[2(3'-hydroxy-3-cyclohexylprop-1'-ynyl)-3-hydroxy-6-methylbicyclo[4.2.0]oct-7-ylidene]butyrate and Related Esters of the Compounds of Formula (I)

A. A solution of (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butyric acid, prepared as shown in Example 1, is dissolved in ether and treated with an ethereal solution containing a molar excess of diazomethane. The yellow mixture is held at room temperature for 2 hours, then acetic acid is added dropwise until the remaining color is discharged. Solvent is removed by evaporation under reduced pressure, and the virtually pure residue so obtained is given a final purification by chromatography on silica gel, eluting with 4% methanol in methylene chloride to furnish the title compound.

B. In similar fashion but substituting higher diazoalkanes for the diazomethane employed in the preceeding example, the corresponding higher alkyl esters of the starting acid are prepared. The requisite diazoalkanes are known. They may be prepared, by conventional methods, e.g. as described in *Org. Reactions,* 8, 389–94, (1954).

Furthermore, by employing the procedure and diazoalkane reagents of this Example but substituting the other acid products of formula (1), (2) or (3) prepared according to Example 1 for the starting material utilized above, the corresponding alkyl esters of each acid product of formula (1), (2) or (3) are prepared.

EXAMPLE 5

Preparation of Free Carboxylic Acids by Hydrolysis of the Corresponding Ester

This Example describes preparation of the carboxylic acids of our invention of formula (1), (2) or (3) by hydrolysis of their corresponding alkyl esters. Hydrolysis may be carried out employing a wide variety of organic and/or inorganic bases under conventional and well-known reaction conditions. The following procedure is given for illustrative purposes only and is not intended to be limiting in any sense.

A solution of the methyl ester (0.05 g) of (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butyric acid, prepared according to Example 5, in 3 ml of methanol is purged with argon and stirred under an argon atmosphere while 0.5 ml of in aqueous NaOH is added. Stirring is continued for 4 hours at ambient temperature, followed by evaporation of most of the solvent under reduced pressure. The concentrate is diluted with 10 ml of $H_2O$ and, after adjusting the pH to between 5.5 and 6.5, extracted with 3 portions of methylene chloride. The combined extracts are washed with saturated brine, dried over sodium sulfate, and evaporated under reduced pressure to afford the free carboxylic acid, i.e., (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butyric acid. Similarly, the other esters prepared from the novel acids of our invention are hydrolysed to furnish the corresponding free acid.

EXAMPLE 6

Compounds Wherein $R_1$ is $CH_2OH$

Preparation of Methyl Z-(3'S,1S,2R,3S,6R)-4-[2-(3'-tert-butyldimethylsilyloxy-3'-cyclohexylprop-1'-ynyl)-3-tert-butyldimethylsilyloxy-6-methylbicyclo[4.2.0]oct-7-ylidene]butyrate and Related Compounds A mixture of 0.52 g of methyl Z-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butyrate, 0.55 g tert-butyldimethylsilyl chloride, 0.18 g of 4-dimethylaminopyridine, 2 ml triethylamine and 10 ml dichloromethane is stirred at 23° C. for 24 hours. After dilution with 20 ml of dichloromethane the mixture is washed with 10 ml water, three 20 ml portions of 1N HCl and 10 ml sat. sodium bicarbonate. After drying over sodium sulfate the solvent is removed to give 0.76 of the title compound.

B. In similar fashion, substituting other esters of the compounds of the formula (1), (2) and (3), the corresponding protected compounds are prepared.

C. Preparation of Z-(3'S,1S,2R,3S,6R)-4-[2-(3'-tert-butyldimethylsilyloxy-3'-cyclohexylprop-1'-ynyl)-3-tert-butyldimethylsilyloxy-6-methylbicyclo[4.2.0]oct-7-ylidene]butan-1-ol and Related Compounds To a stirred mixture of 0.1 g lithium aluminum hydride in 15 ml diethyl ether is added in dropwise fashion a solution of 0.78 g of methyl Z-(3'S,1S,2R,3S,6R)-4-[2-(3'tert-butyldimethylsilyloxy-3'-cyclohexylprop-1'-ynyl)-3-tert-butyldimethylsilyloxy-6-methylbicyclo[4.2.0]oct-7-ylidene]butyrate in 5 ml of diethyl ether. This mixture is heated at reflux for 2 h. After cooling the reaction is worked up by sequential dropwise addition of 0.1 ml water, 0.1 ml 15% sodium hydroxide, and 0.3 ml water. The resulting precipitate is removed by filtration. Evaporation of the filtrate gives the title compound.

In a similar manner, but starting instead with other appropriate esters, prepared according to the method described in paragraph A above, other alcohols are prepared.

D. Preparation of Z-(3'S,1S,2R,3S,6R)-4-[2-(3'-hydroxy-3'-cyclohexylprop-1'-ynyl)-3-hydroxy-6-methylbicyclo[4.2.0]oct-7-ylidenelbutan-1-ol and related compounds of Formulas (1), (2) and (3) in which $R_1$ is $CH_2OH$.

To a solution of 0.15 g Z-(3'S,1S,2R,3S,6R)-4[2-(3-'-tert-butyldimethylsilyloxy-3'-cyclohexylprop1'-ynyl)-3-tert-butyldimethylsilyloxy-6-methylbicyclo[4.2.0]oct-7-ylidene]-1-butanol in 3 ml tetrahydrofuran is added 5 ml of a 1M solution of tetrabutylammonium fluoride in tetrahydrofuran. After 12 hours at 23° C. the solution is diluted with 20 ml water and the product is extracted into diethyl ether. Evaporation of the solvent and purification of the product using silica gel flash chromatography with ethyl acetate-hexane (1:1) gives the title compound.

In like manner, but starting with the appropiate alcohol, the preparation of which is described in Example C above, other compounds of formula (1), (2) or (3) are prepared where $R_1$ is $-CH_2OH$.

EXAMPLE 7

Preparation of Z-(3'S,1S,2R,3S,6R)-4-[2-(3'-hydroxy-3'-cyclohexylprop-1'-ynyl)-3-hydroxy-6-methylbicyclo[4.2.0]oct-7-ylidenelbutan-1-ol and related compounds of Formulas (1), (2) or (3) wherein $R_1$ is CHO.

A. To a stirred mixture of 0.25 g pyridinium chlorochromate in 7 ml dichloromethane is added a solution of 0.2 g of Z-(3'S,1S,2R,3S,6R)-4-[2-(3'tert-butyldimethylsilyloxy-3'-cyclohexylprop-1'-ynyl)-3-tert-butyldimethylsilyloxy-6methylbicyclo[4.2.0]oct-7-ylidene]1-butanol, prepared according to Example 6, in 3 ml dichloromethane. After 4 hours at 23° C. the solution is decanted from the precipitate and filtered through 10 g Florisil with dichloromethane. The filtrate is concentrated to a residue, which is dissolved in 3 ml tetrahydrofuran. To this solution is added 2 ml of a 1M solution of tetrabutylammonium fluoride in tetrahydrofuran. After 16 hours at 23° C. this solution is diluted with 20 ml water and the product extracted into diethyl ether. Evaporation of solvent followed by silica gel flash chromatography using ethyl acetate-hexane (30:70) gives the title compound.

B. In a similar manner, starting with other appropiate alcohols, and following the procedures of Example 7A above, other compounds of formula (1), (2) or (3) where $R_1$ is —CHO are prepared.

EXAMPLE 8

Preparation of p-Benzamidophenyl Z-(3'S,1S,2R,3S,6R)-4-[2-(3'-hydroxy-3'-cyclohexylprop-1'-ynyl)-3-hydroxy-6-methylbicyclo]4.2.0]oct-7-ylidene]butyrate, and related compounds of Formulas (1), (2) and (3) in which $R_1$ is $CO_2R$.

A. A solution of Z-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butyric acid (35 mg,) in acetone (2.7 mL) is treated with triethylamine (28.1 $\mu$L, 0.202 mmol). The solution is cooled to 5° C. under $N_2$ and isobutyl chlorocarbonate (27.3 $\mu$L, 0.202 mmol) added. After 5 minutes at −5° C., a solution of p-benzamidophenol (109.2 mg, 0.51 mmol) in dry pyridine (1.1 mL) is added. After 3 hours at room temperature, the solvent is removed under vacuum. The residue is extracted with dichloromethane and the solid (excess p-benzamidophenol) is removed by filtration. After evaporation of the solvent, the residue is purified by column chromotography using 30% acetone in-hexane to afford the title compound.

B. In like manner, but starting with other appropriate compounds of Formulas (1), (2) or (3) in which $R_1$ is $CO_2H$, and substituting for the p-benzamidophenol other appropriate substituted phenols, other compounds in which $R_1$ is $CO_2R$ are prepared.

EXAMPLE 9

Determination of Inhibition of Platelet Aggregation

Human venous blood from drug-free healthy volunteers is collected into 15 ml-vacutainers and anticoagulated with 0.5 ml of 11.4% sodium citrate. The blood is centrifuged at room temperature for 15 minutes at 150 G in a Sorvall GLC-28 centrifuge and the supernatant platelet-rich plasma (PRP) is collected by aspiration. Platelet-poor plasma (PPP) is prepared by centrifuging the blood from which PRP has been removed at 12,800 g for minutes in an Eppendorf centrifuge at room temperature. Platelet aggregation is carried out by the method of Born (J. Physiology, 168, 178 (1963)) in Payton aggregometers. Platelet aggregation is induced by adding ADP (2–5-nmoles) into 1 ml of PRP containing 10 $\mu$l of various concentrations of test compounds or vehicle incubated in the aggregometer cuvette at 37° C. for 5 minutes with the stirring speed set at 500 rpm. Then, for each test compound, a percent inhibition versus concentration curve is drawn on semi logarithmic paper and the concentration corresponding to 50% inhibition is expressed as the $IC_{50}$ for this compound. All the test compounds (1–2 mg) are prepared as 0.01M stock solutions in 10% ethanol and 59 mM $Na_2CO_3$. Subsequent dilutions are made with water.

EXAMPLE 10

Determination of Antihypertensive Activity

The antihypertensive effects of the prostaglandin like compounds are evaluated in spontaneously hypertensive rats (SHR/NCrlBR). Under ether anesthesia, femoral arterial and venous cannulae are implanted and the rats are restrained in a supine position. After recovery from the anesthesia, lidocaine is administered. Blood pressures are obtained via the femoral arterial cannula and recorded on a Beckman R611 polygraph. Groups of four rats are studied for each compound. Vehicle is administered at the beginning of the study and compound is intravenously administered at 30 min intervals thereafter, at increasing doses of 1, 3, 10, 30 and 100 μg/Kg. Baseline mean arterial blood pressure is the blood pressure immediately prior to the first dose of the compound. $ED_{20}$s are calculated from a linear regression of the percent decrease of mean blood pressures following each dose of the compound. The duration of activity is determined based on the recovery to 90% of the control blood pressure following the 100μg/Kg, i.v., dose.

EXAMPLE 11

Composition

| | Formulation | |
|---|---|---|
| Ingredient | Amount mg | Amount (1000 Tablets) |
| Sodium (Z)-(3'S,1S,2R,3S,6R)-4-[2-(3'-hydroxy-3'-cyclo-hexylprop-1'-ynyl)-3-hydroxy-6-methylbicyclo[4.2.0]oct-7-ylidene]butyrate | 52.6 | 52.6 Gm |
| Spray Dried Lactose | 200 | 200 Gm |
| Magnesium Stearate | 3 | 3 Gm |

Preparation

The above ingredients are homogeneously mixed and the power mixture then compressed into approximately 256 mg tablets each containing approximately 52.6 mg of the active ingredient.

Similarly, the active ingredient in the above formulation may be replaced by other compounds of formula (1), (2) or (3), or their pharmaceutically acceptable salts or esters, to give a suitable composition.

What we claim is:

1. A compound of the formula (1), (2) or (3):

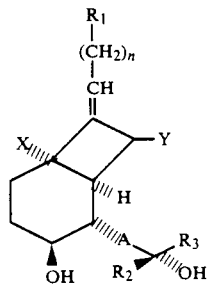 (1)

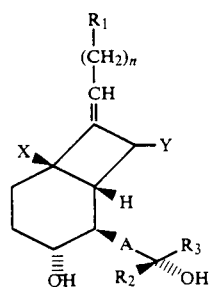 (2)

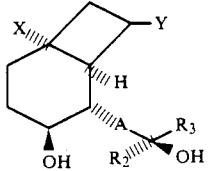 (3)

wherein:
A is —C≡C—, trans —HC=CH—, trans —CH=CHCH$_2$— or —CH$_2$CH$_2$—;
X is lower alkyl of 1-6 carbon atoms;
Y is hydrogen, exo-(lower alkyl) or endo-(lower alkyl);
n is an integer from 2-4;
$R_1$ is —CH$_2$OH, —CHO, CO$_2$R or CO$_2$H, and the olefin formed by the $R_1(CH_2)_n$CH= moiety is either (E) or (Z);
$R_2$ is hydrogen or methyl, or optionally —CH=CH$_2$ when A is trans —CH=CHCH$_2$—; and
$R_3$ is linear or branched alkyl, alkenyl or alkynyl having 5-10 carbon atoms,

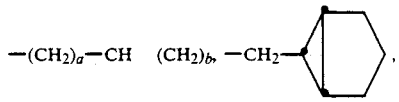

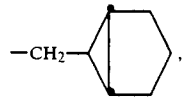

—(CH$_2$)$_m$-phenyl or CH$_2$O-phenyl;
in which each phenyl may be optionally substituted with lower alkyl, lower alkoxy, trifluoromethyl, or halogen. in which:
a is an integer of 0, 1 or 2;
b is an integer of 3-7;
m is an integer of 0, 1 or 2; and
R is

wherein X' is

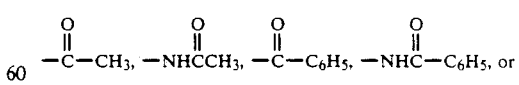

in which each R$_4$ is independently hydrogen or lower alkyl having 1-6 carbon atoms,
or a pharmaceutically acceptable, non toxic salt or alkyl ester thereof.

2. The compound of claim 1 in which the olefin formed by the $R_1(CH_2)_nCH=$ moiety is (Z), or a pharmaceutically acceptable non-toxic salt or alkyl ester thereof.

3. The compound of claim 2 represented by formula (1) or (2), or a pharmaceutically acceptable non-toxic salt or alkyl ester thereof.

4. The compound of claim 3 in which X is lower alkyl of 1–3 carbon atoms, Y is hydrogen or lower alkyl of 1–3 carbon atoms and n is 2 or 3, or a pharmaceutically acceptable non-toxic salt or alkyl ester thereof.

5. The compound of claim 4 in which A is —C≡C— or a pharmaceutically acceptable non-toxic salt or alkyl ester thereof.

6. The compound of claim 5 in which $R_2$ is hydrogen and $R_3$ is

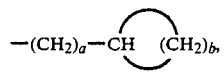

or a pharmaceutically acceptable non-toxic salt or alkyl ester thereof.

7. The compound of claim 6 in which a is zero and b is 5, or a pharmaceutically acceptable non-toxic salt or alkyl ester thereof.

8. The compound of claim 7 represented by the formula (1) in which $R_1$ is —$CO_2H$, or a pharmaceutically acceptable non-toxic salt or alkyl ester thereof.

9. The compound of claim 8 as a single enantiomer in which X is methyl, Y is hydrogen and n is 2, namely (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]butanoic acid, or a pharmaceutically acceptable non toxic salt or alkyl ester thereof.

10. The racemic compound of claim 8 in which X is methyl, Y is hydrogen and n is 2, namely (Z)-(3'SR,1SR,2RS,3SR,6RS)-4-[2-(3'-hydroxy-3'-cyclohexylprop-1'-ynyl)-3-hydroxy-6-methylbicyclo[4.2.0]oct-7-ylidene]butanoic acid, or a pharmaceutically acceptable non-toxic salt or alkyl ester thereof.

11. The compound of claim 8 as a single enantiomer in which X is ethyl, Y is hydrogen and n is 2, namely (Z)-(3'S,1S,2R,3S,6R)-4-[2-(3'-hydroxy-3'-cyclohexylprop-1'-ynyl)-3-hydroxy-6-ethylbicyclo[4.2.0]oct-7-ylidene]butanoic acid, or a pharmaceutically acceptable non toxic salt or alkyl ester thereof.

12. The racemic compound of claim 8 in which X is ethyl, Y is hydrogen and n is 2, namely (Z)-(3'SR,1SR,2RS,3SR,6RS)-4-[2-(3'-hydroxy-3'-cyclohexylprop-1'-ynyl)-3-hydroxy-6-ethylbicyclo[4.2.0]oct-7-ylidene]butanoic acid, or a pharmaceutically acceptable non toxic salt or alkyl ester thereof.

13. The compound of claim 8 as a single enantiomer in which X is methyl, Y is exo-methyl and n is 2, namely (Z)-(3'S,1S,2R,3S,6R)-4-[2-(3'-hydroxy-3'-cyclohexylprop-1'-ynyl)-3-hydroxy-6-methyl-8-exo-methylbicyclo[4.2.0]oct-7-ylidene]butanoic acid, or a pharmaceutically acceptable non toxic salt or alkyl ester thereof.

14. The racemic compound of claim 8 in which X is methyl, Y is exo-methyl and n is 2, namely (Z)-(3'SR,1SR,2RS,3SR,6RS)-4-[2-(3'-hydroxy-3'-cyclohexylprop-1'-ynyl)-3-hydroxy-6-methyl-8-exo-methylbicyclo[4.2.0]oct-7-ylidene]butanoic acid, or a pharmaceutically acceptable non-toxic salt or alkyl ester thereof.

15. The compound of claim 8 as a single enantiomer in which X is methyl, Y is endo-methyl and n is 2, namely (Z)-(3'S,1S,2R,3S,6R)-4-[2-(3'-hydroxy-3'-cyclohexylprop-1'-ynyl)-3-hydroxy-6-methyl-8-endo-methylbicyclo[4.2.0]oct-7-ylidene]butanoic acid, or a pharmaceutically acceptable non-toxic salt or alkyl ester thereof.

16. The racemic compound of claim 8 in which X is methyl, Y is endo-methyl and n is 2, namely (Z)-(3'SR,1SR,2RS,3SR,6RS)-4-[2-(3'-hydroxy-3'-cyclohexylprop-1'-ynyl)-3-hydroxy-6-methyl-8-endo-methylbicyclo[4.2.0]oct-7-ylidene]butanoic acid, or a pharmaceutically acceptable non-toxic salt or alkyl ester thereof.

17. The compound of claim 8 as a single enantiomer in which X is methyl, Y is hydrogen and n is 3, namely (Z)-(3'S,1S,2R,3S,6R)-4-[2-(3'-hydroxy-3'-cyclohexylprop-1'-ynyl)-3-hydroxy-6-methylbicyclo[4.2.0]oct-7-ylidene]pentanoic acid, or a pharmaceutically acceptable non-toxic salt or alkyl ester thereof.

18. The racemic compound of claim 8 in which X is methyl, Y is hydrogen and n is 3, namely (Z)-(3'SR,1SR,2RS,3SR,6RS)-4-[2-(3'-hydroxy-3'-cyclohexylprop-1'-ynyl)-3-hydroxy-6-methylbicyclo[4.2.0]oct-7-ylidene]pentanoic acid, or a pharmaceutically acceptable non toxic salt or alkyl ester thereof.

19. The compound of claim 7 represented by the formula (2) in which $R_1$ is —$CO_2H$, or a pharmaceutically acceptable non-toxic salt or alkyl ester thereof.

20. The compound of claim 19 as a single enantiomer in which X is methyl, Y is hydrogen and n is 2, namely (Z)-(3'S,1R,2S,3R,6S)-4-[2-(3'-hydroxy-3'-cyclohexylprop-1'-ynyl)-3-hydroxy-6-methylbicyclo[4.2.0]oct-7-ylidene]butanoic acid, or a pharmaceutically acceptable non-toxic salt or alkyl ester thereof.

21. The racemic compound of claim 19 in which X is methyl, Y is hydrogen and n is 2, namely (Z)-(3'SR,1RS,2SR,3RS,6SR)-4-[2-(3'-hydroxy-3'-cyclohexylprop-1'-ynyl)-3-hydroxy-6-methylbicyclo[4.2.0]oct-7-ylidene]butanoic acid, or a pharmaceutically acceptable non-toxic salt or alkyl ester thereof.

22. The compound of claim 19 as a single enantiomer in which X is methyl, Y is exo-methyl and n is 2, namely (Z)-(3'S,1R,2S,3R,6S)-4-[2-(3'-hydroxy-3'-cyclohexylprop-1'-ynyl)-3-hydroxy-6-methyl-8-exo-methylbicyclo[4.2.0]oct-7-ylidene]butanoic acid, or a pharmaceutically acceptable non-toxic salt or alkyl ester thereof.

23. The racemic compound of claim 19 in which X is methyl, Y is exo-methyl and n is 2, namely (Z)-(3'SR,1RS,2SR,3RS,6SR)-4-[2-(3'-hydroxy-3'-cyclohexylprop-1'-ynyl)-3-hydroxy-6-methyl-8-exo-methylbicyclo[4.2.0]oct-7-ylidene]butanoic acid, or a pharmaceutically acceptable non-toxic salt or alkyl ester thereof.

24. The compound of claim 19 as a single enantiomer in which X is methyl, Y is endo-methyl and n is 2, namely (Z)-(3'S,1R,2S,3R,6S)-4-[2-(3'-hydroxy-3'-cyclohexylprop-1'-ynyl)-3-hydroxy-6-methyl-8-endomethylbicyclo[4.2.0]oct-7-ylidene]butanoic acid, or a pharmaceutically acceptable non-toxic salt or alkyl ester thereof.

25. The racemic compound of claim 19 in which X is methyl, Y is endo-methyl and n is 2, namely (Z)-(3'SR,1RS,2SR,3RS,6SR)-4-[2-(3'-hydroxy-3'-cyclohexylprop-1'-ynyl)-3-hydroxy-6-methyl-8-endo-methylbicyclo[4.2.0]oct-7-ylidene]butanoic acid, or a pharmaceutically acceptable non-toxic salt or alkyl ester thereof.

26. The compound of claim 2, wherein A is trans —CH=CH—, or a pharmaceutically acceptable non toxic salt or alkyl ester thereof.

27. The compound of claim 26 in which X is lower alkyl of 1–3 carbon atoms, Y is hydrogen or lower alkyl of 1–3 carbon atoms and n is 2 or 3, or a pharmaceutically acceptable non-toxic salt or alkyl ester thereof.

28. The compound of claim 27 in which $R_2$ is hydrogen and $R_3$ is

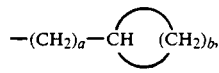

or a pharmaceutically acceptable non-tox salt or alkyl ester thereof.

29. The compound of claim 28 in which a is zero and b is 5, or a pharmaceutically acceptable non toxic salt or alkyl ester thereof.

30. The compound of claim 29 in which $R_1$ is —$CO_2H$, or a pharmaceutically acceptable non toxic salt or alkyl ester thereof.

31. The compound of claim 2, wherein A is —$CH_2CH_2$—, or a pharmaceutically acceptable non toxic salt or alkyl ester thereof.

32. The compound of claim 31 represented by formula (1) or (2), or a pharmaceutically acceptable non-toxic salt or alkyl ester thereof.

33. The compound of claim 32 in which X is lower alkyl of 1–3 carbon atoms, Y is hydrogen or lower alkyl of 1–3 carbon atoms and n is 2 or 3, or a pharmaceutically acceptable non-toxic salt or alkyl ester thereof.

34. The compound of claim 33 in which $R_2$ is hydrogen and $R_3$ is

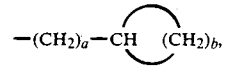

or a pharmaceutically acceptable non tox salt or alkyl ester thereof.

35. The compound of claim 34 in which a is zero and b is 5, or a pharmaceutically acceptable non-toxic salt or alkyl ester thereof.

36. The compound of claim 35 represented by the formula (1) in which $R_1$ is —$CO_2H$, or a pharmaceutically acceptable non-toxic salt or alkyl ester thereof.

37. The compound of claim 36 as a single enantiomer in which X is methyl, Y is exo methyl and n is 2, namely (Z)-(3'R,1S,2S,3S,6R)-4-[2-(3'-hydroxy-3'-cyclohexylprop-1-yl)-3-hydroxy-6-methyl-8-exo-methylbicyclo[4.2.0]oct-7-ylidene]butanoic acid, or a pharmaceutically acceptable non toxic salt or alkyl ester thereof.

38. The racemic compound of claim 36 in which X is methyl, Y is exo-methyl and n is 2, namely (Z)-(3'RS,1SR,2SR,3SR,6RS)-4-[2-(3'-hydroxy-3'-cyclohexylprop-1-yl)-3-hydroxy-6-methyl-8-exo-methylbicyclo[4.2.0]oct-7-ylidene]butanoic acid, or a pharmaceutically acceptable non toxic salt or alkyl ester thereof.

39. A method for treating cardiovascular disorders in mammals which comprises administering a therapeutically effective amount of a compound of claim 1, or a pharmaceutically acceptable non toxic salt or alkyl ester thereof, to a subject in need of such treatment.

40. The method of claim 39 in which the disorder is atherosclerosis.

41. The method of claim 39 in which the disorder involves a thrombotic condition.

42. The method of claim 39 in which the disorder involves a vasospastic condition.

43. The method of claim 39 in which the disorder is hypertension.

44. The method of claim 39 in which the disorder is elevated cholesterol levels.

45. A method for inhibiting gastric secretion in mammals which comprises administering a therapeutically effective amount of a compound of claim 1, or a pharmaceutically acceptable, non-toxic salt or ester thereof, to a subject in need of such a treatment.

46. A pharmaceutical composition suitable for administration to a mammal, containing at least one suitable pharmaceutical excipient and a therapeutically effective amount of a compound of claim 1 or a pharmaceutically acceptable, non-toxic salt or alkyl ester thereof.

* * * * *